US007549232B2

(12) United States Patent
Tadin

(10) Patent No.: US 7,549,232 B2
(45) Date of Patent: Jun. 23, 2009

(54) METHOD TO CAPTURE AND SUPPORT A 3-D CONTOUR

(75) Inventor: Tony Tadin, Woodside, CA (US)

(73) Assignee: Amfit, Inc., Vancouver, WA (US)

( * ) Notice: Subject to any disclaimer, the term of this patent is extended or adjusted under 35 U.S.C. 154(b) by 865 days.

(21) Appl. No.: 10/965,666

(22) Filed: Oct. 14, 2004

(65) Prior Publication Data

US 2005/0116380 A1 Jun. 2, 2005

Related U.S. Application Data

(60) Provisional application No. 60/511,015, filed on Oct. 14, 2003, provisional application No. 60/535,773, filed on Jan. 12, 2004, provisional application No. 60/549,248, filed on Mar. 2, 2004.

(51) Int. Cl.
*A61B 5/103* (2006.01)

(52) U.S. Cl. .................................................... 33/515

(58) Field of Classification Search ...................... None
See application file for complete search history.

(56) References Cited

U.S. PATENT DOCUMENTS

| | | | | |
|---|---|---|---|---|
| 133,679 | A | 12/1872 | Stoll | |
| 143,642 | A | 10/1873 | Rungvist | 73/530 |
| 507,099 | A | 10/1893 | Bazin | 114/67 A |
| 1,336,979 | A | 4/1920 | Plummer | |
| 1,523,469 | A | 1/1925 | Young et al. | 36/180 |
| 1,709,850 | A | 4/1929 | Hurley | 36/145 |
| 1,710,936 | A | 4/1929 | May | 36/145 |
| 1,867,431 | A | 7/1932 | Wood | 36/145 |
| 1,953,048 | A | 3/1934 | Crompton | 36/145 |
| 2,161,565 | A | 6/1939 | Freda | 36/180 |
| 2,383,583 | A | 8/1945 | Becker | 36/180 |
| 2,423,622 | A | 7/1947 | Samblanet | 36/176 |
| 2,499,327 | A | 2/1950 | Mead | 264/102 |
| 2,863,231 | A | 12/1958 | Jones | 36/174 |
| 3,265,071 | A | 8/1966 | Kirchner et al. | 36/145 |
| 3,406,468 | A | 10/1968 | Pujol | 36/88 |
| 3,459,179 | A | 8/1969 | Olesen | 601/134 |
| 3,552,044 | A | 1/1971 | Wiele | 36/71 |
| 3,861,398 | A | 1/1975 | Leydecker | 36/174 |
| 4,266,350 | A | 5/1981 | Laux | 36/44 |
| 4,272,898 | A | 6/1981 | Lansill | 36/44 |
| 4,316,334 | A | 2/1982 | Hunt | 36/91 |
| 4,346,525 | A | 8/1982 | Larsen et al. | 36/69 |
| 4,493,877 | A | 1/1985 | Burnett | 428/524.8 |
| 4,541,184 | A | 9/1985 | Leighton | 36/44 |

(Continued)

FOREIGN PATENT DOCUMENTS

| | | |
|---|---|---|
| CA | 1168440 | 6/1984 |

(Continued)

*Primary Examiner*—Christopher W Fulton
(74) *Attorney, Agent, or Firm*—Ohlandt, Greeley, Ruggiero & Perle, L.L.P.

(57) ABSTRACT

A method and system for a 3-D (three-dimensional) capture system including a flexible housing defining a substantially airtight reservoir therein, a volume of particles disposed in the reservoir, a volume of a gas and/or a liquid disposed in the reservoir; and a valve system in communication with the reservoir for selectively permitting the removal of at least the volume of the gas and/or the liquid therefrom. The captured 3-D impression is selectively erasable.

80 Claims, 57 Drawing Sheets

U.S. PATENT DOCUMENTS

| | | | | |
|---|---|---|---|---|
| 4,674,205 | A | 6/1987 | Anger | 36/44 |
| 4,677,766 | A | 7/1987 | Gudas | 36/43 |
| 4,841,648 | A | 6/1989 | Shaffer et al. | 36/43 |
| 4,932,141 | A | 6/1990 | Hones | 36/43 |
| 4,998,354 | A * | 3/1991 | Silverman et al. | 33/514.2 |
| 5,014,706 | A | 5/1991 | Philip | 36/140 |
| 5,154,185 | A | 10/1992 | Latimer et al. | 128/870 |
| 5,170,572 | A | 12/1992 | Kantro | 36/43 |
| 5,378,223 | A | 1/1995 | Grim et al. | 602/6 |
| 5,404,659 | A | 4/1995 | Burke et al. | 36/176 |
| 5,542,196 | A | 8/1996 | Kantro | 36/44 |
| 5,555,584 | A | 9/1996 | Moore, III et al. | 12/142 |
| 5,556,169 | A * | 9/1996 | Parrish et al. | 297/452.28 |
| 5,617,650 | A | 4/1997 | Grim | 36/88 |
| 5,970,631 | A | 10/1999 | Inman | 36/115 |
| 6,026,599 | A | 2/2000 | Blackwell et al. | 36/140 |
| 6,131,972 | A * | 10/2000 | Whitehead et al. | 294/57 |
| 6,430,831 | B1 * | 8/2002 | Sundman | 33/515 |
| 6,625,897 | B2 * | 9/2003 | Tadin | 33/515 |
| 6,703,142 | B2 * | 3/2004 | Snow | 428/522 |
| 6,742,289 | B2 | 6/2004 | Celmo | 36/141 |
| 6,823,550 | B2 | 11/2004 | Kantro | 12/142 N |
| 6,848,200 | B1 * | 2/2005 | Westin | 36/29 |
| 6,880,266 | B2 | 4/2005 | Schoenborn et al. | 36/28 |
| 7,082,704 | B2 | 8/2006 | Thorneburg et al. | 36/91 |
| 7,086,168 | B2 * | 8/2006 | Spivey | 33/515 |
| 7,120,958 | B2 | 10/2006 | Copeskey et al. | 12/142 N |
| 7,140,130 | B2 | 11/2006 | Brooks | 36/180 |
| 7,178,269 | B2 | 2/2007 | Bauerfeind et al. | 36/30 A |
| 2002/0007569 | A1 | 1/2002 | Crane et al. | 36/44 |
| 2003/0041481 | A1 | 3/2003 | Evans et al. | 36/145 |
| 2003/0046831 | A1 | 3/2003 | Westin | 36/29 |
| 2003/0172548 | A1 | 9/2003 | Fuerst | 36/28 |
| 2004/0078998 | A1 | 4/2004 | Davis et al. | 36/44 |
| 2004/0181971 | A1 | 9/2004 | Turkbas et al. | 36/44 |
| 2004/0194344 | A1 | 10/2004 | Tadin | 36/44 |
| 2005/0116380 | A1 * | 6/2005 | Tadin | 264/223 |
| 2005/0252039 | A1 | 11/2005 | Vindriis | 36/43 |
| 2006/0070260 | A1 | 4/2006 | Cavanagh | 36/44 |
| 2006/0121268 | A1 | 6/2006 | Graab et al. | 428/316.6 |
| 2006/0123663 | A1 | 6/2006 | Swenson | 36/43 |
| 2006/0185197 | A1 | 8/2006 | Rhenter | 36/174 |
| 2007/0039205 | A1 | 2/2007 | Erb et al. | 36/44 |

FOREIGN PATENT DOCUMENTS

| | | |
|---|---|---|
| CH | 83595 | 12/1919 |
| DE | 4006579 | 9/1990 |
| DE | 19610981 | 7/1997 |
| DE | 19627177 | 1/1998 |
| EP | 0913101 | 5/1999 |
| FR | 849155 | 11/1939 |
| FR | 2824884 | 11/2002 |
| GB | 2011243 | 7/1979 |
| GB | 2358121 | 7/2001 |
| JP | 2002282012 | 10/2002 |
| JP | 2005013682 | 1/2005 |
| JP | 2006141651 | 6/2006 |
| WO | WO91/06229 | 5/1991 |
| WO | WO 94/23604 | 10/1994 |
| WO | WO 99/37850 | 7/1999 |
| WO | WO 01/46143 | 7/2001 |

* cited by examiner

METHOD TO CAPTURE AND SUPPORT A 3-D CONTOUR

CROSS-REFERENCE TO RELATED APPLICATIONS

The present application is claiming priority of U.S. Provisional Patent Application Ser. No. 60/511,015, filed on Oct. 14, 2003, U.S. Provisional Patent Application Ser. No. 60/535,773, filed on Jan. 12, 2004, and U.S. Provisional Patent Application Ser. No. 60/549,248, filed on Mar. 2, 2004, the content of which is herein incorporated by reference.

BACKGROUND OF THE INVENTION

1. Field of the Invention

This invention relates to 3-D (three-dimensional) contour capturing and, more particularly, to a method and system for capturing and supporting a 3D contour of a subject object.

2. Description of the Related Art

In the prior art there are various known methods for capturing a 3D contour. However, the heretofore 3D capture systems do not provide an inexpensive, uncomplicated, clean, and accurate methodology for capturing the 3d contour of a subject item.

Therefore, there exists a need in many applications and contexts, such as but not limited to, the fields of customized seating, sleep surfaces, helmets, shipping containers, grips, foot supports, footwear and the like, where a 3D capture system overcoming the above-noted deficiencies would prove beneficial.

SUMMARY OF THE INVENTION

A method and system for a 3-D (three-dimensional) capture system is provided. A three-dimensional (3-D) capture system embodiment of the present invention includes a flexible housing defining a substantially airtight reservoir therein, a plurality of particles disposed in the reservoir, a gas and/or liquid disposed in the reservoir, and a valve assembly in communication with the reservoir for regulating a quantity of the gas and/or liquid disposed in the reservoir.

In another embodiment of the present invention, regulating includes removal of at least a portion of the gas and/or liquid in response to pressure on the reservoir, and the housing substantially retains a contour formed by the pressure after the pressure is removed.

In another embodiment of the present invention, the particles are elastomeric.

In another embodiment of the present invention, the particles are solid.

In another embodiment of the present invention, the particles are spherical, cylindrical, and/or randomly shaped.

In another embodiment of the present invention, the particles are of a size from about 0.1 mm to about 10 mm.

In another embodiment of the present invention, the particles have more than one density.

In another embodiment of the present invention, the particles have more than one hardness.

In another embodiment of the present invention, the valve assembly includes a unidirectional valve to control a flow of the gas and/or liquid.

In another embodiment of the present invention, the unidirectional valve includes a bypass capability to allow the gas and/or liquid to be selectively reintroduced into the housing.

In another embodiment of the present invention, the system includes a plug to prevent leaks of the gas and/or liquid through the valve assembly.

In another embodiment of the present invention, the valve assembly includes two or more valves.

In another embodiment of the present invention, the valve assembly includes an output valve and an input valve.

In another embodiment of the present invention, the system includes an electronic control system to control an opening of the valve assembly.

In another embodiment of the present invention, the system includes a shielding layer to prevent damage to the control system due to static charges.

In another embodiment of the present invention, the electronic control system includes a processor and a battery.

In another embodiment of the present invention, the system includes a remote control device to activate the control system.

In another embodiment of the present invention, the control system is voice activated.

In another embodiment of the present invention, the system includes a heat sensor. The heat sensor activates the control system when the system exceeds a selected temperature to allow the gas and/or liquid to enter the housing and cool the housing.

In another embodiment of the present invention, the particles are doped with an adhesive.

In another embodiment of the present invention, the particles are lubricated with a high viscosity material.

In another embodiment of the present invention, the particles are anti-static.

In another embodiment of the present invention, at least a portion of the particles can be fused together by an appropriately calibrated energy source.

In another embodiment of the present invention, the energy source is selected from a heater and a microwave device.

In another embodiment of the present invention, the reservoir has opposing surfaces selectively bonded together by a barrier to form at least two partitions to limit a migration of the particles between the at least two partitions.

In another embodiment of the present invention, the gas and/or liquid is an adhesive, water, or air.

In another embodiment of the present invention, the housing includes a mid layer and an outer layer, wherein the mid layer is disposed between the particles and the outer layer.

In another embodiment of the present invention, the mid layer is a mesh-type screen.

In another embodiment of the present invention, the housing forms a seating surface.

In another embodiment of the present invention, the seating surface is used in a chair, a wheelchair, a plane, a bicycle, a motorcycle, a train, an automobile, a bus, or a mattress topper.

In another embodiment of the present invention, the system includes a pump for pumping the gas and/or liquid.

In another embodiment of the present invention, the system includes a vacuum system for the gas and/or liquid.

In another embodiment of the present invention, the housing is configured to support a human foot.

In another embodiment of the present invention, the system is integral to footwear.

In another embodiment of the present invention, the system is integral to a helmet.

In another embodiment of the present invention, the system is integral to a gripping device.

In another embodiment of the present invention, at least a portion of the housing is elastic.

In another embodiment of the present invention, at least some of the particles are fibers.

In another embodiment of the present invention, each of the at least two partitions are filled with particles having different characteristics.

In another embodiment of the present invention, the system includes pre-shaped sections in the reservoir for retaining subsets of the particles having differing binding characteristics. Each of the sections is connected to an individual valve assembly for selectively controlling a flow of the gas and/or liquid thereto.

In another embodiment of the present invention, the system includes pre-shaped sections in the reservoir. A barrier between adjoining partitions permits the flow of the gas and/or liquid therethrough.

In another embodiment of the present invention, the housing includes a footwear insole.

In another embodiment of the present invention, the housing includes a footwear midsole.

In another embodiment of the present invention, the housing includes a deformable mold.

In another embodiment of the present invention, the housing includes an erasable mold.

In another embodiment of the present invention, the housing includes a midsole or an insole. The housing has built-in supports and is filled with the particles for capturing a plantar foot impression.

In another embodiment of the present invention, the particles are lubricated with a lubricant having a range of viscosities.

In another embodiment of the present invention, the particles have a Shore A hardness from about 10 to about 70.

In another embodiment of the present invention, the valve assembly has an end opening smaller than the particles.

In another embodiment of the present invention, the system includes a midsole cavity having a predetermined shape and support structure therein.

In another embodiment of the present invention, the system includes a midsole having a forward portion. The forward portion consists of about ⅓ of the midsole and has a lower cavity to limit an amount of particles distributed under a forefoot.

In another embodiment of the present invention, one or more areas of the housing are restricted from particle migration.

In another embodiment of the present invention, the housing includes an outlet for release of the gas and/or liquid.

In another embodiment of the present invention, the housing includes one or more holes to allow the gas and/or liquid to escape.

In another embodiment of the present invention, at least a portion of the particles are doped with a substance that can be fused together by applying an appropriately calibrated energy source.

In another embodiment of the present invention, the valve assembly has an end opening that includes a screen to prevent particles from entering the valve assembly.

In another embodiment of the present invention, the system includes an adhesive surface applied to the housing to reduce migration of the particles.

A method embodiment of the present invention for producing a custom support device includes disposing a subject item on a substantially air-tight housing that is partially filled with a plurality of particles and a gas and/or liquid, and removing at least a portion of the gas and/or liquid in the housing.

In another embodiment of the present invention, the method includes vibrating the housing.

A three-dimensional (3-D) capture system embodiment of the present invention includes a flexible housing defining a substantially airtight reservoir therein, a plurality of particles disposed in the reservoir, a volume of a gas and/or liquid disposed in the reservoir, a valve assembly in communication with the reservoir for regulating a quantity of gas and/or liquid in the reservoir, and vibrator for stimulating and distributing the particles to conform to a contour of a subject item.

A process embodiment of the present invention, for making a custom footwear from a positive foot contour, includes pre-loading loose particles into a midsole of the footwear, originating a vacuum line from within the footwear to a unidirectional air valve assembly terminating outside of the footwear, sealing the midsole airtight, placing a positive foot contour onto the midsole and pressing down firmly; and activating a vacuum system connected to the valve assembly to capture a form of the foot contour.

In another embodiment of the process of the present invention, at least a portion of the particles are fused together by an appropriately calibrated energy source.

In another embodiment of the process of the present invention, the energy source is selected from a heater and a microwave device.

A method embodiment of the present invention for producing a custom support device includes disposing a subject item on a substantially air-tight housing that is partially filled with a plurality of particles, and a gas and/or liquid, moving, forcibly, the subject item on a surface of the housing, and removing at least a portion of gas and/or liquid in response to the moving.

A midsole embodiment of the present invention for obtaining a contour impression, includes loose, distinct particles disposed in the midsole.

An insole embodiment of the present invention for obtaining a contour impression, includes loose, distinct particles disposed in the insole.

A three-dimensional (3-D) capture system embodiment of the present invention includes a flexible housing defining a substantially airtight reservoir therein, a plurality of particles disposed in the reservoir, and a gas and/or liquid disposed in the reservoir. The plurality of particles and the gas and/or liquid within the housing maintain a contour of a subject item forcibly placed on the housing.

In another embodiment of the present invention, the system includes a high viscosity substance to retain the plurality of particles in a substantially fixed position relative to one another.

In another embodiment of the present invention, the system includes a vibrator mechanism for stimulating the particles into a desired location.

A three-dimensional (3-D) capture system embodiment of the present invention includes a rigid or semi-rigid orthotic housing defining a substantially airtight reservoir therein, a plurality of particles disposed in the reservoir, a gas and/or liquid disposed in the reservoir, a valve assembly in communication with the reservoir for regulating a quantity of the gas and/or liquid disposed in the reservoir, and a vibrator for stimulating and distributing the particles to conform to a contour of a subject item.

A footwear device embodiment of the present invention includes a flexible housing defining a substantially airtight reservoir therein, a plurality of particles disposed in the reservoir, a gas and/or liquid disposed in the reservoir, a valve assembly in communication with the reservoir for regulating a quantity of the gas and/or liquid disposed in the reservoir, and a vibrator for stimulating and distributing the particles to conform to a contour of the footwear device to that of a subject item. The footwear device is a midsole or an insole.

In another embodiment of the footwear device of the present invention, the particles are beads and/or fibers.

A seating device embodiment of the present invention includes a flexible housing defining a substantially airtight reservoir therein, a plurality of particles disposed in the reservoir, a gas and/or liquid disposed in the reservoir, and a vacuum pump connected to the flexible housing for selectively removing at least a portion of the gas and/or liquid from the reservoir.

In another embodiment of the present invention, the seating device includes a valve in communication with the reservoir for selectively sealing a flow of the gas and/or liquid to/from the reservoir.

In another embodiment of the present invention, the seating device includes a controller for controlling operation of the vacuum pump.

In another embodiment of the seating device of the present invention, the controller includes a timer.

In another embodiment of the seating device of the present invention, the controller controls a direction of air flow for the vacuum pump.

In another embodiment of the seating device of the present invention, the controller causes the vacuum pump to reverse the direction of air flow.

In another embodiment of the seating device of the present invention, the controller controls the direction of airflow according to a programmed, predetermined sequence of vacuuming events.

In another embodiment of the seating device of the present invention, the controller controls the direction of airflow according to a manual input.

In another embodiment of the seating device of the present invention, the vacuum pump operates in response to a manual input.

In another embodiment of the present invention, the seating device includes a plurality of flexible housings connected to the vacuum pump.

In another embodiment of the present invention, the seating device includes a heat sensor. The controller causes the gas and/or liquid to flow into the housing when the heat sensor detects a temperature in the housing that exceeds a selected temperature.

A seating device embodiment of the present invention includes a flexible housing defining a substantially airtight reservoir therein, a plurality of particles disposed in the reservoir, a gas and/or liquid disposed in the reservoir, and a valve assembly connected to the flexible housing for selectively removing at least a portion of the gas and/or liquid from the reservoir.

In another embodiment of the seating device of the present invention, the valve assembly has an end opening that includes a screen to prevent particles from entering the valve assembly.

In another embodiment of the present invention, the seating device includes a valve in communication with the reservoir for selectively sealing a flow of the gas and/or liquid to/from the reservoir.

In another embodiment of the present invention, the seating device includes a controller for controlling operation of the valve system.

In another embodiment of the seating device of the present invention, the controller includes a timer.

In another embodiment of the seating device of the present invention, the valve system operates in response to a manual input.

In another embodiment of the present invention, the seating device includes a plurality of flexible housings connected to the valve system.

In another embodiment of the present invention, the seating device includes a heat sensor. The controller causes the gas and/or liquid to flow into the housing when the heat sensor detects a temperature in the housing that exceeds a selected temperature.

A three-dimensional (3-D) capture system embodiment of the present invention includes a flexible housing defining a substantially airtight reservoir therein, a plurality of particles disposed in the reservoir, and a liquid and/or gas disposed in the reservoir. At least a portion of the gas and/or liquid is selectively removed from the reservoir for capturing a 3-D impression of a subject item.

In another embodiment of the present invention, the 3-D capture system includes a midsole having an elevated air vacuum line in communication with the reservoir for permitting an escape of at least a portion of the gas and/or liquid from the reservoir in response to the subject item being disposed on the 3-D capture system.

In another embodiment of the 3-D capture system of the present invention, the gas and/or liquid is permitted to flow through the elevated air vacuum line in only one direction.

In another embodiment of the 3-D capture system of the present invention, the gas and/or liquid is permitted to flow through the elevated air vacuum line in both a forward and a reverse direction.

In another embodiment of the 3-D capture system of the present invention, the vacuum line is connected to a manual check valve for output of the gas and/or liquid, and an additional line for input of the gas and/or liquid.

In another embodiment of the 3-D capture system of the present invention, the 3-D capture system includes a flap integrated into the elevated air vacuum line to selectively permit gas and/or liquid to flow through the elevated air vacuum line.

In another embodiment of the 3-D capture system of the present invention, the 3-D capture system includes a seating device.

A footwear device embodiment of the present invention includes a flexible housing defining a substantially airtight reservoir therein, a plurality of particles disposed in the reservoir, a gas and/or liquid disposed in the reservoir, and a supplemental reservoir housing a supplemental gas and/or liquid supply therein. The gas and/or liquid is selectively removed from the reservoir and the supplemental reservoir provides at least a portion of the supplemental gas and/or liquid supply to the reservoir. The footwear device is a midsole or an insole.

In another embodiment of the present invention, the footwear device includes a supplemental gas and/or liquid disposed in the supplemental reservoir.

A gripping device embodiment of the present invention includes a flexible housing defining a substantially airtight reservoir therein, a plurality of particles disposed in the reservoir, a gas and/or liquid disposed in the reservoir, and a valve assembly in communication with the reservoir for regulating a quantity of the gas and/or liquid disposed in the reservoir.

In another embodiment of the gripping device of the present invention, the valve assembly includes a valve for permitting the removal of at least a portion of the gas and/or liquid disposed in the reservoir.

In another embodiment of the gripping device of the present invention, the valve assembly is connected to a vacuum.

In another embodiment of the present invention, the gripping device includes a layer of memory intensive material disposed about the housing.

In another embodiment of the gripping device of the present invention, the housing is disposed about a handle of an athletic tool.

In another embodiment of the gripping device of the present invention, the gripping device is adapted for use with a golf club, a baseball bat, a racquet, a pole, a steering wheel, a handlebar, a firearm handle, a power tool, or a hand tool.

In another embodiment of the gripping device of the present invention, the valve assembly has an end opening that includes a screen to prevent particles from entering the valve assembly.

A method embodiment of the present invention for producing a customized handle grip includes disposing a user's hand on a substantially air-tight housing that is partially filled with a plurality of particles, and a gas and/or liquid, applying pressure to the housing with the hand, and removing at least a portion of the gas and/or liquid in the housing.

In another embodiment of the present invention, the method includes removing the hand. A contour of the hand is retained on the housing.

In another embodiment of the present invention, the method includes vibrating the housing.

In another embodiment of the method of the present invention, removing at least a portion of the gas and/or liquid is accomplished by the pressure of the hand.

In another embodiment of the method of the present invention, removing at least a portion of the gas and/or liquid is accomplished at least by a vacuum pump.

DESCRIPTION OF THE INVENTION

Figure 1:
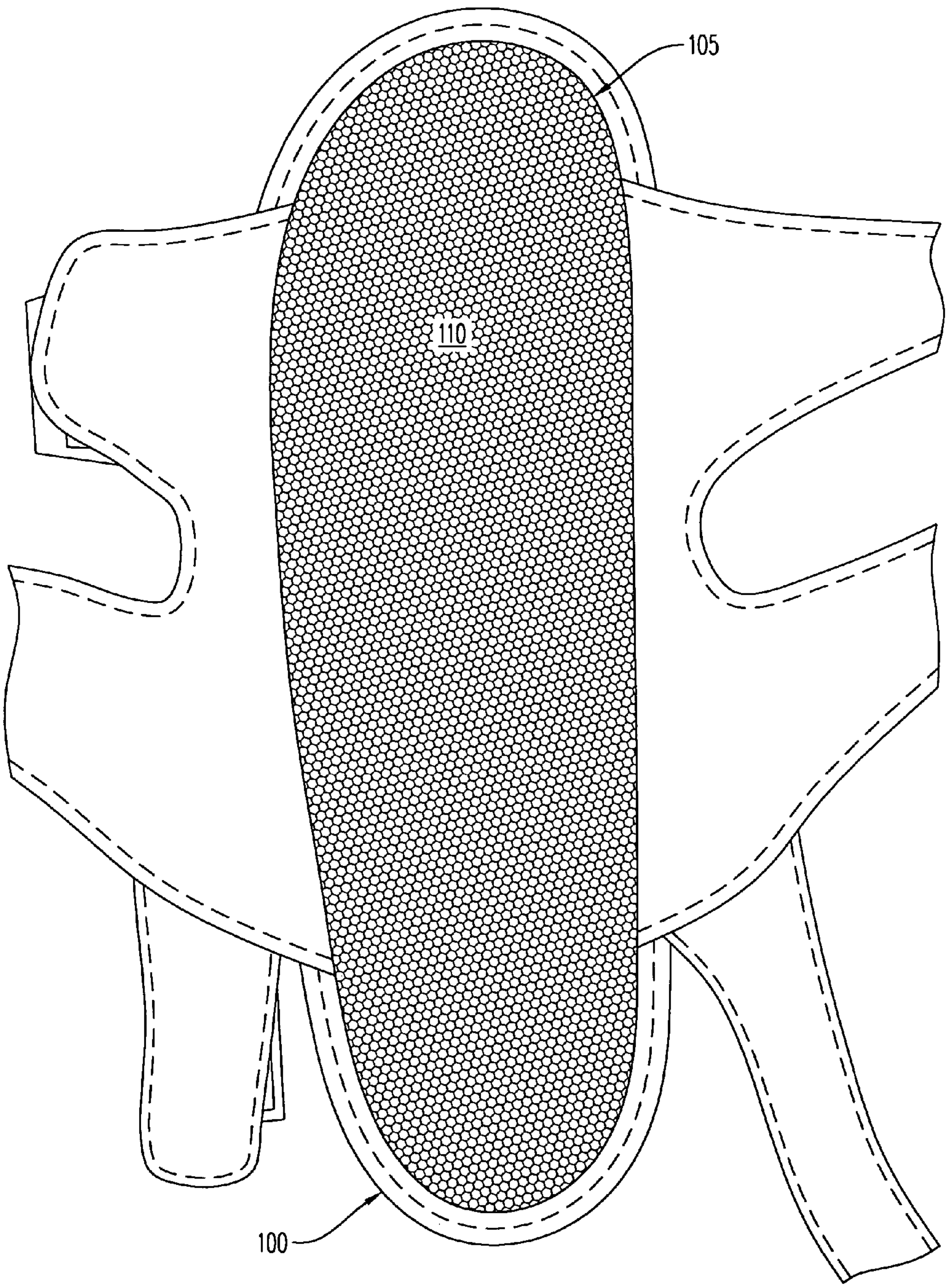
FIG. 1 is a top perspective view of an exemplary device, e.g., a sandal, including innnersole, i.e. insole, having beads disposed therein in accordance with the teachings herein.

A three dimensional capture system including a substantially air-tight housing is provided. The shape of the housing is preferably flexible and compatible with the size and shape of a subject item for which a 3-D contour is to be measured. The housing defines a reservoir therein. Loose particles and a gas and/or a liquid are disposed in the reservoir. A valve system is disposed in communication with the reservoir.

In the instance the housing has a sufficient volume of the air and/or liquid inside of the reservoir allowing free movement of the particles therein, the container can be bent, formed or shaped at will. In the instance the housing is bent, formed or otherwise has attained a desired shape, then all or most of the gas and/or liquid inside the reservoir is removed via the valve system. Removal of the gas and/or liquid from the reservoir forces the loose particles in the housing into close proximity to one another. This close proximity of the loose particles prevents easy, readily redistribution of the particles. The bent, formed or desired shape of the housing is retained in the form of a 3-D contour of the housing.

The embodiments disclosed in the drawings include devices that adapt to and support the plantar surface of a foot, devices that adapt to and support a user's posterior, and devices that adapt and conform to a user's grip. The depicted embodiments are illustrative of the invention and its application, but in no way should limit the scope of the invention's application. As noted in the background, this invention can be applied to many different contoured support applications.

The teachings of the present invention may be applied in numerous contexts but will be described primarily in the context of a footwear innersole or midsole. As such, a shoe is designed with a depth sufficient to accept a midsole that incorporates a substantially airtight housing of a size and shape sufficient to fill the interior bottom of the shoe. In the instance the systems of the present invention are included in devices intended to be gripped, the airtight housing is preferably sized to accommodate the hands of the user. The housing is preferably similar in size and shape to a sockliner commonly used in the footwear industry. The housing is preferably at least partially filled with loose, distinct particles.

The midsole may be a drop-in type that is fitted into the sole cavity of a shoe. Alternatively, the midsole may be permanently molded in or glued in the shoe. A drop-in midsole provides the advantage of easy replacement should the midsole fail.

Suitable particles compatible with the present teachings include elastomeric beads with a nominal diameter in the range of about 0.5 mm to about 4 mm. The amount of particles introduced into the container is a function of the amount of excess space that exists under the foot inside the shoe if the foot is removed from the shoe. This excess space inside the housing could be tailored to meet the support needs of, for example, the largest numbers of possible wearers of the shoe.

In accordance with the present invention, the particles may be fibers, not beads. The fibers are preferably numerous in quantity and conducive for facilitating the 3-D contour capturing of the present invention. It is to be understood that the fibers can be used in lieu of or in combination with the beads herein with respect to all of the disclosed embodiments, exemplary drawings, and claims. The fibers may be constructed of resilient material. An exemplary resilient material is rubber, which can be obtained, for example, from ground-up rubber tires. In another embodiment, the fibers may be dry, or coated with a lubricant or one or more coatings having specific properties. The coating or lubricant has, in one aspect hereof, a high viscosity characteristic. The holding power of the high viscosity lubricant or coating is such that when coated the fibers provide a still contour-holding contour mold of a subject object but not a firm (i.e., permanent) mold thereof.

Particles may be constructed of a variety of materials. Exemplary materials include urethanes, EVA, rubber, and various fibers.

FIG. 1 is a top perspective view of an exemplary device, e.g., a sandal 100, including an innnersole 105, also referred to as an insole, having beads 110 disposed therein in accordance with the teachings herein.

Figure 2:
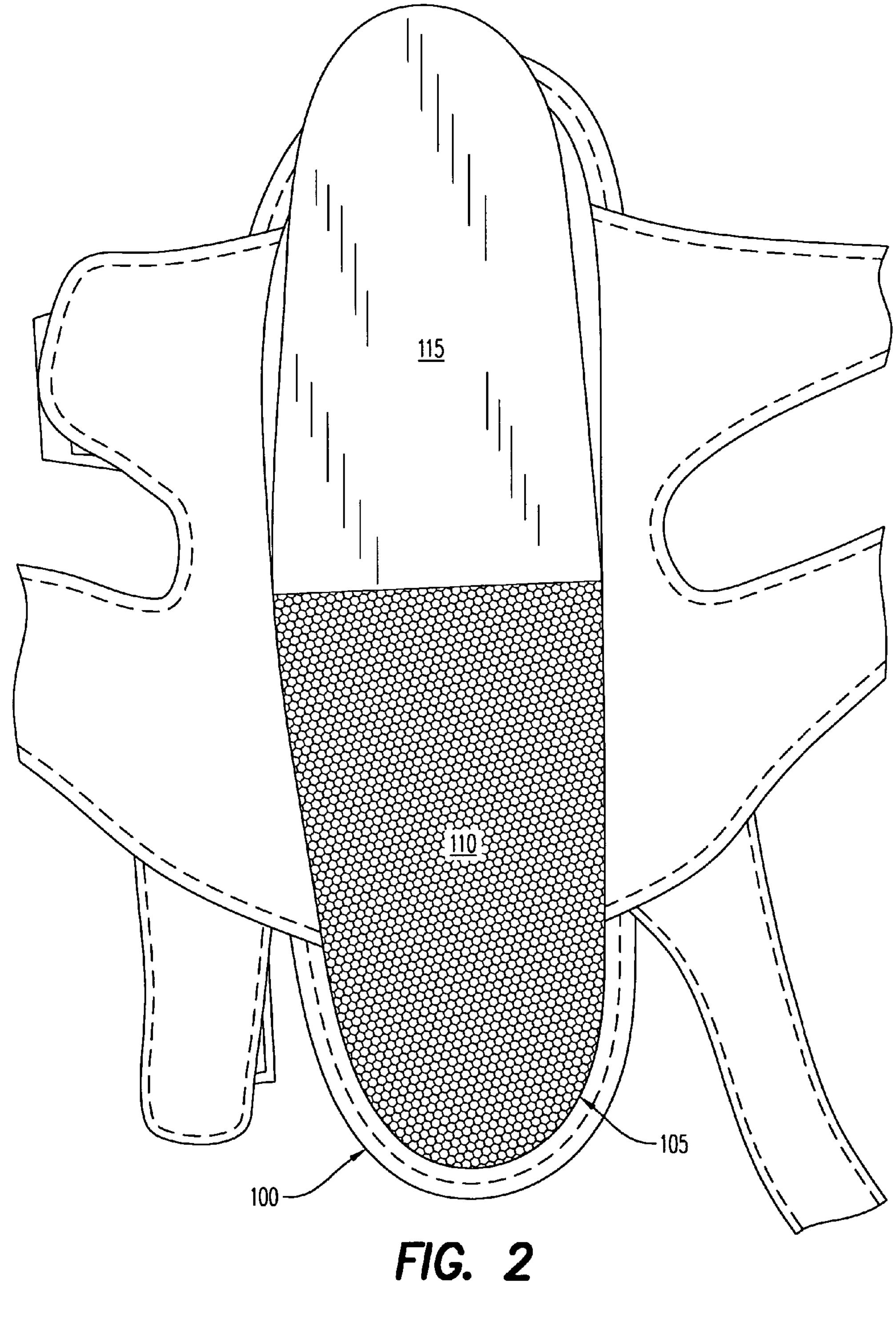
FIG. 2 is a top perspective view of the sandal of FIG. 1 wherein one-half of the innersole having beads disposed therein is exposed.

FIG. 2 is a top perspective view of sandal 100 of FIG. 1, wherein one-half of innersole 105 containing beads 110 disposed therein is exposed.

Figure 3:
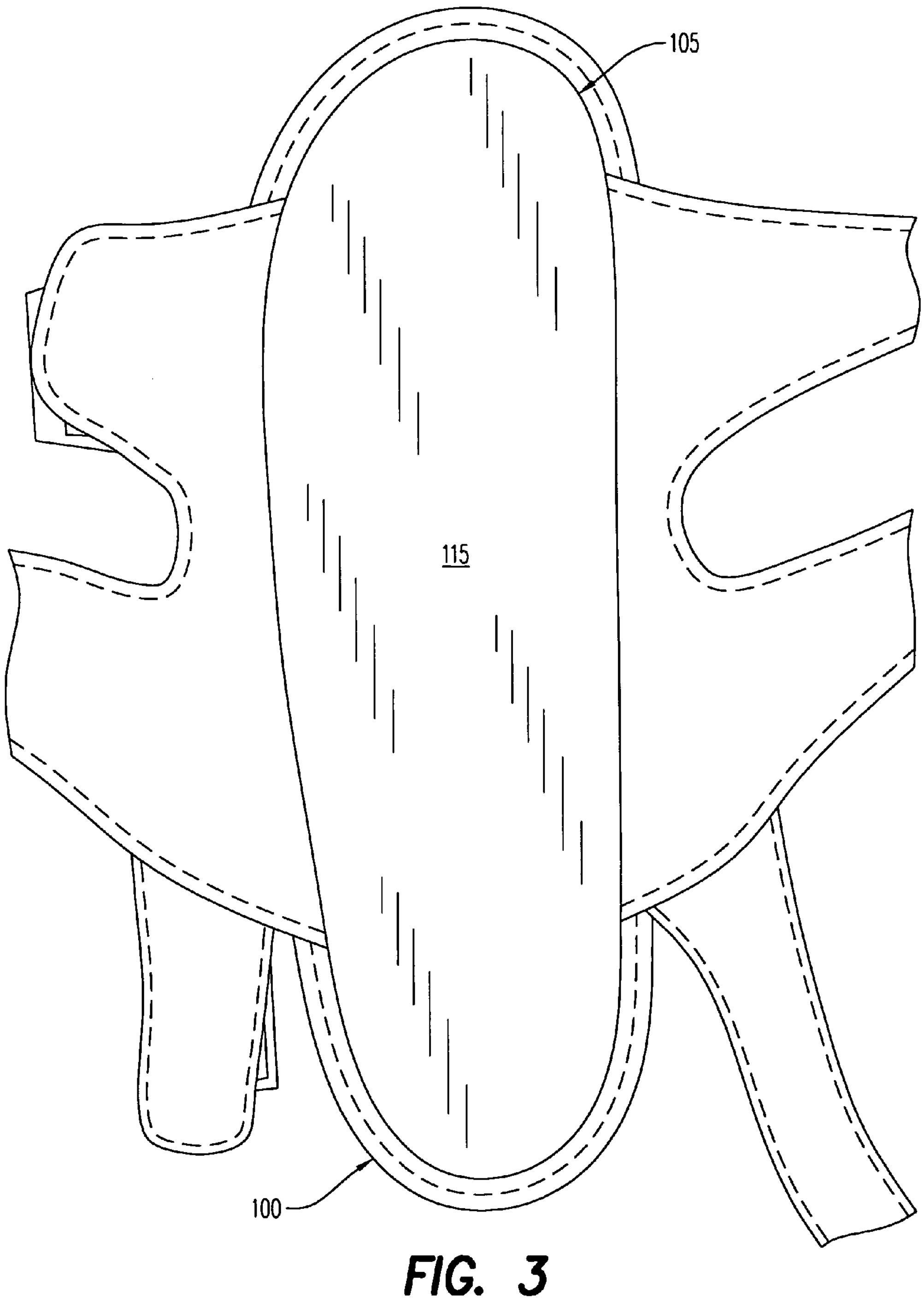
FIG. 3 is a top view of the sandal of FIG. 1 wherein the innersole and beads therein are sealed within a top liner.

FIG. 3 is a top view of sandal 100 of FIG. 1, wherein innersole 105 and beads 110 therein are sealed within a top liner 115.

Figure 4:
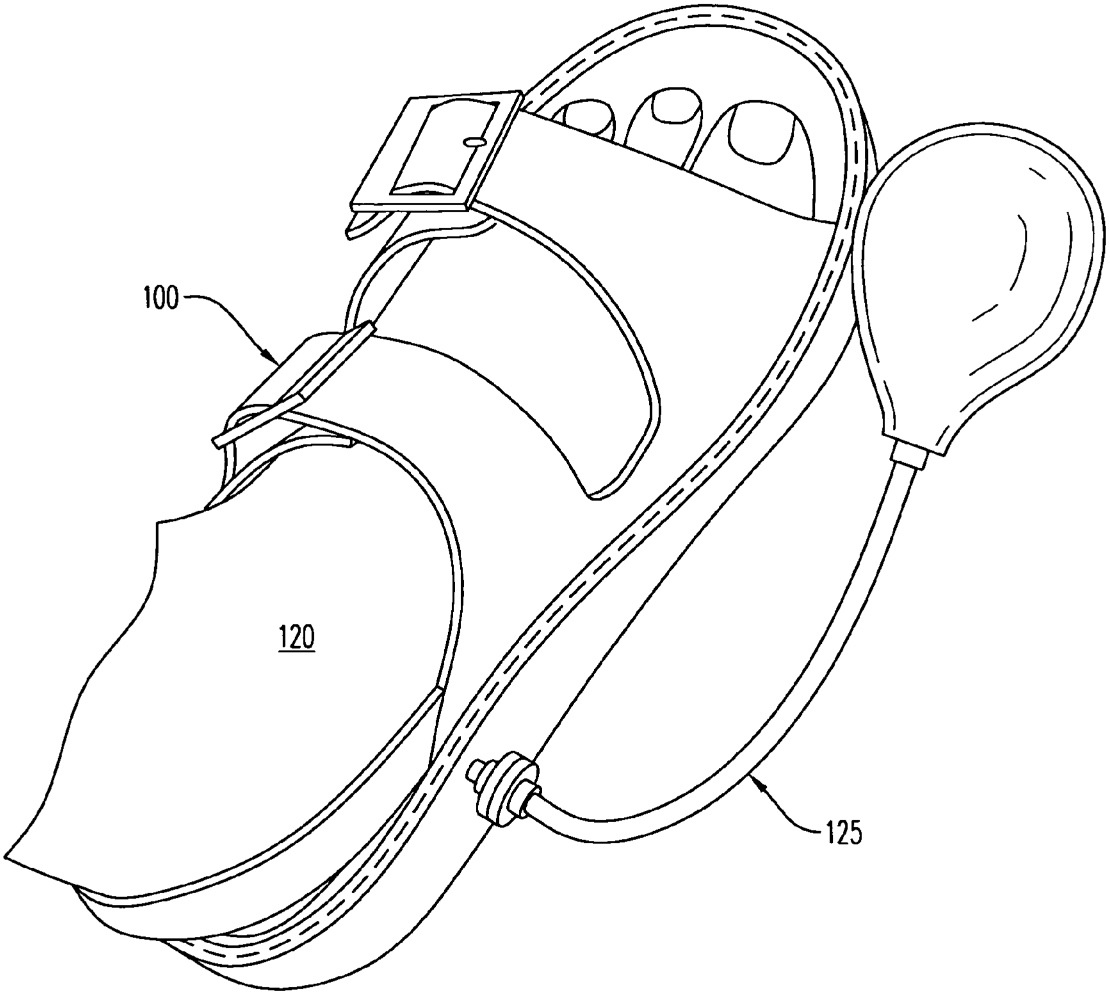
FIG. 4 is a top view of the sandal of FIG. 1 including a foot whose contour is to be measured and a gas removal system.

FIG. 4 is a top view of sandal 100 of FIG. 1, including a foot 120 whose contour is to be measured, and a gas removal system 125.

Figure 5:
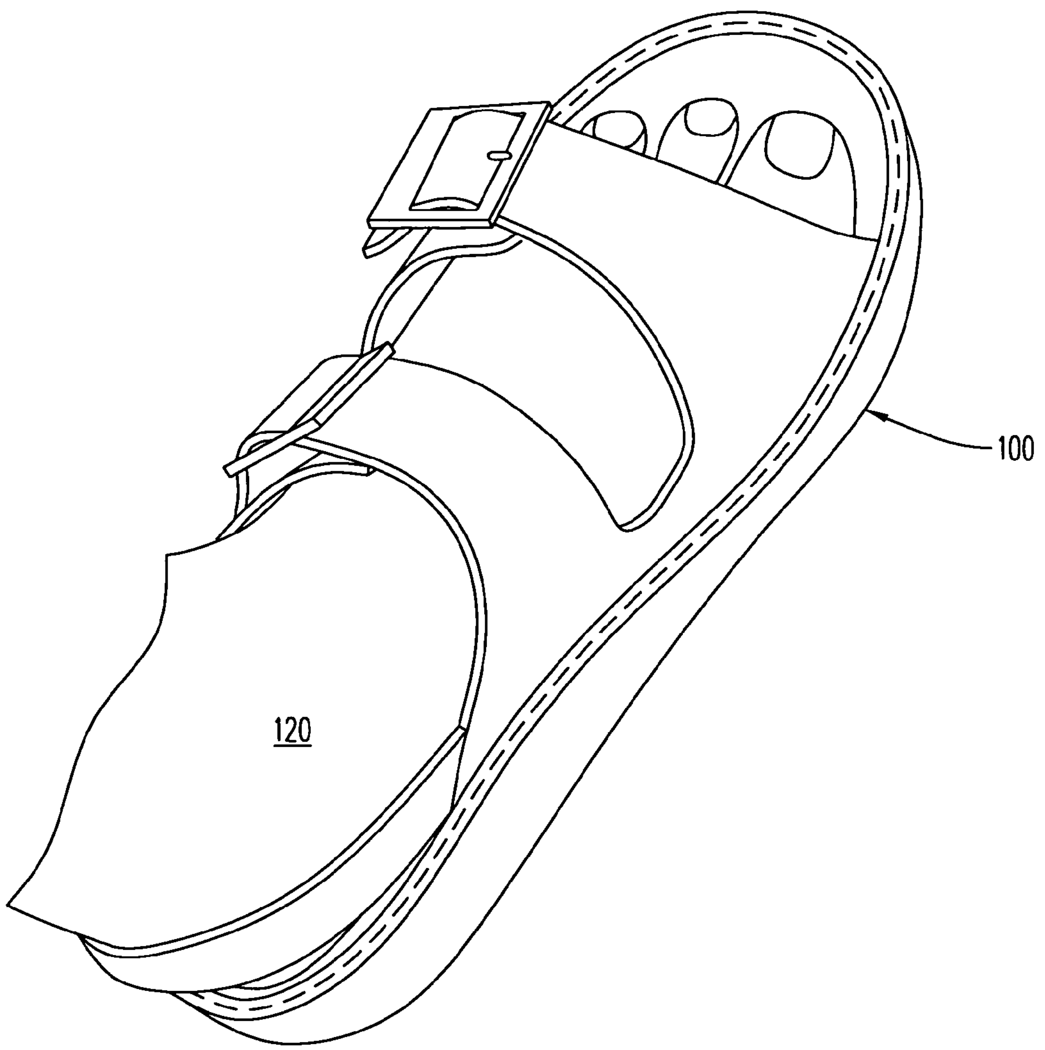
FIG. 5 is a top view of the sandal of FIG. 1 including a foot whose contour has been measured

FIG. 5 is a top view of sandal 100 of FIG. 1 including foot 120 whose contour has been measured.

Figure 6:
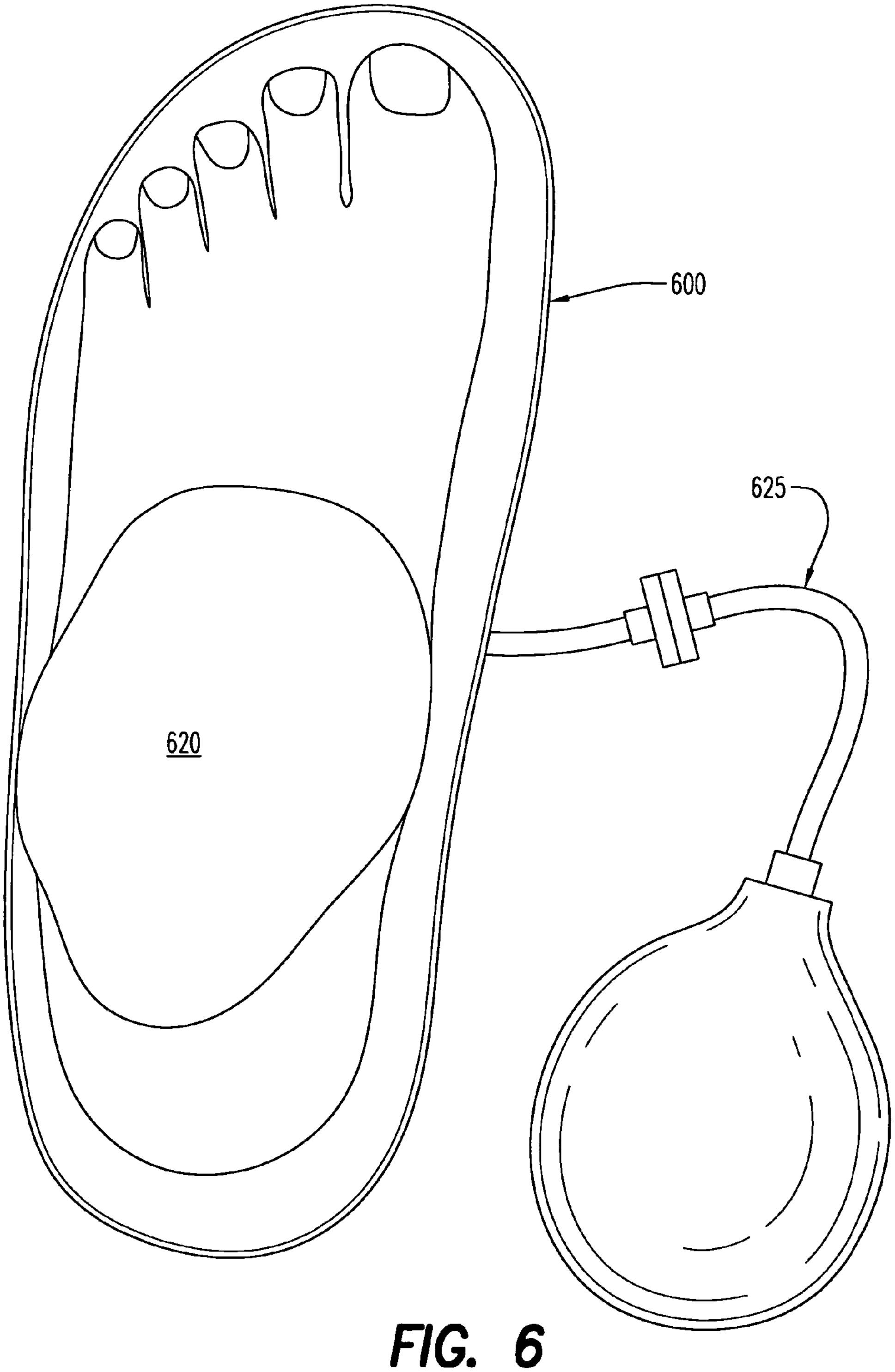
FIG. 6 is a top perspective view of an innersole in accordance with the teachings herein located on a vibrator.

FIG. 6 is a top perspective view of an innersole 600 in accordance with the teachings herein having a gas removal system 625, and a foot 620 thereon.

Figure 7:
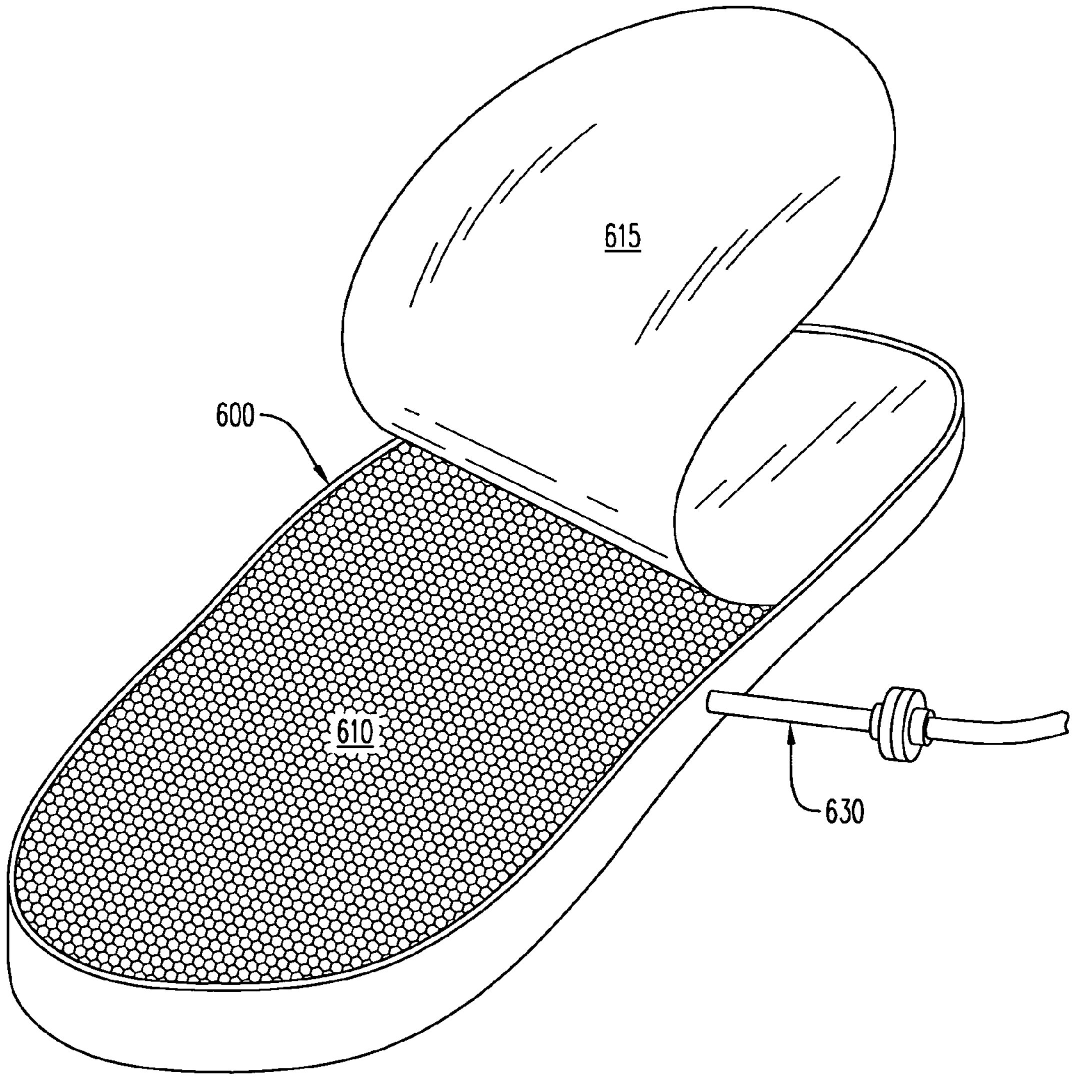
FIG. 7 is a perspective view of an innersole, in accordance with the teachings herein, showing the beads disposed therein partially exposed and a vacuum line attached.

FIG. 7 is a perspective view of innersole 600, in accordance with the teachings herein, showing beads 610 disposed therein partially exposed and an attached vacuum line 630. Also shown is top liner 615, which is partially removed from innersole 600.

Figure 8:
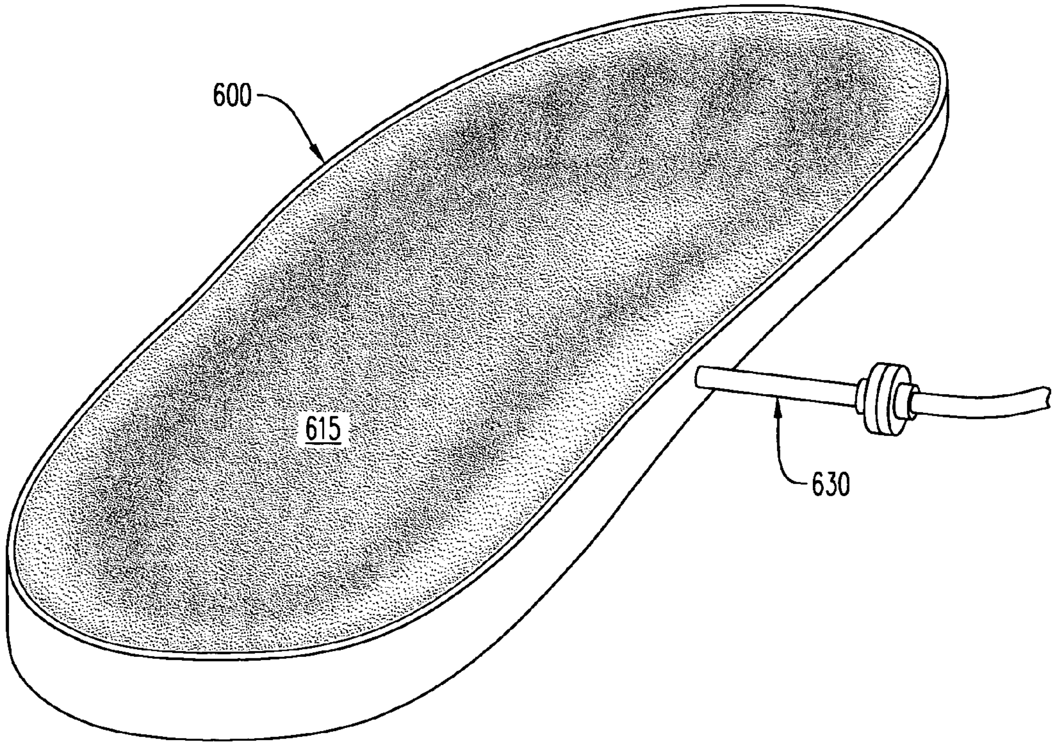
FIG. 8 is a top perspective view of an innersole having captured a 3-D contour therein, in accordance with the teachings herein.

FIG. 8 is a top perspective view of innersole 600 having vacuum line 630, which has captured a 3-D contour therein.

The substantially airtight housing can be laminated on at least one surface with a material suitable for contact with the foot. Such suitable materials can include, for example, specially treated leather, cloth or synthetic materials with similar properties.

In an aspect hereof, the reservoir defined in an interior of the housing has at least one one-way valve in communication therewith which allows for the flow of gas and/or liquid out of the substantially airtight reservoir. The unidirectional valve preferably has an air connector for connecting to a vacuum system for forcibly removing the gas and/or liquid from the housing.

In one aspect, the unidirectional valve includes a bypass capability so that air can be selectively re-introduced into the housing. In one aspect thereof, the gas and/or liquid is not reintroduced back into the housing.

In yet another aspect hereof, a blower or air introduction means may be provided to introduce or force air into the housing.

Operationally, the moldable innersole embodiment of the present invention (also referred to hereinafter as a "self customized insole") is disposed in the midsole of a shoe. The foot is introduced into the shoe and moved about a top surface of the housing containing the loose particles to force the particles contained therein to conform to the 3-D shape of the plantar surface of the foot. In an alternate method, the shoe, self-customized insole and foot are placed against a vibrating surface or a vibrator to assist in the migration of particles around the plantar surface of the foot to take on the 3-D contour thereof. Refer to FIGS. 9-15 to see a vibrator plate in accordance with the present teachings.

Figure 9:
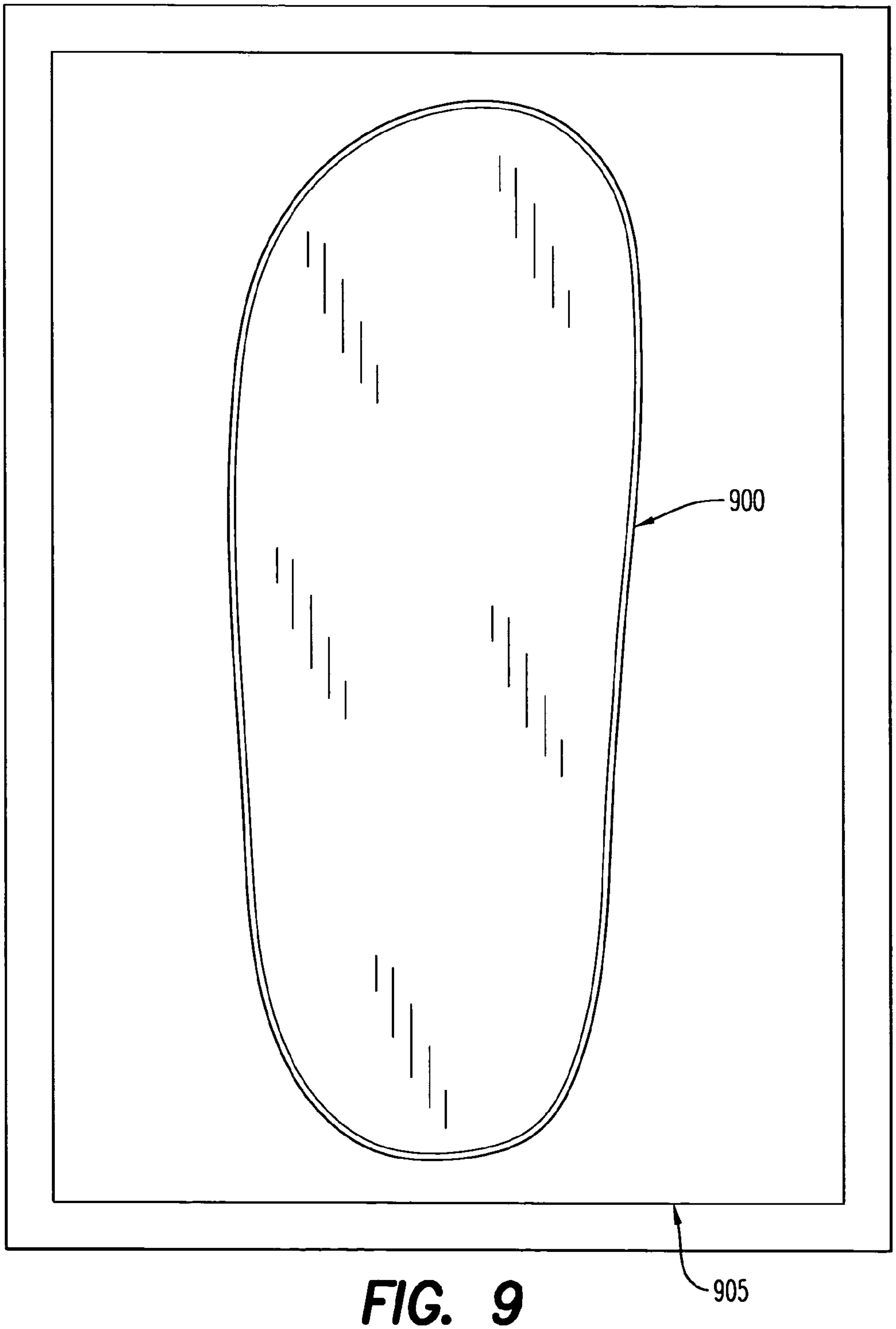
FIG. 9 is a top view of an innersole located on a vibrator, in accordance with the teachings herein.
Figure 10:
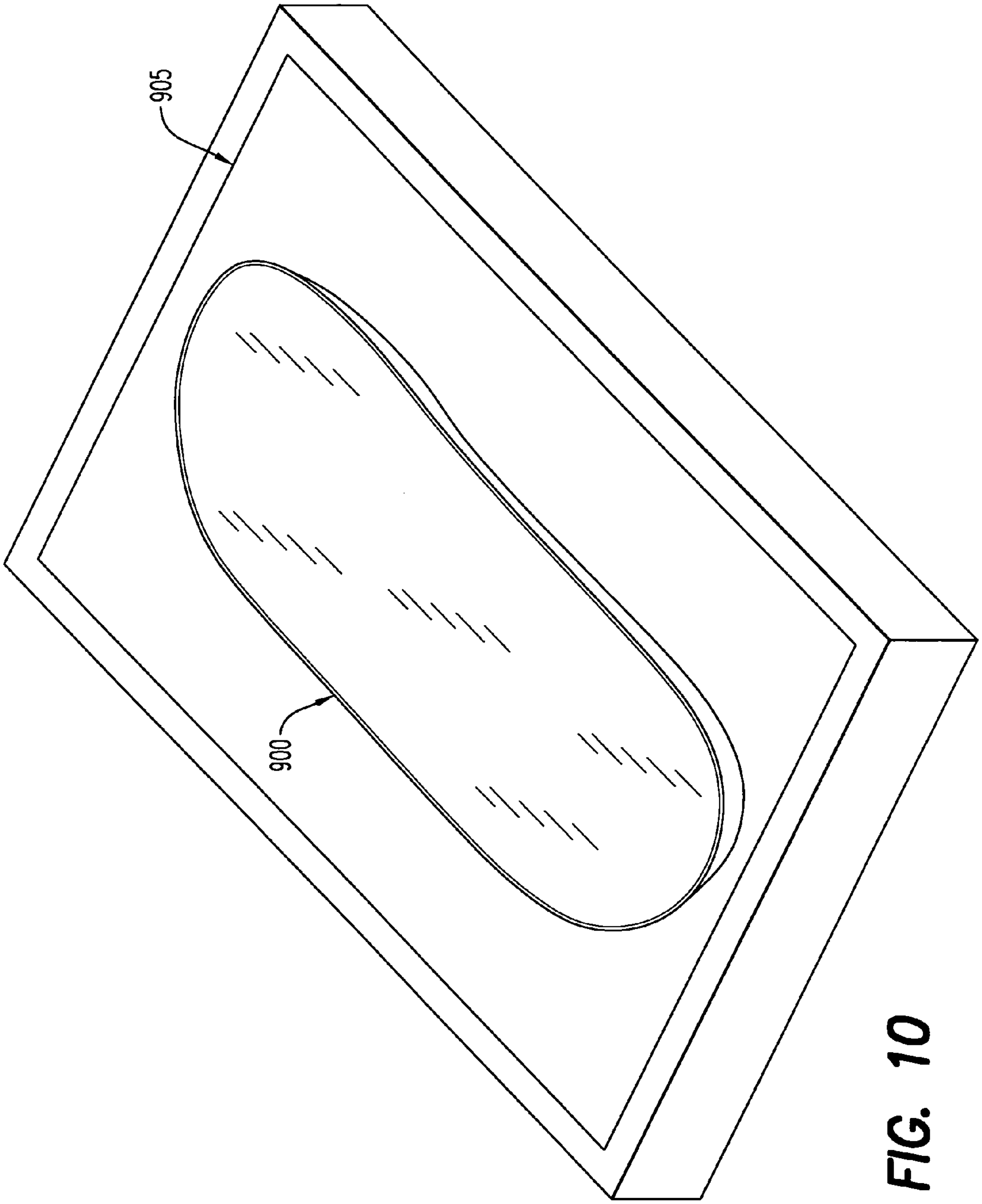
FIG. 10 is another view of an innersole located on a vibrator, in accordance with the teachings herein.

FIG. 9 is a top view of an innersole 900 located on a vibrator 905. FIG. 10 is another view of innersole 900 located on vibrator 905.

Figure 11:
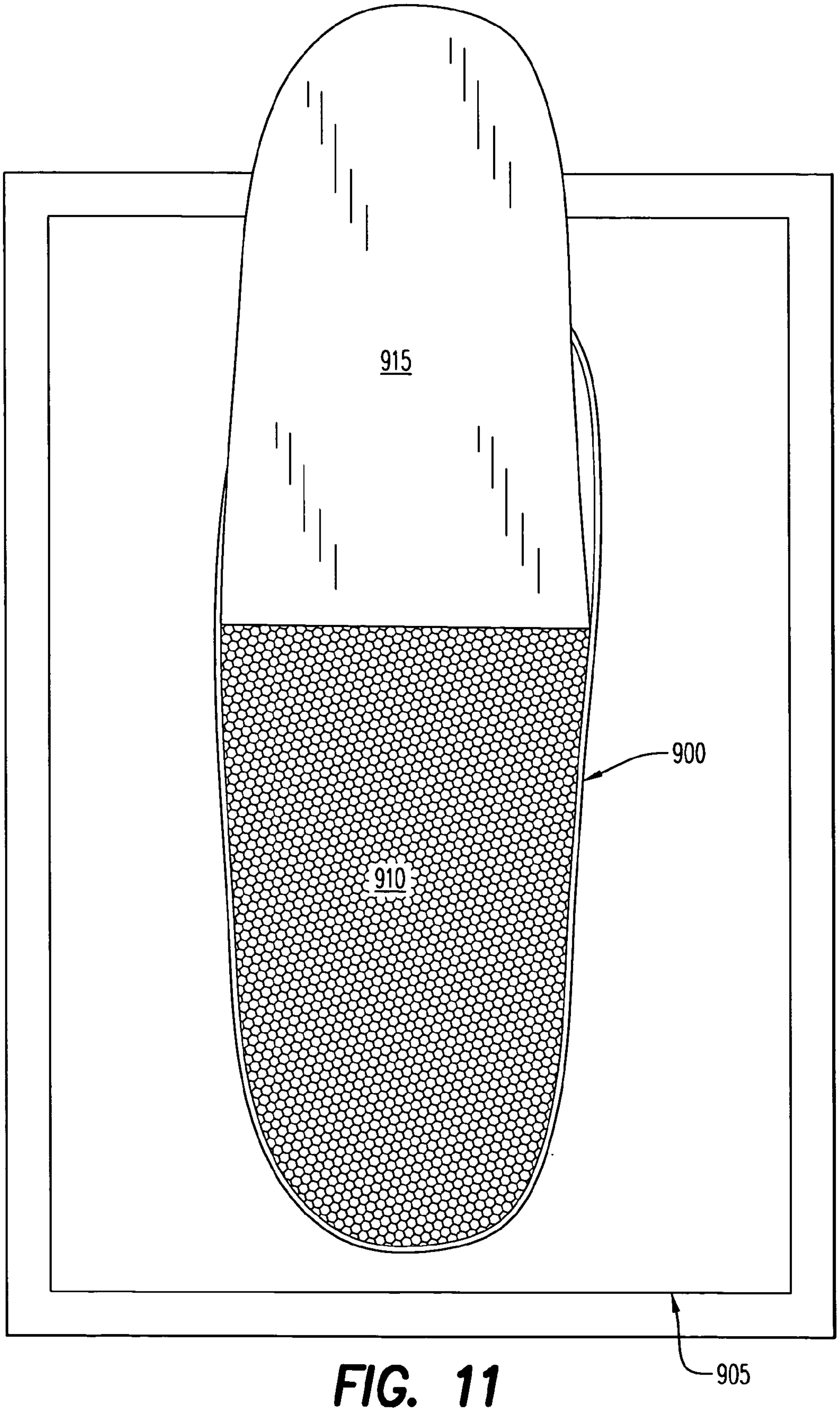
FIG. 11 is a top view of an innersole located on a vibrator and having exposed beads disposed in the innersole, in accordance with the teachings herein.

FIG. 11 is a top view of an innersole 900 located on vibrator 905 and having a top liner 915 partially removed to exposed beads 910 disposed in innersole 900.

Figure 12:
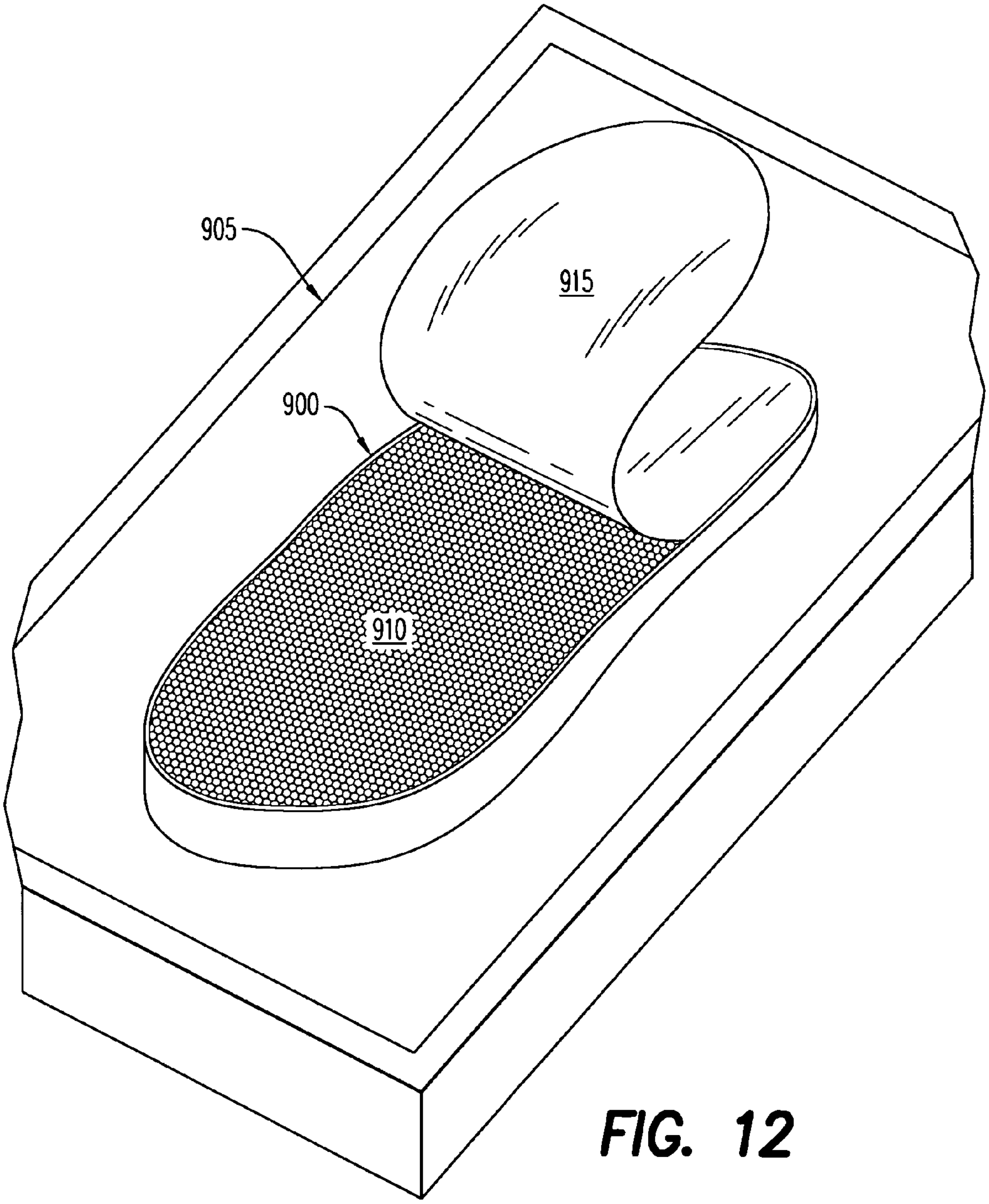
FIG. 12 is a side perspective view of an innersole located on a vibrator and having exposed beads disposed in the innersole, in accordance with the teachings herein.

FIG. 12 is a side perspective view of innersole 900 located on vibrator 905 and having exposed beads 910 disposed in innersole 900.

Figure 13:
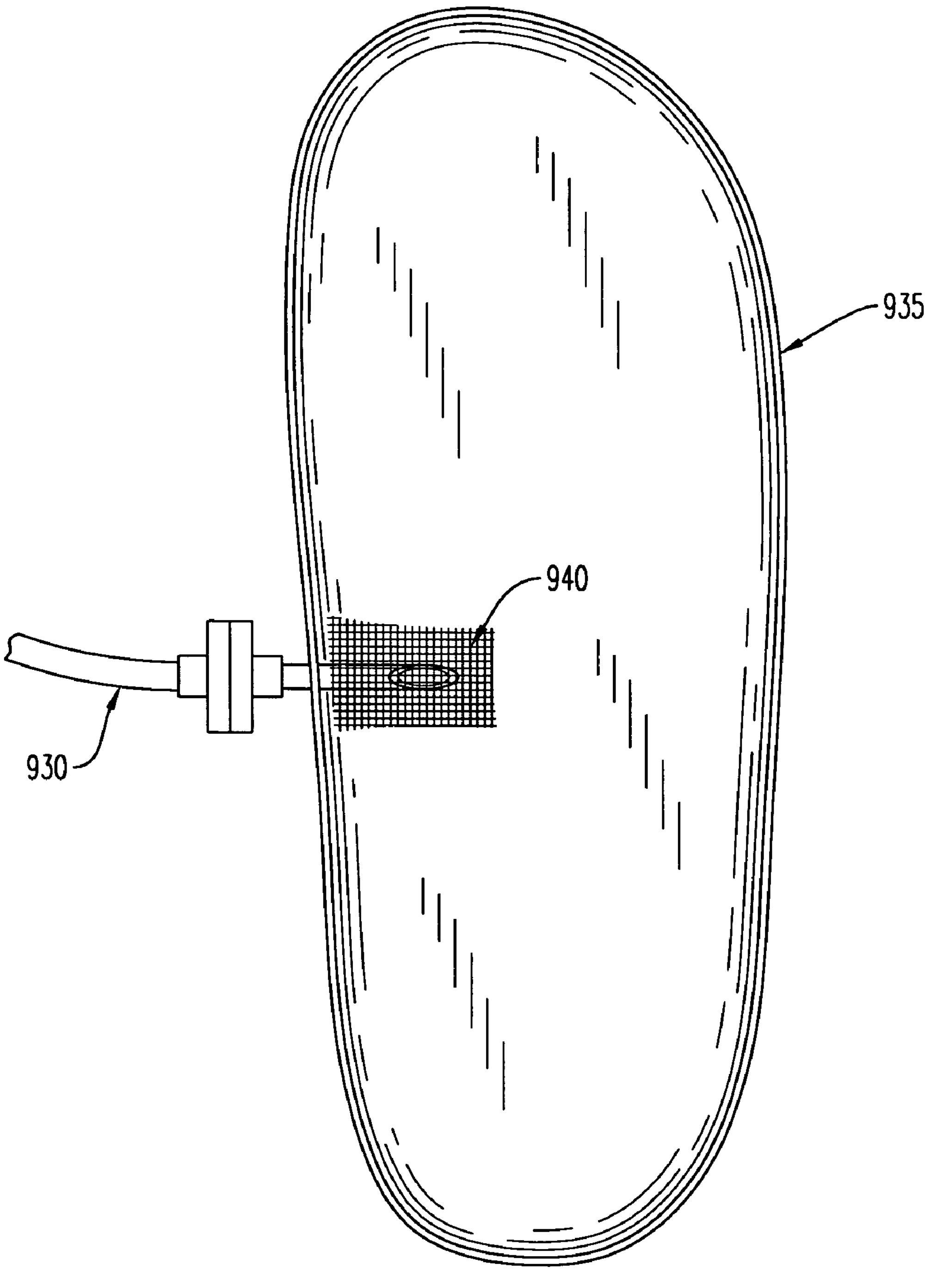
FIG. 13 is a top view of an exemplary vacuum line and associated filter disposed in an innersole.

FIG. 13 is a top view of an exemplary vacuum line 930 connected with an innersole housing 935. An associated filter 940, which is in the form of a screen or wire mesh, is disposed in innersole housing 935.

The excess of gas (e.g., air) and/or liquid is removed from the housing. The removal of the gas and/or liquid can be achieved in a number of methods as detailed below. If a unidirectional air valve in communication with the reservoir retaining the particles has a light pressure break-point, and with the flow direction of the unidirectional valve going from the housing to free air, then simply pressing the foot down will expel the majority of the air out of the housing.

A unidirectional air valve is used as discovered above and an air evacuation means is connected to the free air side of the unidirectional valve in another method. The air evacuation means is activated and the majority of the air removed from the container.

The valve may be a one-way check valve. The valve may also be a simple mechanical valve having a push-pull mechanism to manually open or close the valve. A secondary plug or stem may also be included and applied to the outlet of the check valve to prevent leaks. The plug is removable and is removed during resetting of the housing contour. A push-pull valve may be on the same line with a check valve to prevent leaking.

Another method of removing gas and/or liquid from the housing retaining the particles includes using a gas and/or liquid evacuation tool in conjunction with the unidirectional valve. The gas/liquid evacuation tool is connected to the unidirectional valve and activated, thereby removing substantially all of the gas and/or liquid from the housing. This method of gas/liquid removal is highly effective in retaining or locking the shape of the particles since the air evacuation is substantially complete, thereby restricting the free motion of particles.

Once the shape is captured, it may be desirable to retain or lock that shape permanently. A number of methods are disclosed to realize this feature. For example, the action of walking on the self customizing insole will, by virtue of the force applied by the foot upon the contoured surface force any excess air out of the unidirectional air valve incorporated into the insole with each step. This method has the advantage of being a passive or automatic feature. It will also be tolerant of slight leaks in the container. In addition, use of an airtight plug may also help to prevent leaks and typically will help to retain the contour for periods on the order of weeks. It may not be, however, perfect at retaining the shape over a long term. Particles may migrate due to the less than perfect vacuum inside the container.

According to another exemplary method, an adhesive material is used to retain the captured shape. During the manufacture (or subsequent thereto) of the particles, the particles are doped with an adhesive that is activated once the shape is retained to cause the particles to bind solidly together. The adhesive may be activated by a number of methods including, but not limited to, heat, radio frequency (RF) energy, ultraviolet (UV) energy or a captive catalyst, etc. Regarding the catalyst, a polyurethane or other materials may be used and activated for adhering the particles in a locked position.

According to yet another method for retaining or locking the 3-D shape, melting of at least some of the particles is used. Subsequent to forming the housing to the desired shape and removing excess air to retain the shape, heat is applied thereto, causing the particles to melt sufficiently to bond to one another. This heating can be radiant, ambient, electromagnetic or radio frequency in nature.

In one aspect of the present teachings it may be desirable to return the housing that has captured a 3-D contour to its original, quiescent state. This goal may be especially true for seating or sleeping surface applications, where different individuals may use the same surface. In the case of seating a completely automatic customized seating can be realized using the following embodiment of the invention.

The housing is designed sufficiently sized and shaped to approximate the size and shape of a seating surface. The housing defines a reservoir in an interior thereof for containing loose, discrete particles. There is also included at least a simple on/off valve to control the flow of a gas and/or a liquid into or out of the reservoir. In one aspect hereof, elastomeric beads are used to substantially fill the container. A subject item (e.g., a posterior surface of a person) is placed on the housing to re-distribute the particles in the housing such that the contour of the subject item is captured by the particles.

Optionally, air or liquid may be introduced into the container to unload the particles. Optionally, air or liquid may be circulated inside the container when so unloaded to assist in the free motion of the particles. Optionally, a vibrating action may be used in conjunction with, or in place of pressurization to assist in the free motion of the particles.

Once the desired shape is achieved by the housing and particles, all or part of the gas and/or liquid is removed from the reservoir. The removal of the gas/liquid may be accomplished passively or actively. If passive, a unidirectional air valve is used to allow for the expulsion of excess gas/liquid out of the reservoir. The liquid/gas is expelled due to the force applied by the subject item to the housing. The removal of the gas/liquid forces the particles into close proximity with each other, resulting in a captured 3-D contour that is resistant to movement.

If the gas/liquid is removed via an active process, an air or liquid removal pump is applied to the housing, in communication with the particle retaining reservoir. A unidirectional valve or an on/off valve may be used to prevent the undesired re-introduction of gas or liquid removed therefrom.

To return the housing to its original state, air or liquid must be reintroduced, in a sufficient volume, to allow for free movement of the particles.

In yet another aspect hereof, it may be desirable to allow for the circulation of gas and/or liquid in the reservoir (under a support surface) after the 3-D contour is fully captured. In the instance the particles are adhered to each other in the captured 3-D contour (by adhesives, melting, etc.), a volume of gas and/or liquid is allowed to flow back into and out of the container freely. This would allow, for example, a cooling effect as the subject foot walks in gait.

In an aspect hereof, more than one type of loose particle material can be retained in a common housing. For instance, different particles may be used because of the molding characteristics thereof, for instance.

In an alternate embodiment, the housing can be divided into more than one contained compartments or sections. Each compartment may have tailored characteristics for various regions under the supported surface. Such characteristics may include limited size and shape of a supported area, different size, density, weight or hardness of particles or fibers, and differences in gas or liquid. Other characteristics of the sections may include types of coatings, particles or fibers, differences in the ability to introduce or expel gas and/or liquid, and differences in the ability to introduce or expel particles and/or doping materials.

Figure 14:
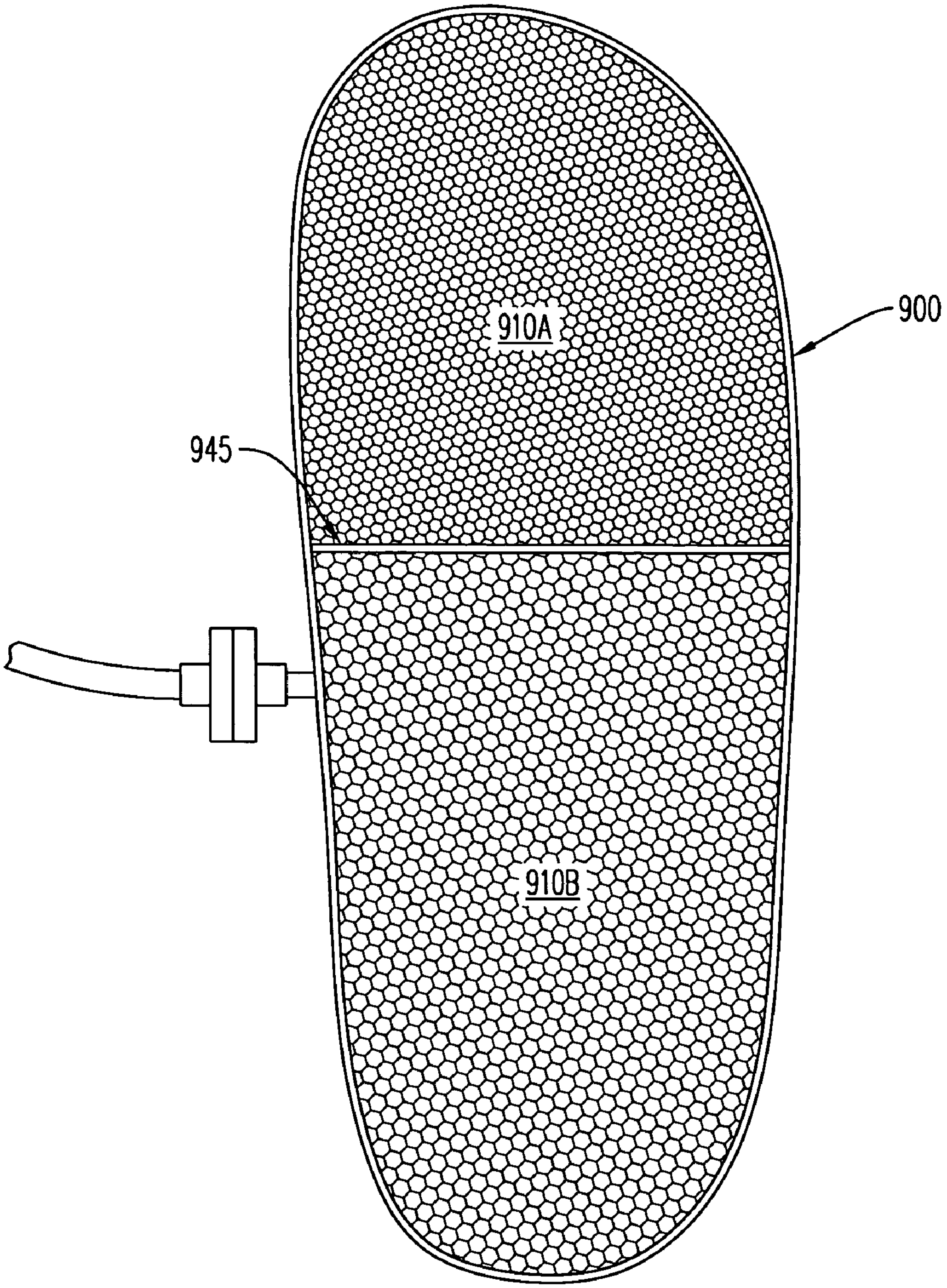
FIG. 14 is a top view of an innersole having multiple types of beads disposed in the innersole thereof, the multiplicity of types of beads separated by a barrier.

Alternatively, the housing, and in particular the reservoir defined thereby, may be partitioned into a number of sections. The sections may be desired since one part of the housing will be used to permanently capture a 3-D contour while another section will remain free to have "free" particles circulating therein. To separate multiple partitions, at least one baffle can be disposed at the junction of particle partitions. This aspect of the present teachings is shown in FIG. 14, which shows a top view of innersole 900 having multiple types of beads 910A and 910B disposed in innersole 900, the multiplicity of types of beads separated by a barrier 945.

The baffle or barrier separating partitions/sections of particle-filled sections is preferably permeable to gas (i.e., air) and/or the liquid occupying a volume of the housing, yet blocks the particles and/or fibers. The baffle may be formed of any material capable of allowing air and/or liquid to pass therethrough without allowing the particles to pass. Such materials may be, but are not limited to, wire mesh, a membrane, a fabric, and a synthetic mesh.

Figure 15:
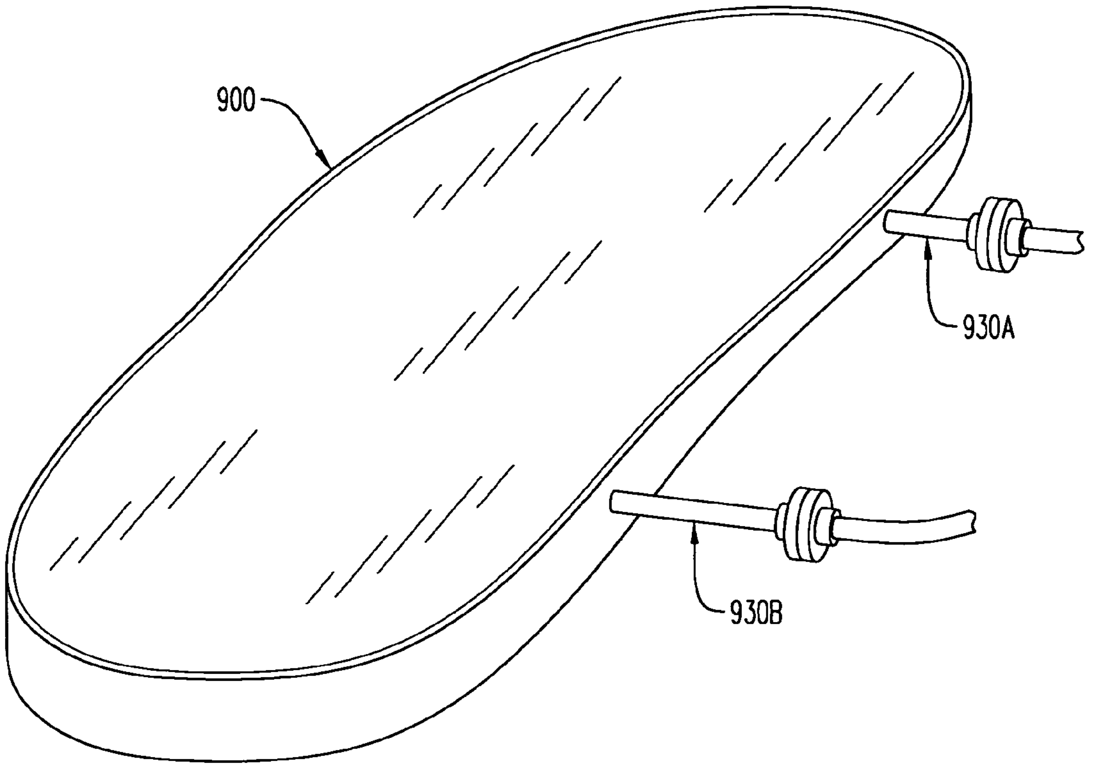
FIG. 15 is a side respective view of an innersole having multiple vacuum lines attached thereto, in accordance with the present teachings.

FIG. 15 is a side respective view of innersole 900 having multiple vacuum lines 930A and 930B attached thereto, in accordance with the present teachings.

The partitions may be provided to provided a predetermined contouring effect based on the shaped, size, and placement of the partitioned (i.e., compartmentalized) housing of particles. There may be numerous partitions within the housing in order to provide a highly flexible and highly customizable assembly wherein, for example, each (or at least a selective number) of the partitions or compartments are selectively vacuumed or vacuumed to a predetermined level.

In an aspect hereof, a number of holes are provided in an insole incorporating in the housing hereof. The holes, preferably small and located in an outer surface of the insole, provide an escape for air forced out of the insole by pressure from a foot. The holes are sized and located such that air is forced out therefrom when walking. The size and location of the holes do not, preferably, allow the full re-entry of the escaped air back into the insole during the course of normal walking. That is, the volume of air that is forced out during a walking step does not reenter the insole during the non-contact portions of walking.

In one aspect hereof, a selected section of particles in the housing are not in communication with a valve system that interfaces with a vacuum and/or pump for removing and inserting the gas or liquid, respectively.

In still another aspect of the present teachings, a covering such as a liner, may be attached to the housing containing the particles at the periphery of the liner. That is, the center majority is free to move above the housing due to the attachment only at the edges of the liner covering. The liner being separate from the majority of the housing provides for the migration of air into and out of the assembly. Air that becomes heated, for example in an actively worn shoe, can escape from the housing and the assembly of housing and liner covering through the liner. Further this aspect, the liner can be perforated to further facilitate the exchange of heated air.

It is also contemplated and within the scope of the present invention that the valve system or at least a portion thereof be located within a midsole/insole, outside the midsole/insole, or in the side wall of the midsole/insole and/or shoe side wall.

Key aspects of the present invention include, but are not limited to, a deformable mold, selective locking intensity by region of the housing, a combination of a solid material to the deformable material from heel to toe in certain shoe embodiments, unidirectional and controllable (i.e., open/closed) vacuum/pump lines, varying degrees of lubricant on the particles to vary and control the level of support offered by various embodiments of the device herein.

Figure 16:
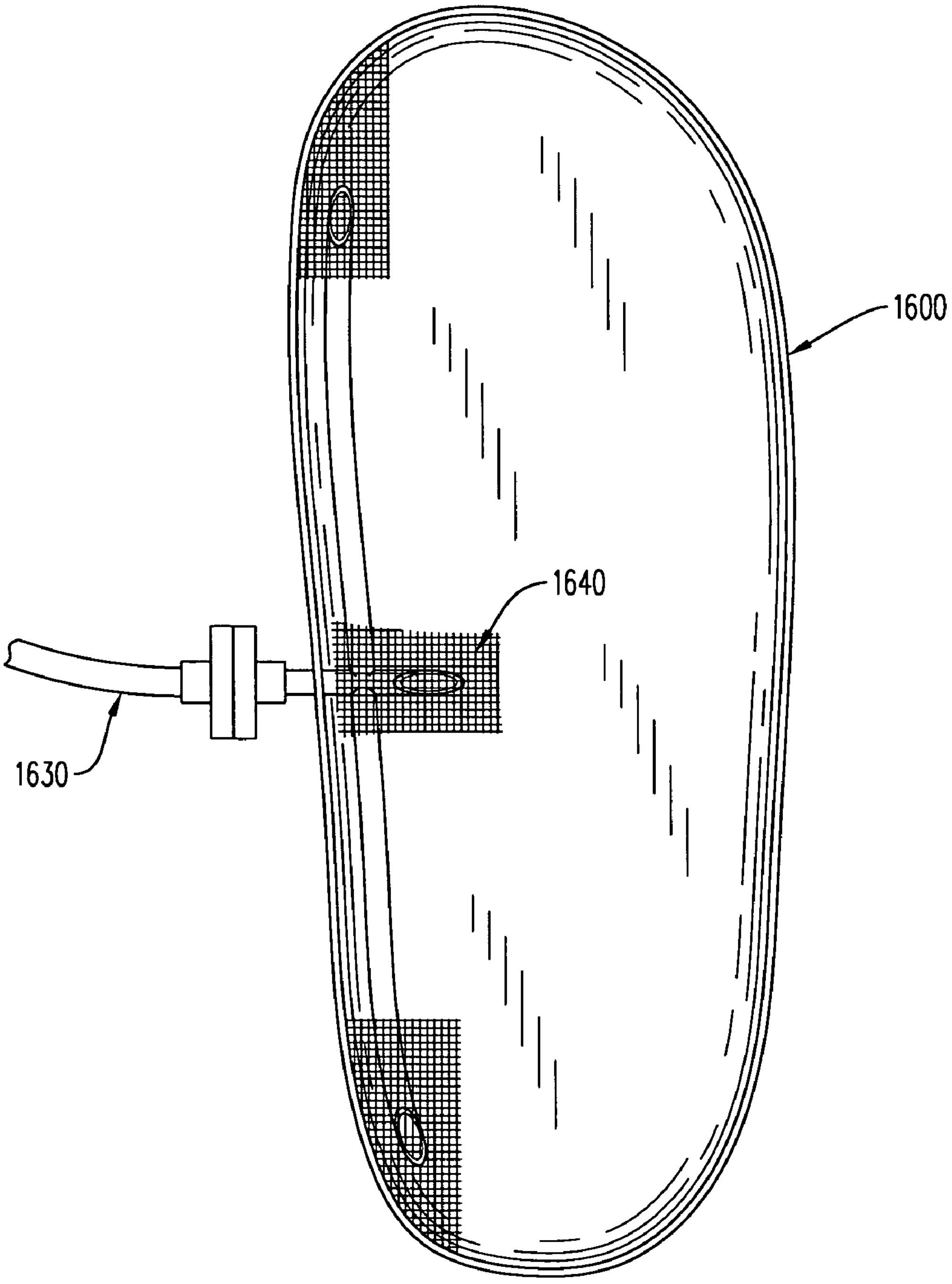
FIG. 16 illustrates a shoe midsole having a valve system comprising a multi-point distribution layout.
Figure 17:
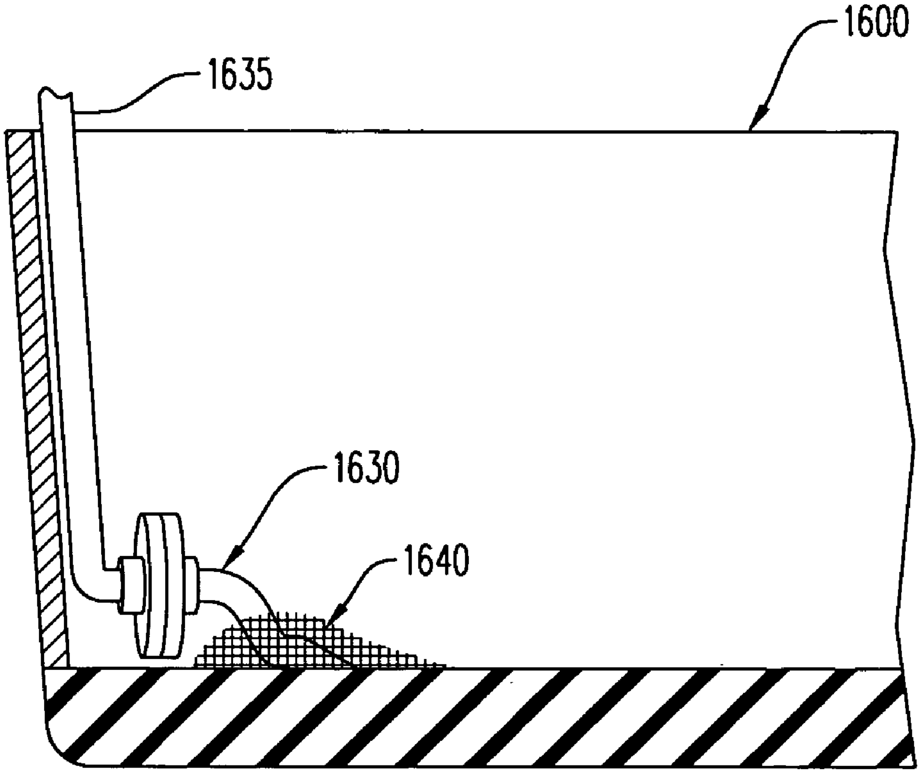
FIG. 17 discloses an elevational view of a midsole having an elevated air vacuum line to guard against foreign objects entering into the air vacuum line.

In another aspect hereof, the pump and vacuum systems that may be connected to the valve system are protected from damage and contamination, from either the particles and environmental concerns. As shown in FIG. 17, a midsole 1600 having an elevated air vacuum line 1635 to guard against foreign objects entering into air vacuum line 1635 is provided. As shown in FIG. 16, a screen material, such as, for example, a fabric, synthetic, or a metallic mesh 1640 can be disposed over the opening of the valve system and/or the pump/vacuum systems 1630.

In an aspect of the present teachings, RF sensitive particles may be disposed in the housing. The RF sensitive particles increase in temperature upon exposure to RF energy. The RF sensitive particles are re-activated and bond to each other and other components in contact therewith by being exposed to an appropriate source of RF energy.

Various materials may be used in combination with the present teachings to facilitate and improve the comfort to a user. Breathable materials, moisture-wicking materials and the like are within the scope herewith.

It one aspect hereof, the housing or a section therein may have the gas and/or liquid therein partially vacuumed or otherwise removed therefrom. That is, the removal of the gas and/or liquid need not be an all or nothing proposition. In fact, it may be beneficial to remove a certain percentage of the gas and/or liquid, for example 60%-70% by volume, to create a housing that is semi-rigid or form holding. In this manner, the contour of the subject object, e.g., a foot, will be substantially retained by the partially vacuum packed particles in the housing.

It is noted that the midsole or insole cavity of a footwear item can be pre-loaded under a partial vacuum. The same application of a partial vacuum can be extended to the implementation of an entire cavity or housing. In the context of footwear, the midsole insole comprising the housing with particles can be partially vacuumed to have a predetermined (i.e., generic) footprint contour. Upon use, the wearer's footprint would customize the midsole insole. One advantage offered by the implementation would be that the user's foot is guided to the proper fitting location.

In another aspect hereof, a two-third foot bed length particle filled insole may rest on top of a full foot bed length housing filled with particles or simply inside of a conventional shoe. Thus, customized cushioning and contouring can be obtained in only certain areas of the footwear in a specific, controlled manner as needed/desired.

In another embodiment, the particle filled housing may be disposed only under the heel, metatarsal heads and toes (i.e., forefoot) of the midsole of footwear. The particles disposed in the housing may be under a partial, complete or non-vacuumed configuration.

In an aspect hereof, the particles (e.g., beads) can act to absorb and/or dissipate shock impacts, such as though experienced when a walking foot strikes the ground.

Another embodiment in accordance with the present teachings includes a sock liner disposed inside of a shoe. The sock liner comprises a housing of particles as described in detail above. The particles may be under a complete or partial vacuum and/or disposed within partitions. The length of the liner may extend the full length of the shoe's foot bed or a portion thereof.

It is also noted that a high viscosity material such as a lubricant may optionally be applied to the particles configured in an insole or midsole as a measure of making the particles less prone to migrate about the housing and/or a partition therein. The same application of a lubricant to the particles can be extended to the implementation of an entire cavity or housing. In a preferred embodiment, the lubricant is a high viscosity fluid that is used to coat the particles. An example of a high viscosity material is a Teflon® lubricant.

Regarding the application of the present teachings to footwear, it is noted that the housing and quantity of particles disposed therein may be adapted to accommodate different types of feet such as, for example, those with a high arch, a low arch, and other characteristic formations. The high arch or low arch insole and/or midsole can be separately packaged for consumer and/or application use.

It is also considered herein that an impression of a subject object, for example a foot, may include a full impression of the subject object or an partial portion thereof such as a partial length impression of a foot impression.

In one aspect of the present invention, the valve system includes two valves (i.e., dual valves) operating as input and output valves for controlling the introduction and evacuation of the liquid and/or gas to and from, respectively, the flexible housing containing the reservoir of particles and gas and/or liquid. One valve operates to control the input or intake of gas and/or liquid. One valve operates to control the output or expulsion of the gas and/or liquid. The input and output valves of the dual valve system are preferably uni-directional (i.e., one-way) valve devices, or at least valve devices configured to operate in one direction. In an alternative, at least one of the dual valves may optionally be bi-directional valve devices operated to allow gas and/or liquid to flow in either direction, in accordance with the teachings of the dual valve system aspects hereof. For example, one embodiment may include a one-way check valve line to allow air to escape, and a dual valve that may be opened to allow air to re-enter the housing.

The dual valve system provides a useable 3-D contour capture system and method for selectively capturing a 3-D impression of the subject object. The dual valve system may be implemented in numerous embodiments for a variety of applications. Exemplary embodiments incorporating the dual valve system include, but are not limited to, a system and method for: a foot impression (e.g., shoe insoles, sandals, ski boots, work boots, orthotics, etc.); all types of footwear and shoes, a seat cushion/surface, optionally including a lower or lumbar back support; a sporting goods device (e.g., a golf club and racquet handle, archery bow, etc.); a tool handle; a firearm handle portion, a steering wheel cover; and etc.

The intake valve of the dual valve system can be selectively opened and closed to permit the flow of an amount of the gas and/or liquid into the flexible housing and the output valve can be selectively opened and closed to permit the flow of an amount of gas and/or liquid out of the flexible housing. For example, the intake vale may be opened or manipulated to introduce a desired volume of liquid and/or gas into the flexible housing. The subject object (e.g., foot or hand) can then be placed on the flexible housing and the outlet valve can be opened or manipulated to permit the forced expulsion of an amount of the liquid and/or gas from the flexible housing, thereby creating a 3-D impression of the subject object in the particles located in the flexible housing. The outlet valve can be closed or manipulated so that no additional liquid and/or gas can be expelled from the flexible housing once the 3-D impression of the subject object is captured. The 3-D impression will thus be captured or locked by the system having dual valves. The captured or locked 3-D impression may be used for further processing such as, for example, electronic and/or manual scanning, mechanical casting, etc.

In an aspect hereof, the outlet valve may be configured to continuously permit the expelling of gas and/or liquid while the shoe, grip handle, etc. including the dual valve system hereof is in use. Therefore, gas and/or liquid may continue to be expelled during use of the device to achieve a better, more customized 3-D impression. The outlet line connected to the outlet valve may also be plugged to prevent leakage.

In the event the 3-D impression is not acceptable (e.g., the 3-D impression contour is not fully and/or accurately captured due to user error), the input valve may be selectively opened or manipulated to allow an introduction of additional liquid and/or gas into the flexible housing, thereby un-doing or "erasing" the previously captured 3-D impression. Another (i.e., new) attempt to capture the 3-D impression of the subject object may be performed using the same system comprising the dual valve system.

In this manner, the dual valve system may be used, repeatedly if desired (i.e., reusable), to selectively capture the 3-D contour of the subject object. It is noted that repeated 3-D impressions performed by any one user provides a method of training the user in the process of taking the 3-D impression. Thus, the final 3-D impression locked into the 3-D contour system (and used for further processing) has an improved likelihood of being an accurate 3-D impression of the subject object.

Optionally, the dual valve system can be interfaced with a pump for the introduction and/or evacuation of the liquid and/or gas to and from, respectively, the flexible housing having the dual valve system.

In another aspect hereof, the inlet valve of the dual valve system (or other systems disclosed herein) may be allowed to be opened or manipulated so as to allow an additional volume of the liquid and/or gas to be introduced into the flexible housing once the subject object is remove therefrom. That is, the 3-D impression is not "locked" into the flexible housing. The 3-D impression is effectively "erased" once the subject object is removed from the flexible housing.

Figure 18:
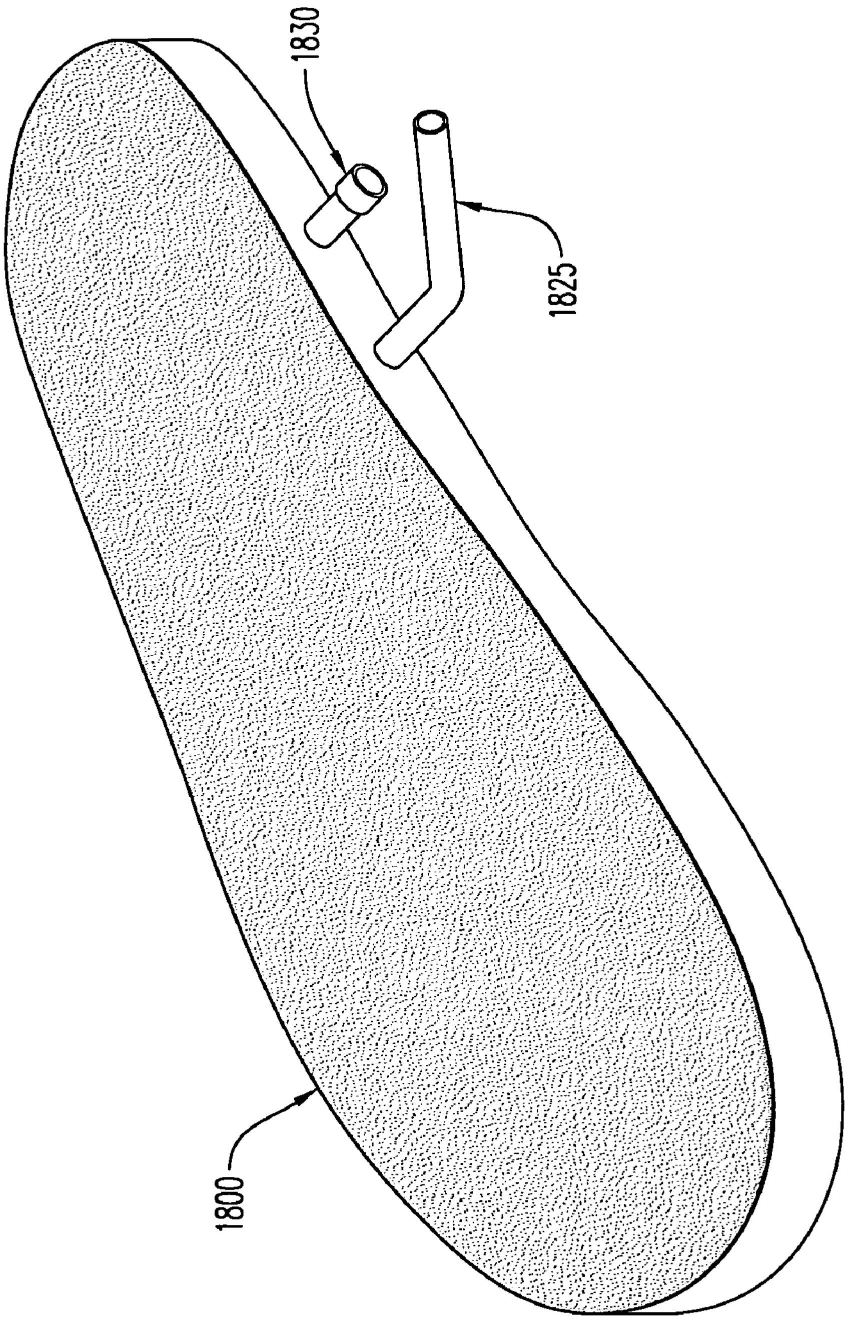
FIG. 18 depicts a perspective view of an exemplary insole having a dual valve system. Note that no 3-D impression is "locked" or captured by the insole.

FIG. 18 depicts a perspective view of an exemplary insole 1800 having a dual valve system. The dual valve system includes input valve 1825 and output valve 1830. Note that no 3-D impression is "locked" or captured by insole 1800.

Figure 19:
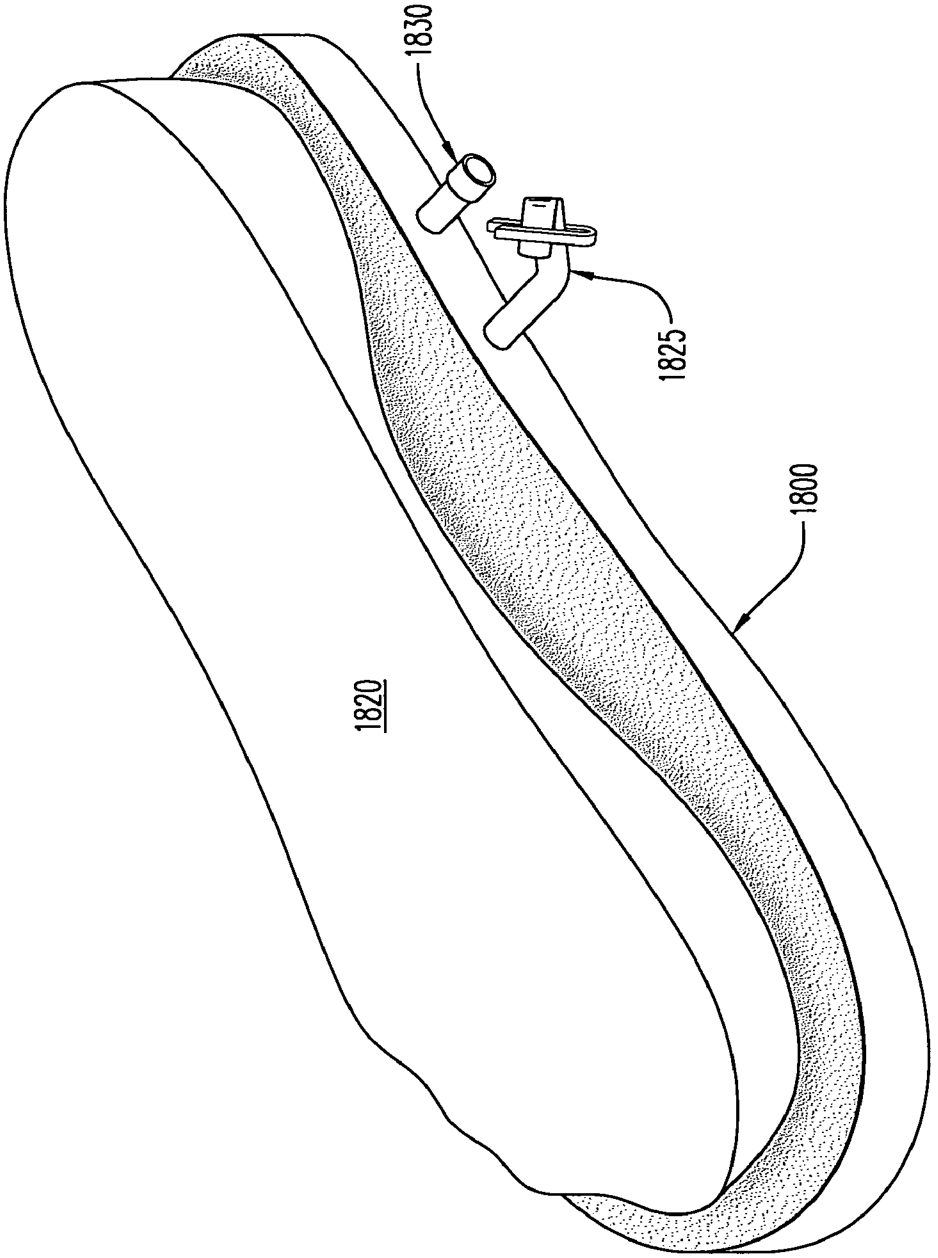
FIG. 19 depicts a perspective view of the exemplary insole of FIG. 18 with a 3-D impression of a foot captured or "locked" by the insole having the dual valve system.

FIG. 19 depicts a perspective view of the exemplary insole of FIG. 18 with a 3-D impression of a foot captured or "locked" by insole 1800 having the dual valve system. The dual valve system includes input valve 1825 and output valve 1830. A plaster cast obtained using the 3-D impression captured by the insole is shown on top of and mating with the captured 3-D impression.

Figure 20:
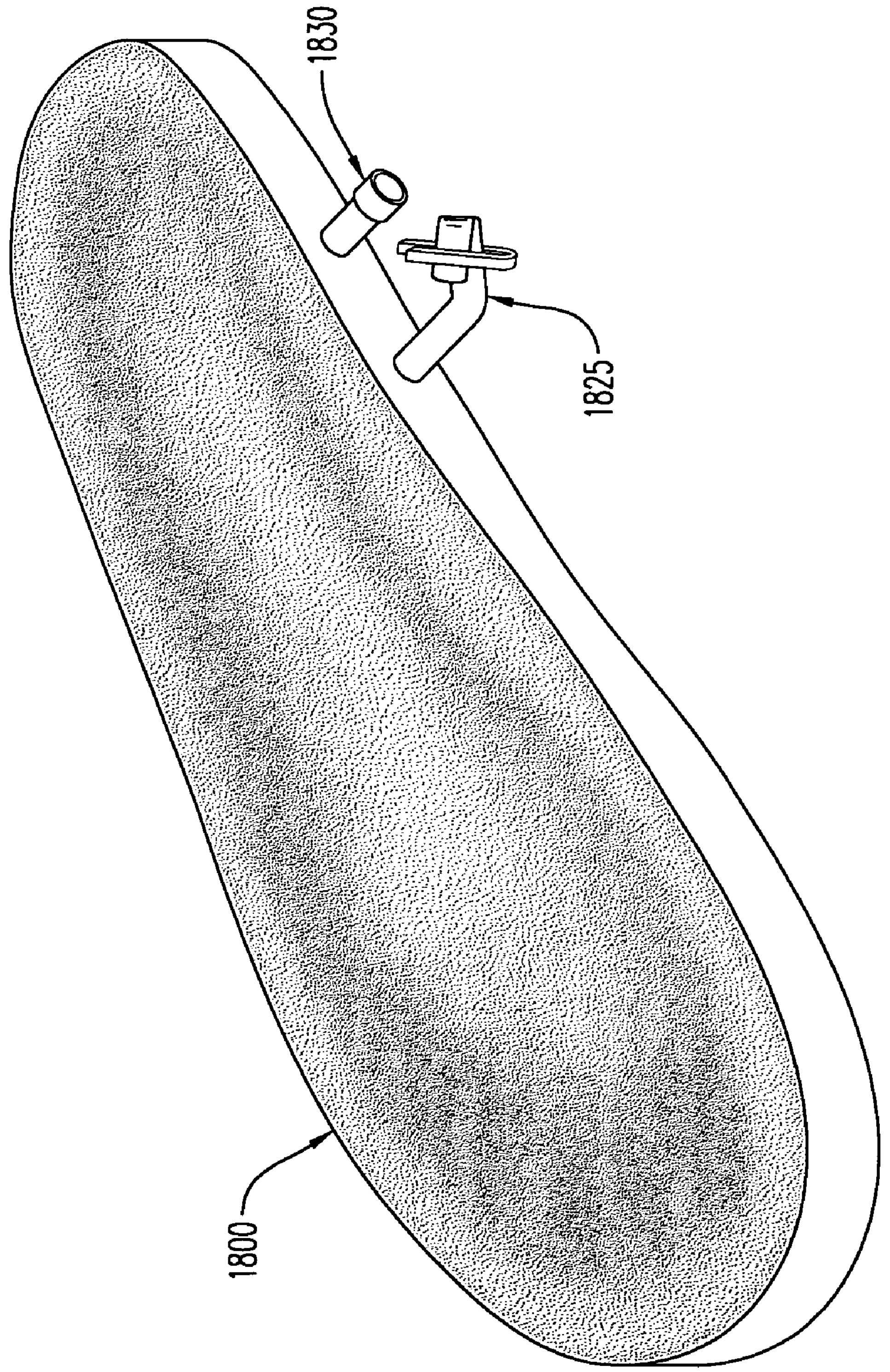
FIG. 20 is a perspective view of the exemplary insole with a 3-D impression of a foot captured or "locked" by the insole having the dual valve system.

FIG. 20 is a perspective view of the exemplary insole 1800 with a 3-D impression of a foot captured or "locked" by the insole having the dual valve system.

Figure 21:
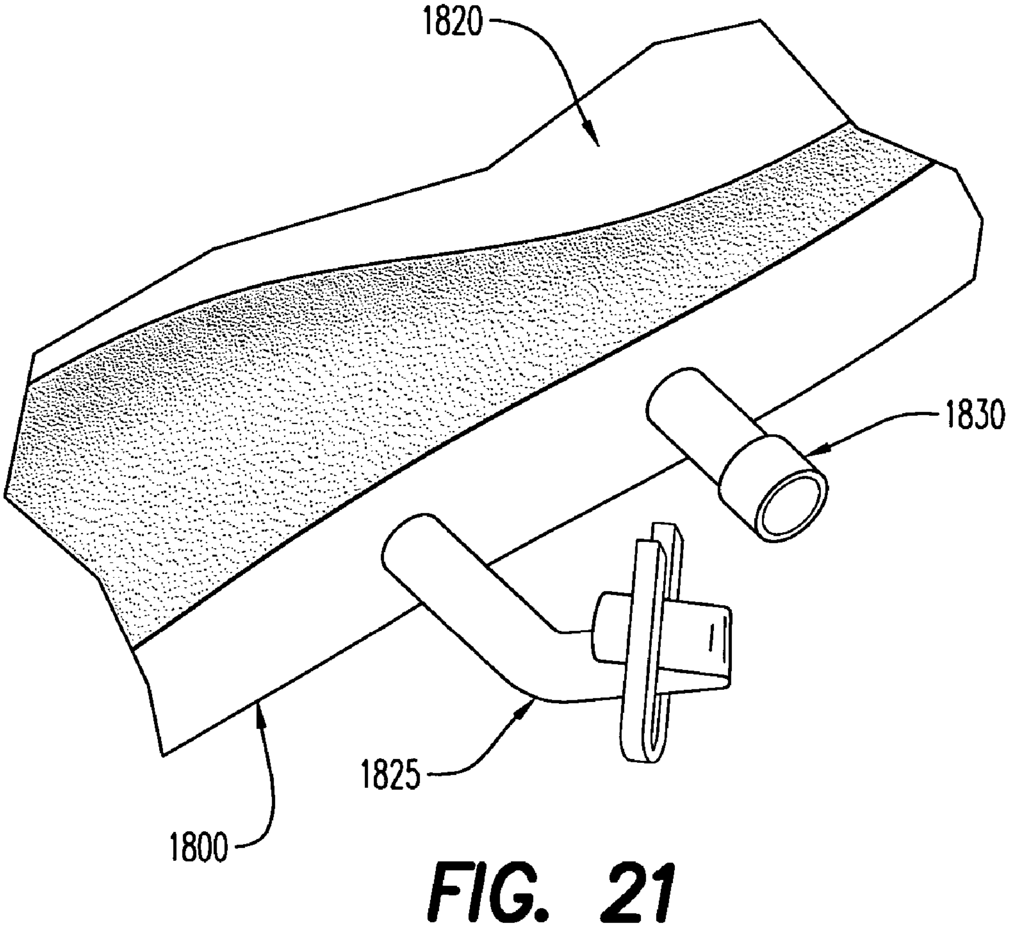
FIG. 21 is a detailed view of the exemplary insole of FIG. 20, more clearly illustrating the dual valve system.

FIG. 21 is a detailed view of the exemplary insole 1800 of FIG. 20, more clearly illustrating the dual valve system including input valve 1825 and output valve 1830.

Figure 22A:
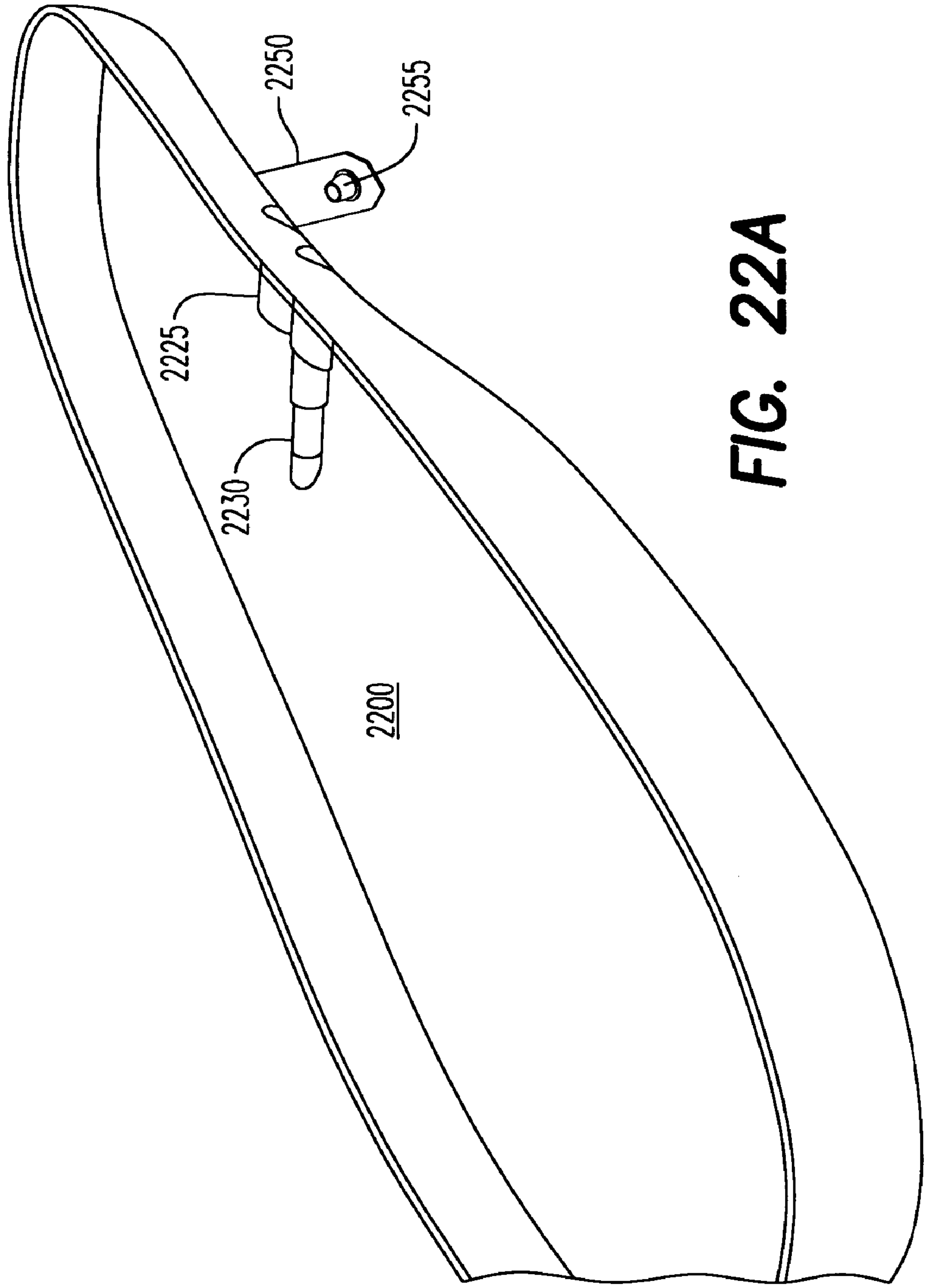
FIGS. 22A and 22B depict the inside midsole with valve and air line shows valve outlet on outerside of arch with open close air with flap system.
Figure 22B:
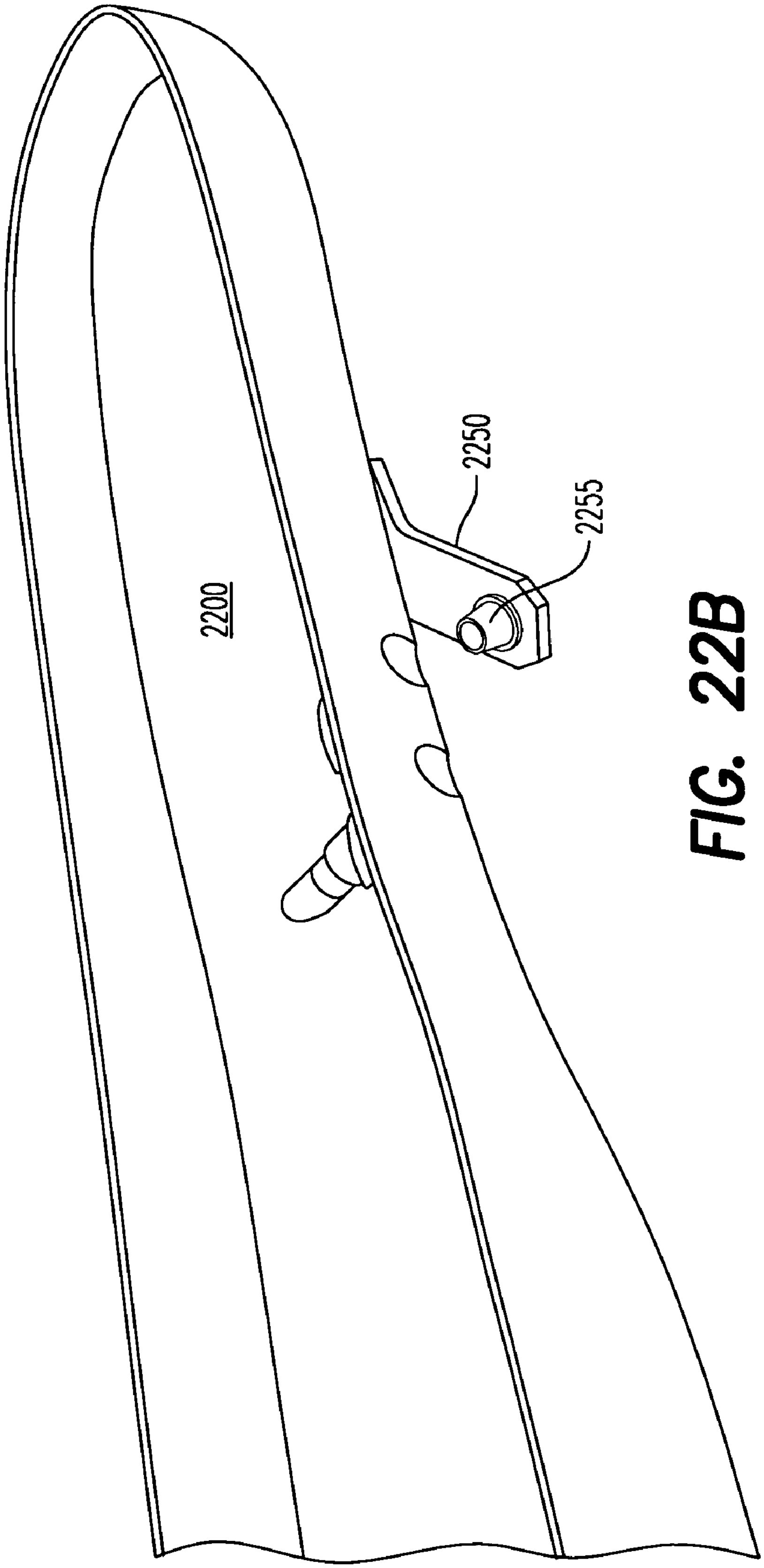

FIGS. 22A and 22B depict the inside of a midsole 2200 including an outlet valve 2230, and an inlet air line 2225 shows outlet valve 2230 on the outerside of the arch portion of midsole 2200. A flap system, including a flap 2250 and plug 2255, is included. Plug 2255 prevents air from leaking into air line 2225. An additional plug may also be applied to valve 2230.

A plug such as plug 2255 of FIGS. 22A and 22B may serve as a simple press in/pull out valve to allow air to escape. The plug may also serve to prevent dirt, water, and other debris from entering the air line.

Figure 23:
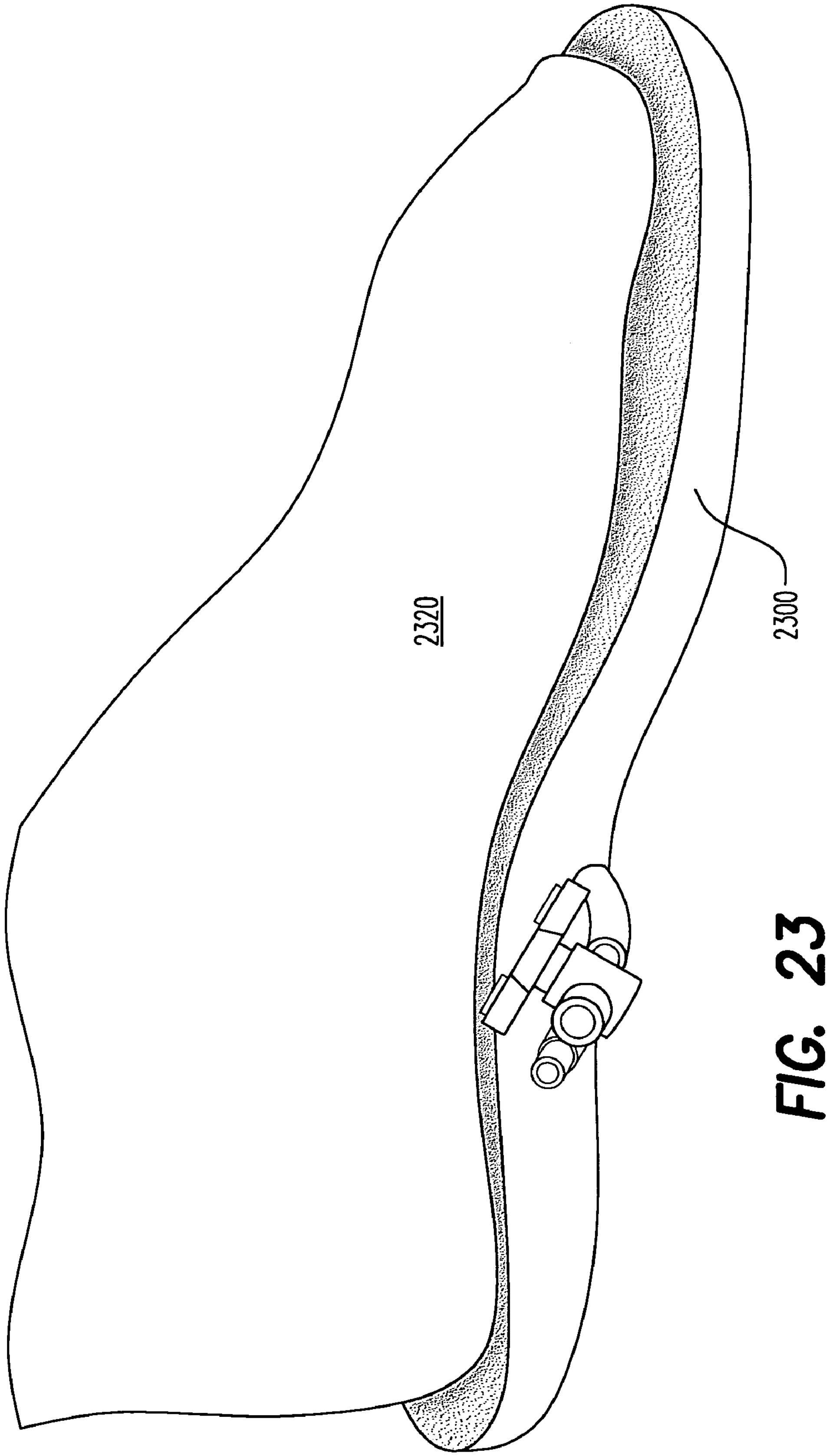
FIG. 23 depicts a contoured midsole with particles inside, valves attached, contour impression locked with foot resting in the impression.

FIG. 23 depicts a contoured midsole 2300 with particles inside, valves attached, contour impression locked with foot 2320 resting in the impression.

In one embodiment, all particles are subjected to an anti-static process either during manufacture of the particles or prior to loading the particles into the housing. Removal of static charge prevents the particles from clinging to unwanted surfaces and may improve the contouring ability of the particles.

Figure 24:
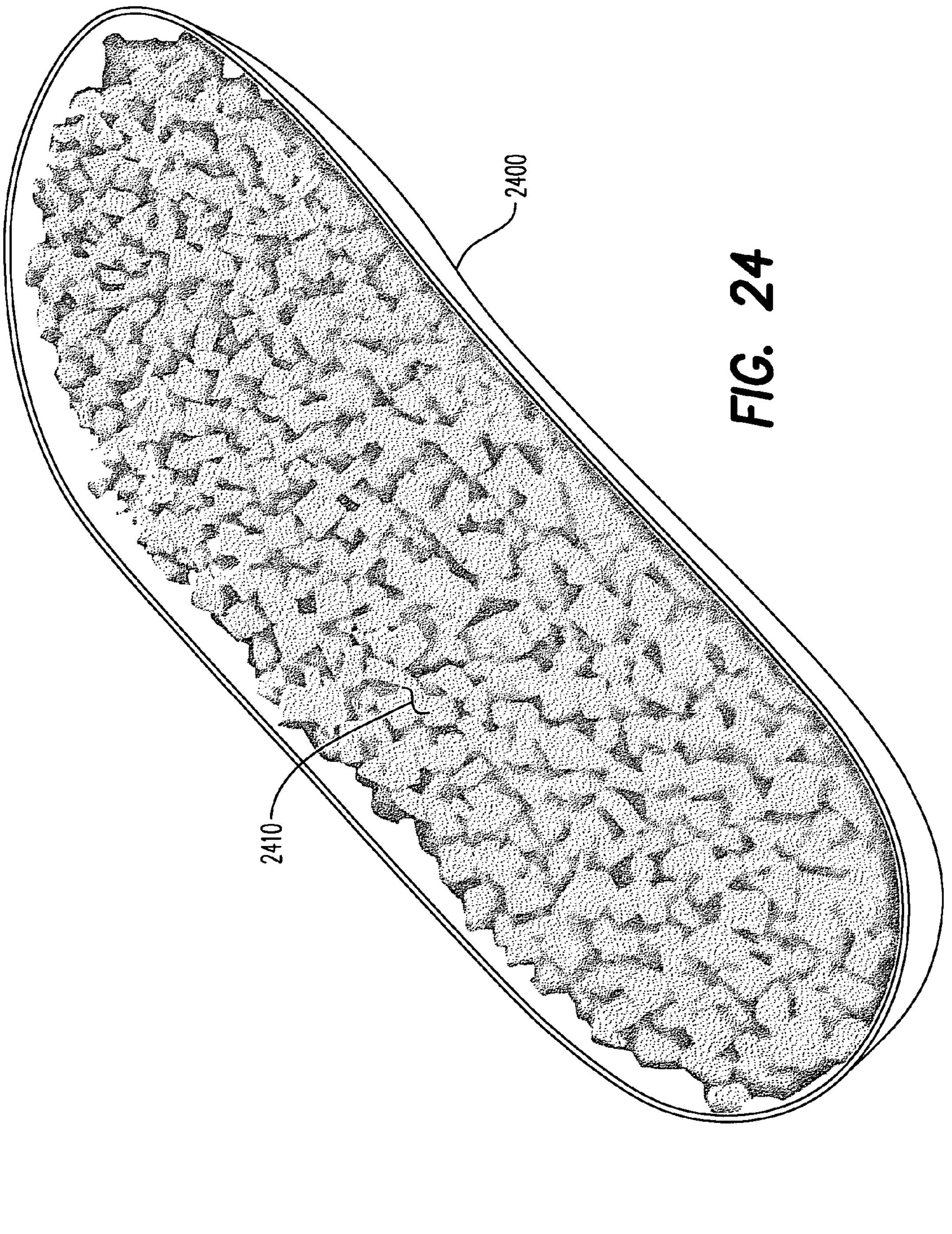
FIG. 24 depicts a midsole container with foam particles inside.

Particles or beads may come in a variety of shapes, sizes and materials. In on example, FIG. 24 depicts midsole container 2400 with foam particles 2410 inside. Bead density may also be varied to provide softer or firmer 3-D capture devices, and further a variety of densities can be simultaneously used in the device to provide varying degrees of softness or firmness.

The valves described herein may be manually activated via mechanical devices, or controlled by electromechanical systems. The valves may be unidirectional or bidirectional. A single valve or multiple valves may be utilized with the 3-D capture system.

An electro-mechanical system allows easy modification of a 3-D capture system, and may be used to control a single valve or multiple valves. For example, the foot contour of a midsole/insole may be modified while in a static position, while rocking the foot, or in a dynamic position such as while walking. A remote control device may be used to modify the contour. A voice activation circuit may also be incorporated into a control system.

Figure 25A:
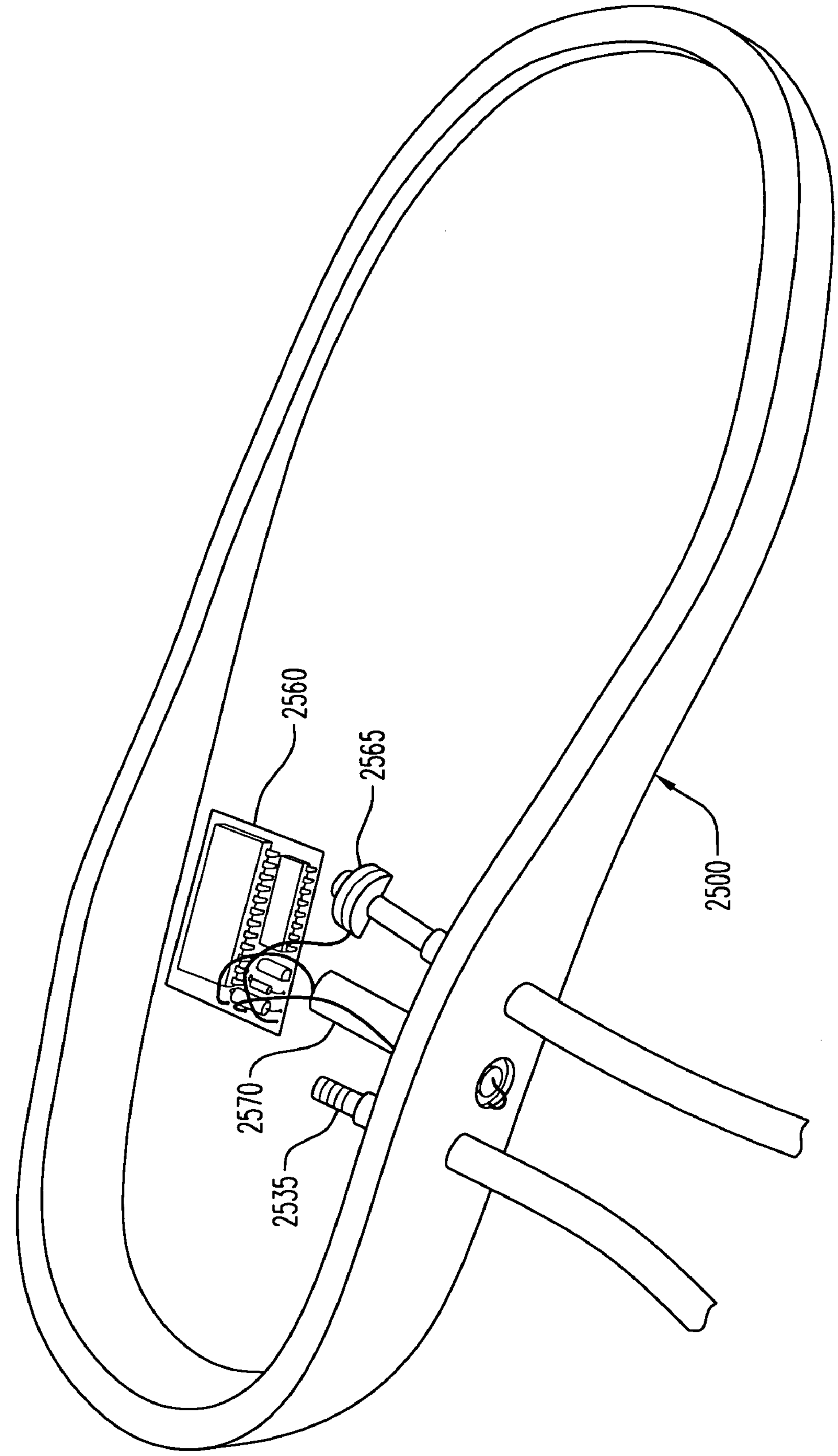
FIG. 25A depicts a midsole bottom with electronic processor controls and mechanical valve control for air flow with battery power.
Figure 25B:
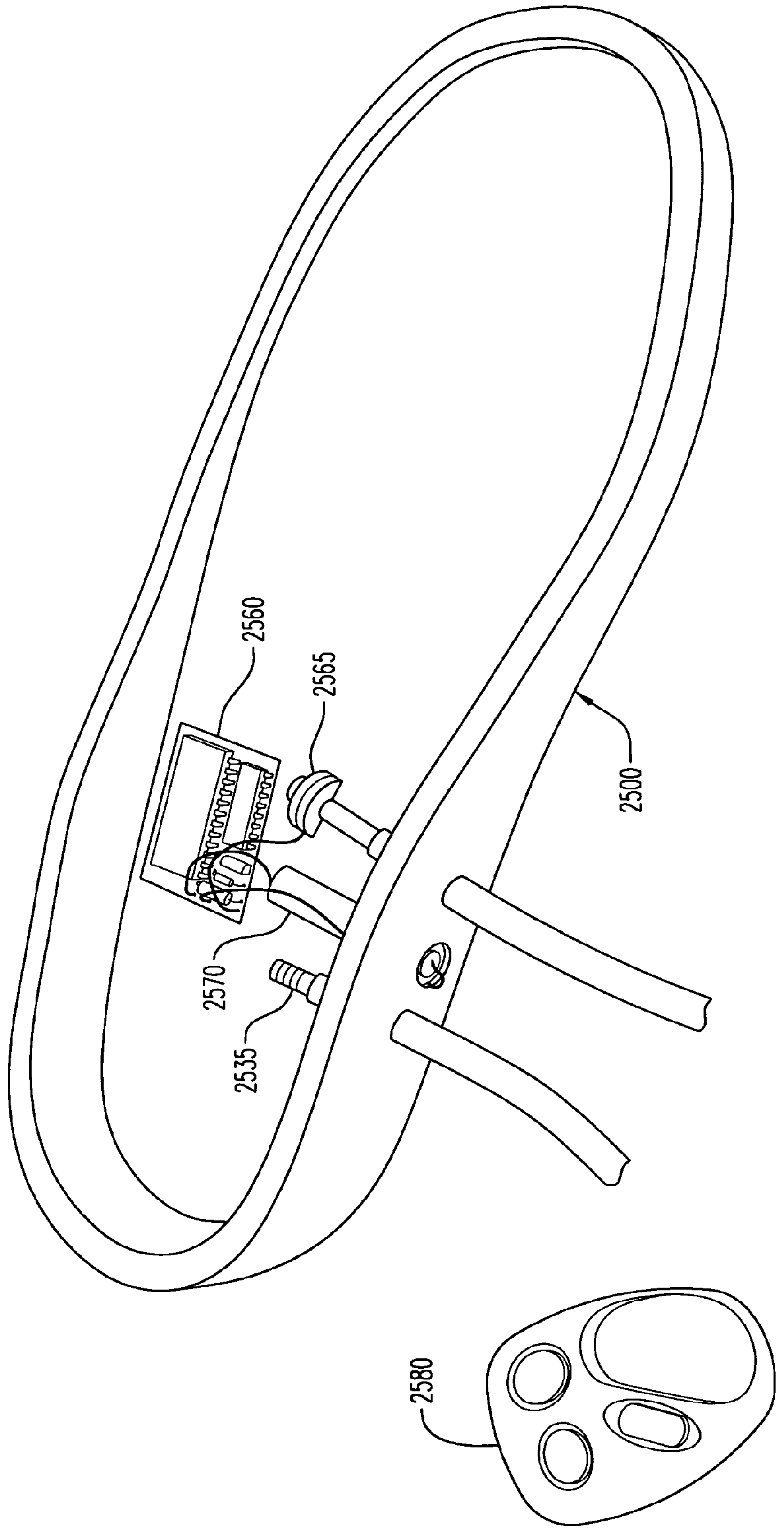
FIG. 25B depicts remote control. May be voice controlled or by hand.

FIG. 25A depicts midsole bottom 2500 with electronic processor control system 2560 connected to bi-directional valve 2565 for mechanical control of valve 2565 to control air flow. The processor control system 2560 is powered by battery 2570. FIG. 25B additionally depicts remote control 2575. The valve may be operated remotely or by a touch button switch attached to midsole bottom 2500 or elsewhere. An additional backup valve such as outlet valve may be included, such as with a plugged end, to reset the contour of the midsole.

In another aspect, the remote control is utilized to activate preferably electrically operated air valves. A preferred battery is a CR2016 flat lithium 3.6 V battery. In order for the remote control to work, the battery must continually be connected to the processor. To preserve the battery life, a midsole side button can be installed to allow a user to disconnect the battery. The user may push the button to activate the battery and unlock the valve. Alternatively, the control system may be set to connect or disconnect the battery automatically. An associated LED is preferably included to indicate that power to the processor is "on". The button can be pushed again to turn "off" the power and close the locking valve.

In another aspect, a receiver associated with the electronic processor is preferably customized to respond to a specific remote control frequency. In another embodiment, a distinct remote control frequency may be assigned to each midsole/insole so that the user has the option of adjusting only one insole/midsole or both simultaneously. In a further embodiment, individual pairs of insoles/midsoles are assigned different remote control frequencies to avoid accidental modification of other pairs of insoles/midsoles when two or more users are near one another.

Where a specific shoe is designed in conjunction with a specific insole/midsole, an electronic processor may also be used to ensure that the midsole/insole is not used in another pair of shoes. The designated pair of shoes contains an identification mechanism that is readable by a processor in the midsole/insole. The processor will then prevent use of the midsole/insole unless it reads the proper designated identification signal from the designated shoe.

Because particles have the potential to become statically charged, it may also be desirable to place a layer of shielding material to protect the electronic control system. A shielding layer will prevent damage to the control system due to static charges.

The control system may also automatically activate in response to inputted conditions. For example, a specific desired hardness may be set by the user, and the control system can modify the air/liquid volume to maintain the desired hardness.

In another aspect, the 3-D capture system may incorporate an electro-mechanical control system to allow the contour to periodically reset in response to movement. An example of such a system is a mattress pad or mattress topper. Additionally, a valve system may be connected to a vacuum pump which is controlled by the control system. A sensor is also included to sense movement. The control system can respond to signals from the sensor to allow air into the 3-D capture system to reset the contour. The vacuum pump may then be engaged to set a new contour based on a position of a user's body after the movement.

In another example, a heat sensor is incorporated into the control system to control the temperature of the midsole/insole, seat or other 3-D capture device. A desired maximum temperature may be set, above which the heat sensor sends a signal to the control system to open an air valve to provide circulation and cool the device. When used in a midsole/insole, the heat sensor opens a valve to allow air to circulate through the midsole/insole. Walking movement provides a pumping effect by driving out warm air and drawing cooler outside air into the midsole/insole. This embodiment may be specifically useful as insoles/midsoles for boots such as military boots, especially for use in hot climates such as a desert. This embodiment may also be useful in automatically controlling the temperature of a seat. In one example, a temperature control system including the heat sensor, control system including all control logic circuits, is utilized in a seat for a wheelchair, particularly for paraplegic users.

In another aspect hereof, a particle injector is provided to fill or inject particles such as beads into the midsole/insole housing. Particles can be injected by air pressure, mechanical force, gravity, or a combination. A gravity system may be most useful in a store or factory that manufactures devices such as footwear that include the 3-D capture device. A vibrator may also be included to move the particles and prevent them from accumulating in one area. The particle injector may also be used in reverse, to suck extra beads from the 3-D capture device.

Figure 26:
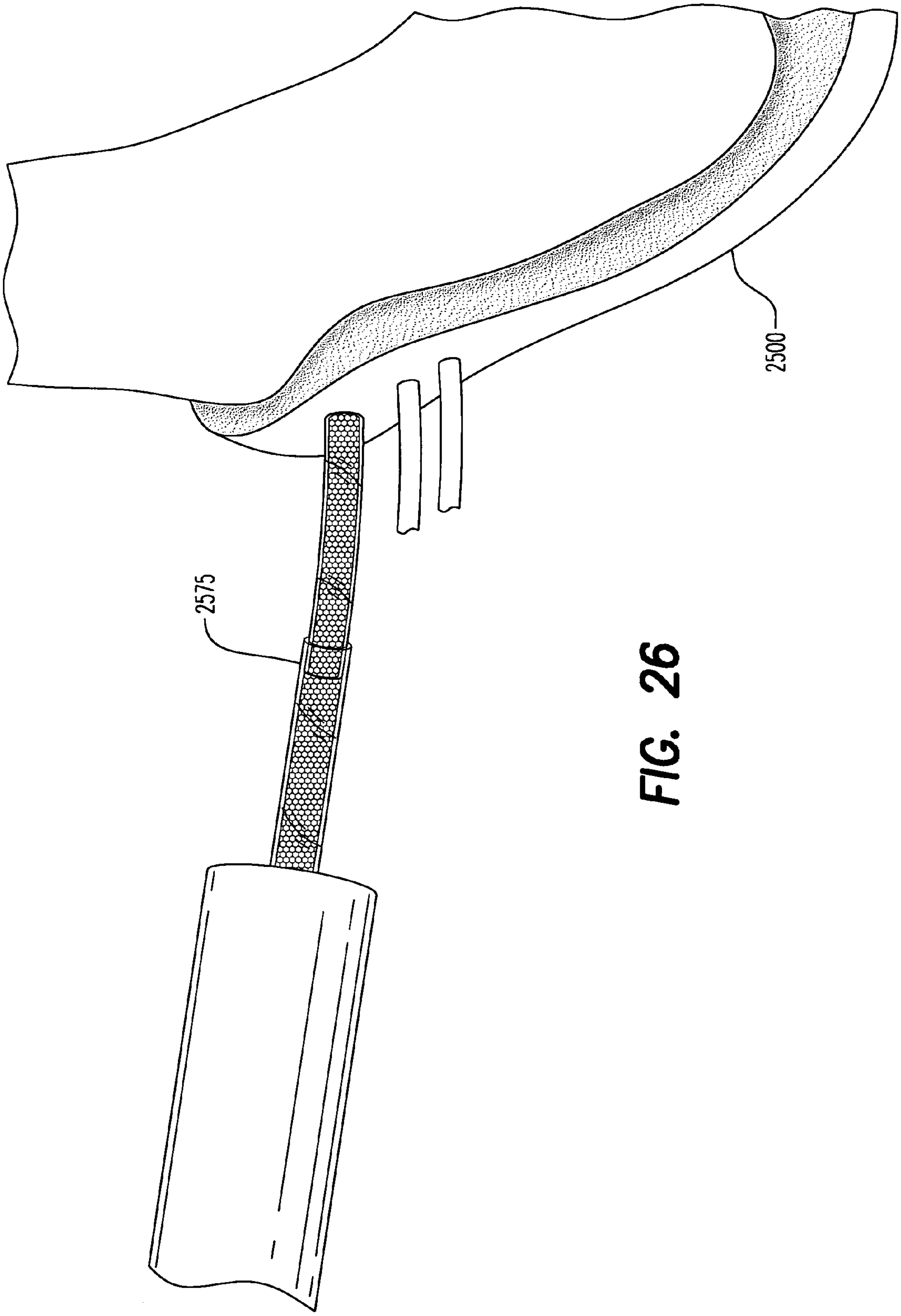
FIG. 26 depicts the a midsole container with a bead particle injector.
Figure 27:
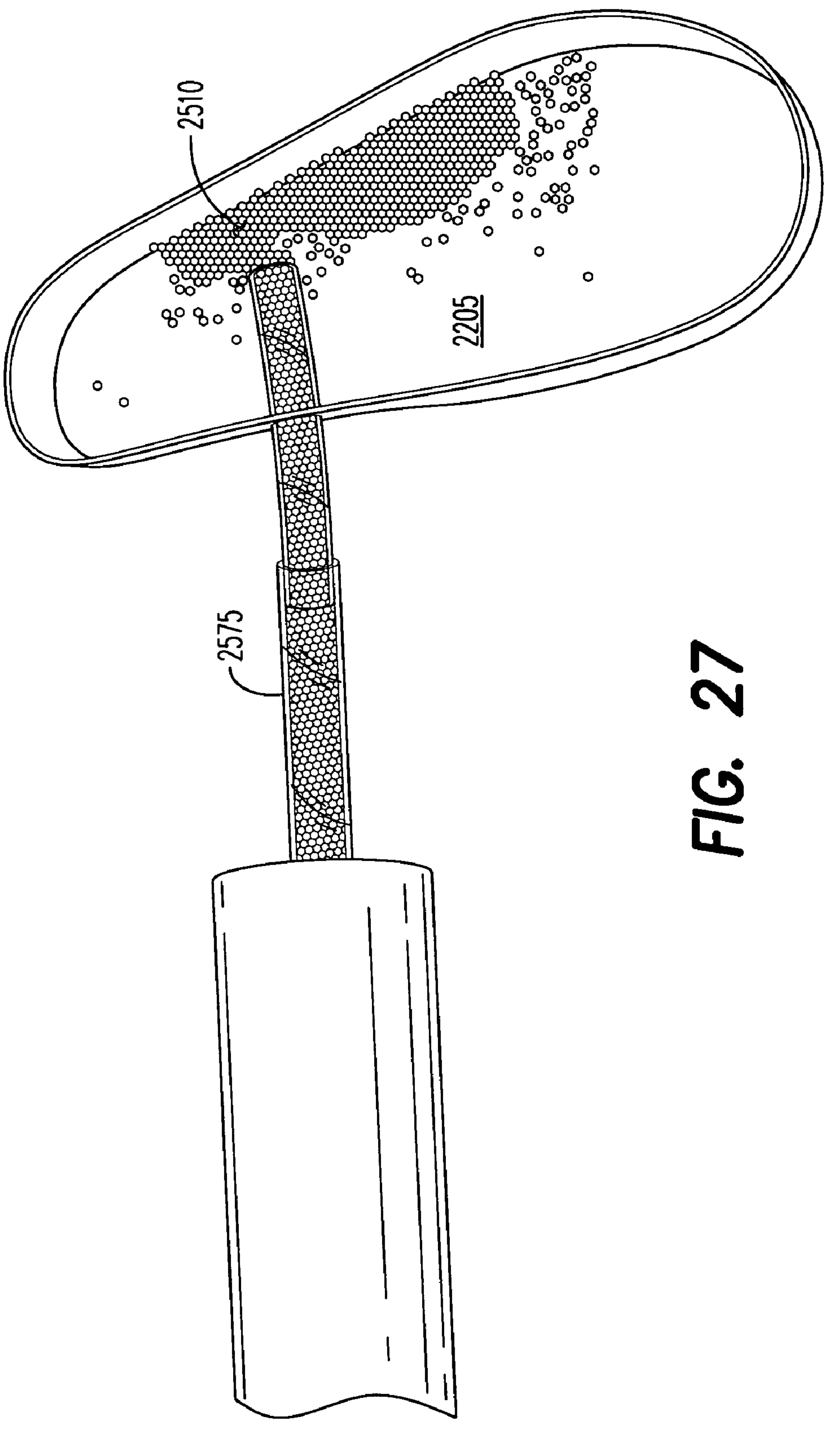
FIG. 27 depicts a midsole container with a bead particle injector.

FIG. 26 depicts midsole 2500 including particle injector 2575. FIG. 27 depicts midsole container 2505 with bead particle injector 2575. Particle injector 2575 operates to force beads 2510 into midsole container 2505.

Figure 55A:
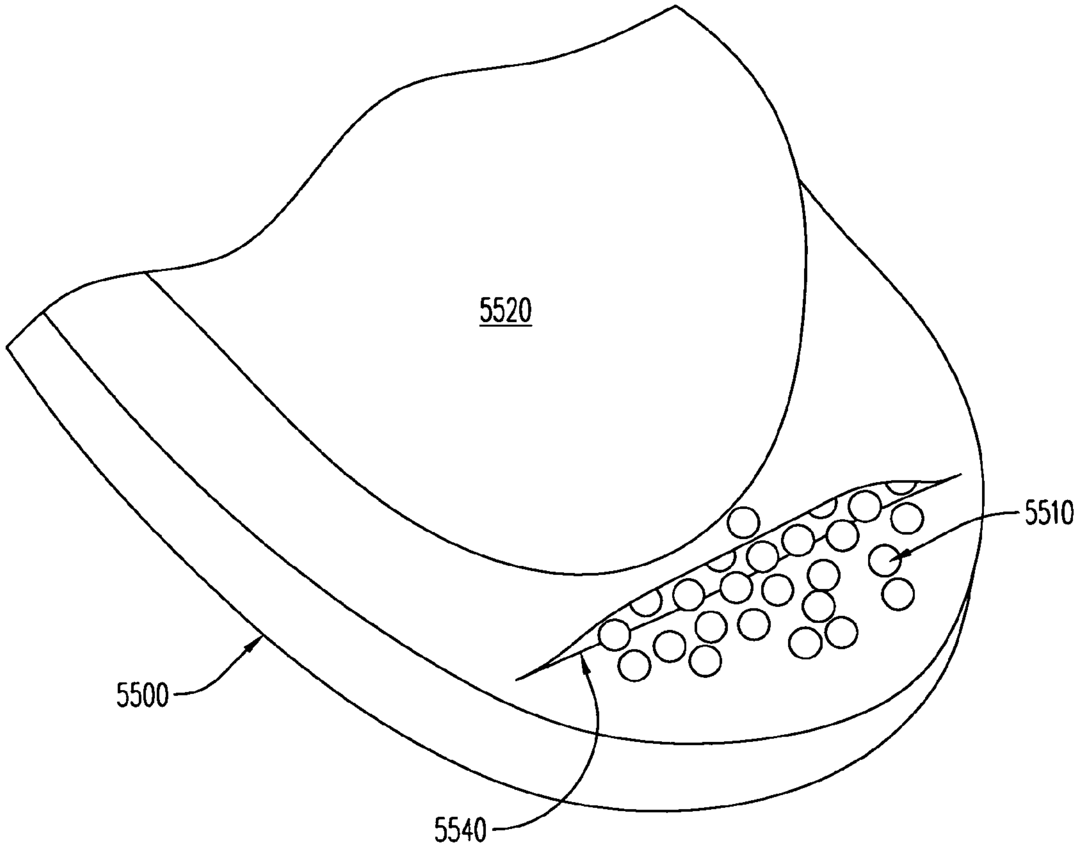
FIG. 55A depicts a midsole including an opening for release of excess particles.
Figure 55B:
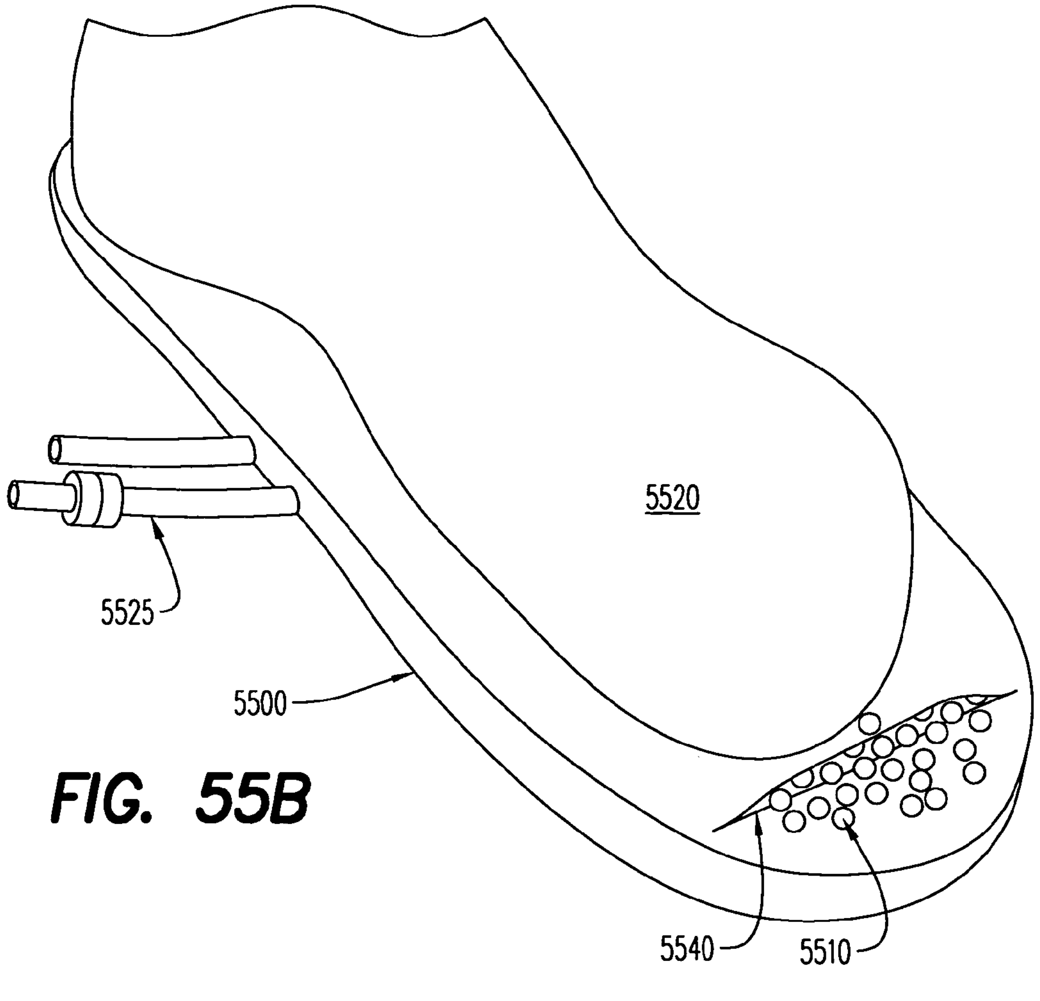
FIG. 55B depicts the midsole of FIG. 55A including a valve system.

In another aspect, an opening, such as a slit, is located on the container to allow excess beads to escape from the container when pressure is applied. FIGS. 55A and 55B illustrates an example of this aspect. Midsole 5500 is shown having an opening 5540 through which excess beads 5510 escape midsole 5500. FIG. 55B also shows valve system 5525.

A patch is located over the opening to allow excess beads to escape but prevent air from entering. The patch may be a logo. In the embodiment of a sandal or an innersole, the opening should be located on an area of the sandal or innersole that would not be covered by a foot when worn. When pressure is applied to the foot, the opening and patch allow excess beads to escape but does not allow air to re-enter when pressure is removed.

In another aspect, the container features adhesive surfaces to hold a layer of particles in place. Adhesive surfaces may be a surface of the housing coated with an adhesive, or an additional layer of material coated with an adhesive that is applied to the additional layer, such as double-sided adhesive tape.

An adhesive surface applied to the housing will reduce particle migration when the vacuum hold is off or nearly off. Ah adhesive layer will also reduce particle migration due to shear forces applied by the foot's plantar surfaces when walking. In another embodiment, only the weight bearing surfaces of the container are coated with an adhesive material. For a midsole/insole, the forefoot ball and heel areas of the container, where most shearing forces are located, are coated with an adhesive to have a sticky quality. In another embodiment, the higher inside elevations of the container wall may also be coated with an adhesive to catch and hold excessive beads or particles. The undersurface of a cover of midsole/insole 2800, such as midliner cover 2817 shown in FIG. 28, may also be coated with an adhesive if desired.

In place of an adhesive surface in the bottom of a container such as a midsole/insole container, and/or on the underside of a cover, a rough, pock-marked surface may be used to reduce unwanted particle migration. The rough or pock-marked surface should be made from a resilient material.

Figure 29A:
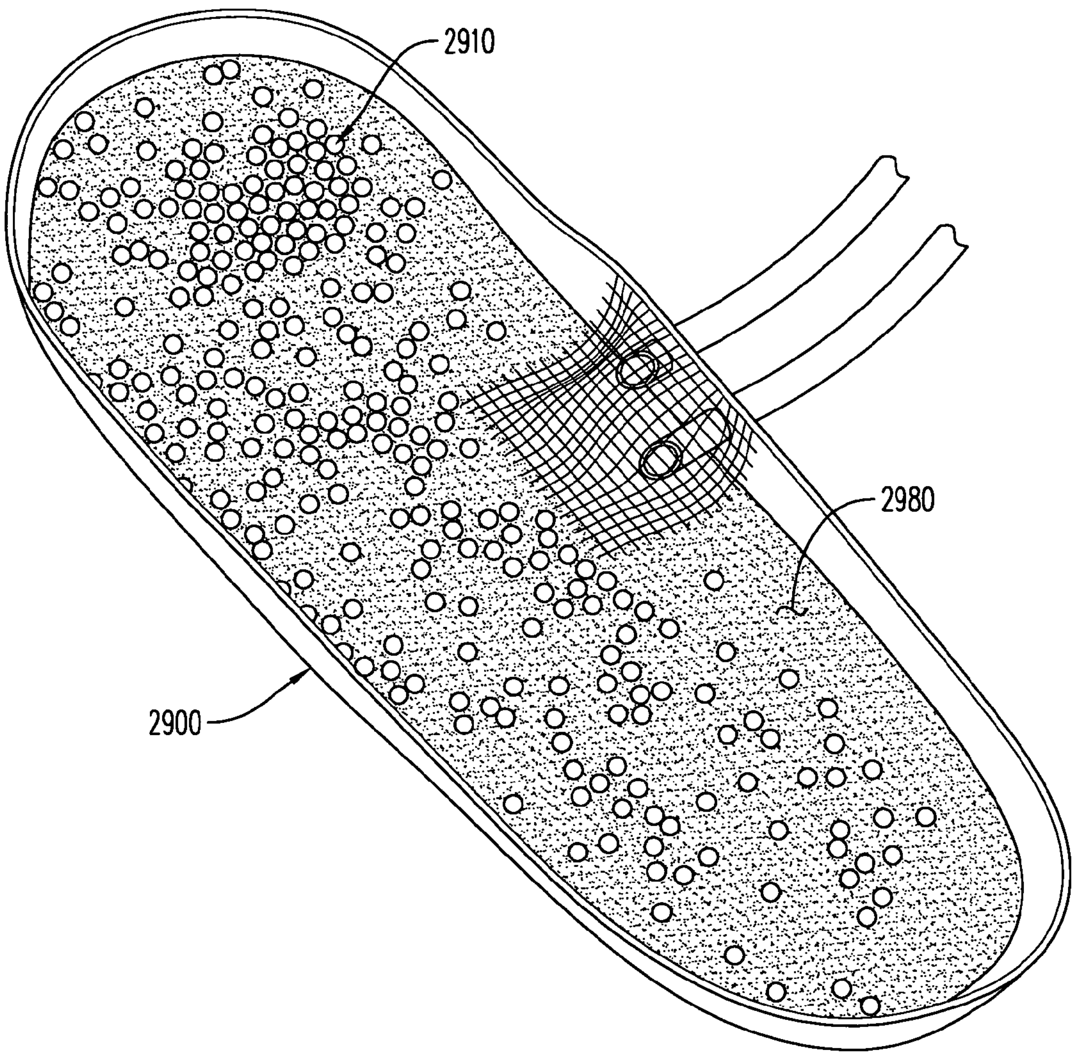
FIGS. 29A and 29B depict inner midsole bottom coated with sticky, adhesive material.
Figure 29B:
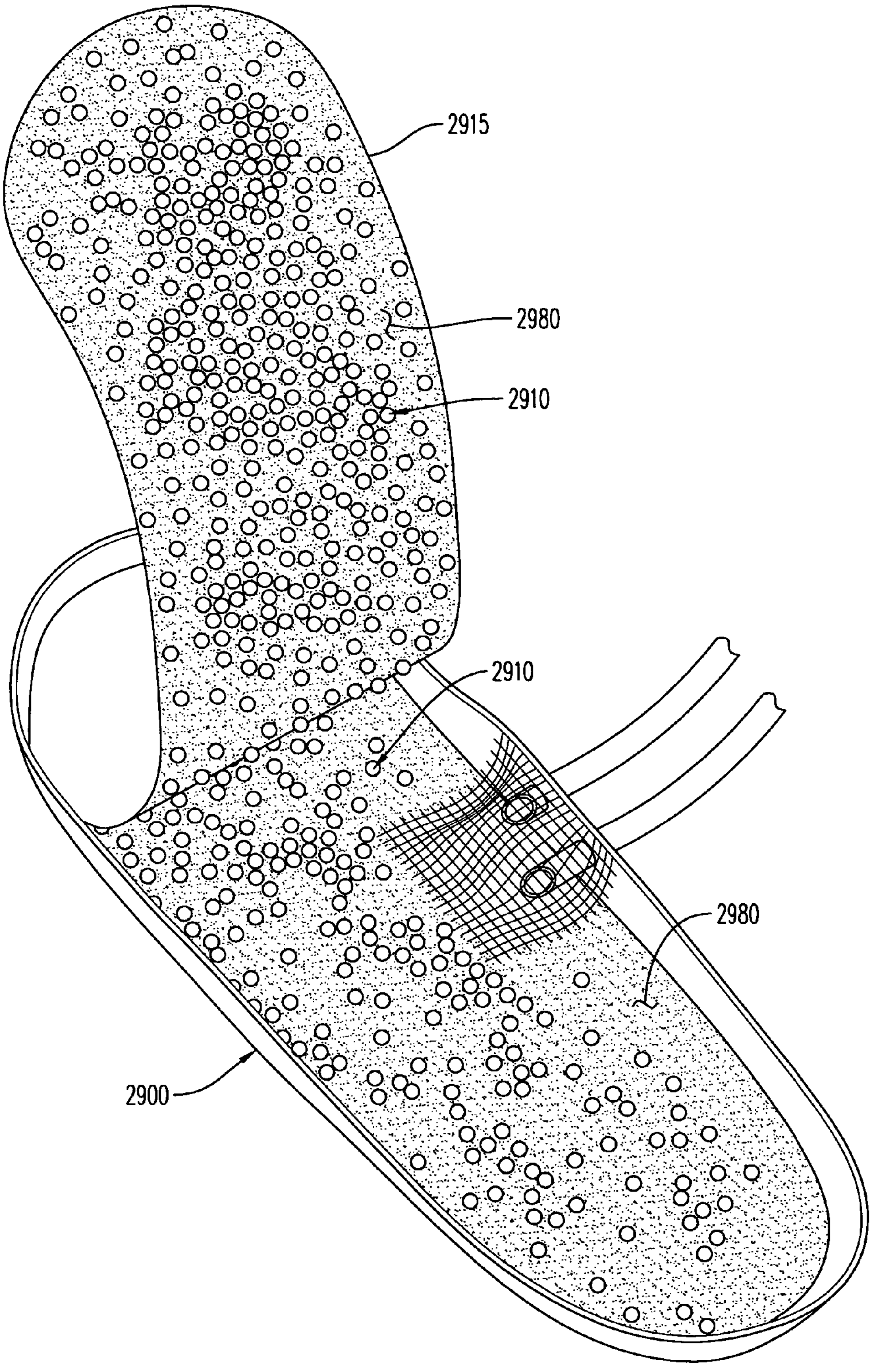

FIGS. 29A and 29B depict inner midsole 2900 having a bottom 2980 coated with an adhesive material to provide adhesive surface 2980 to more effectively hold beads 2910 when the vacuum is off and when aggressive shearing forces are applied by a foot's bottom. As shown in FIG. 29B, a top liner 2915 may also be coated or otherwise provided with adhesive surface 2980.

In another embodiment, the container bottom contains partitions to reduce migration of particles. The partitions can be included in addition to an adhesive bottom to further aid in unwanted particle migration.

Figure 30:
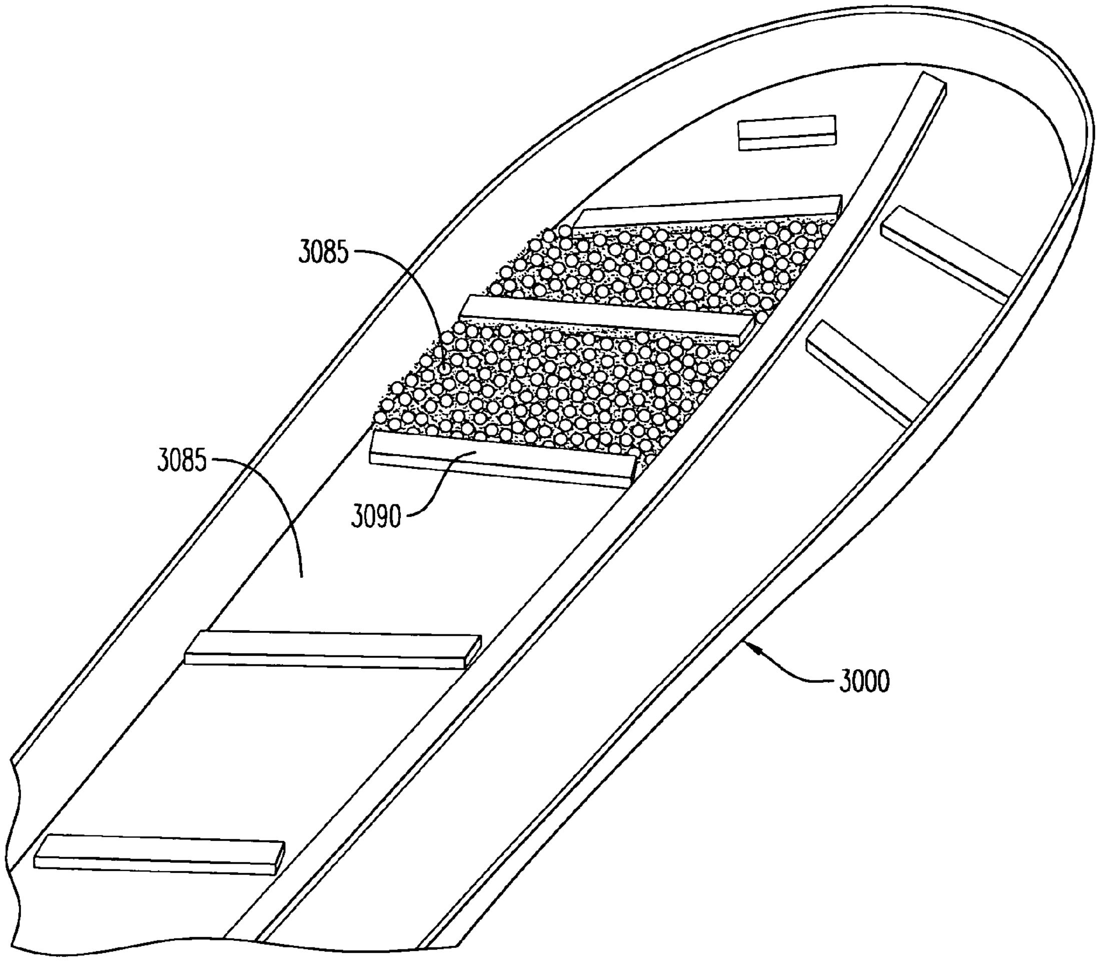
FIG. 30 depicts a midsole container with partitions having sections with a sticky, adhesive surface.

FIG. 30 depicts the inside of midsole container 3000 with partitions/barriers 3090. As shown in FIG. 30, some of sections 3085 formed by partitions 3090 are coated with an adhesive material to further help in controlling bead movement when the air vacuum is off and when the foot applies shearing forces.

Figure 28:
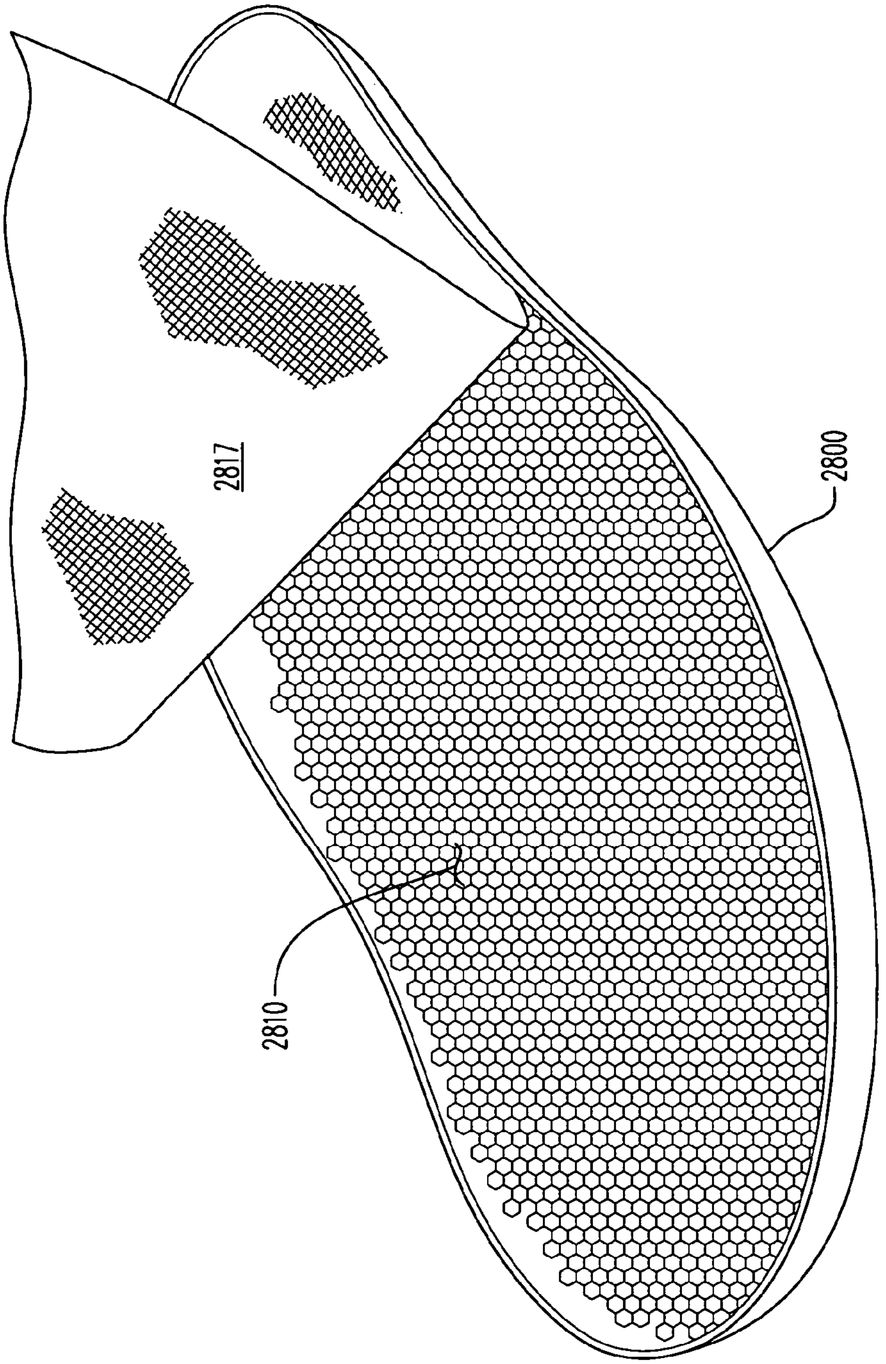
FIG. 28 depicts a midsole container with beads inside with a mid liner cover.

In another aspect, a window-type mesh screen layer is placed on top of the beads or particles. The screen allows air to move through to the underside of the top layer to improve vacuum force. The screen also smooths the upper surface of the midsole/insole to prevent a lumpy particle surface from showing through the top layer. FIG. 28 depicts midsole/insole 2800 with beads 2810 inside including mid liner cover 2817, preferably in the form of a mesh screen layer, that provides a smoother feel and prevents any lumpy beads from showing through the top finish layer.

Figure 31A:
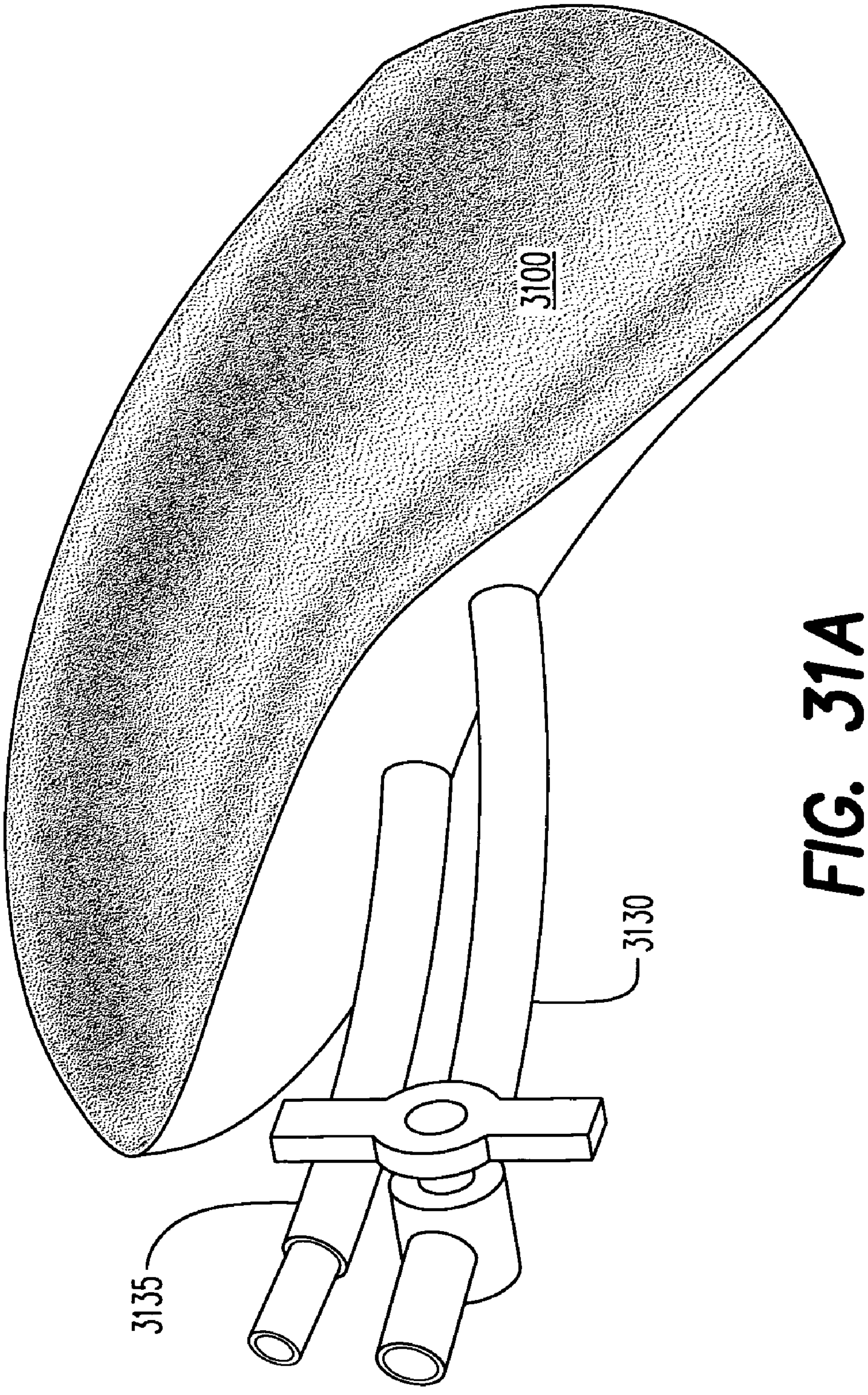
FIGS. 31A and 31B depict a ⅔ long orthotic with valves attached.
Figure 31B:
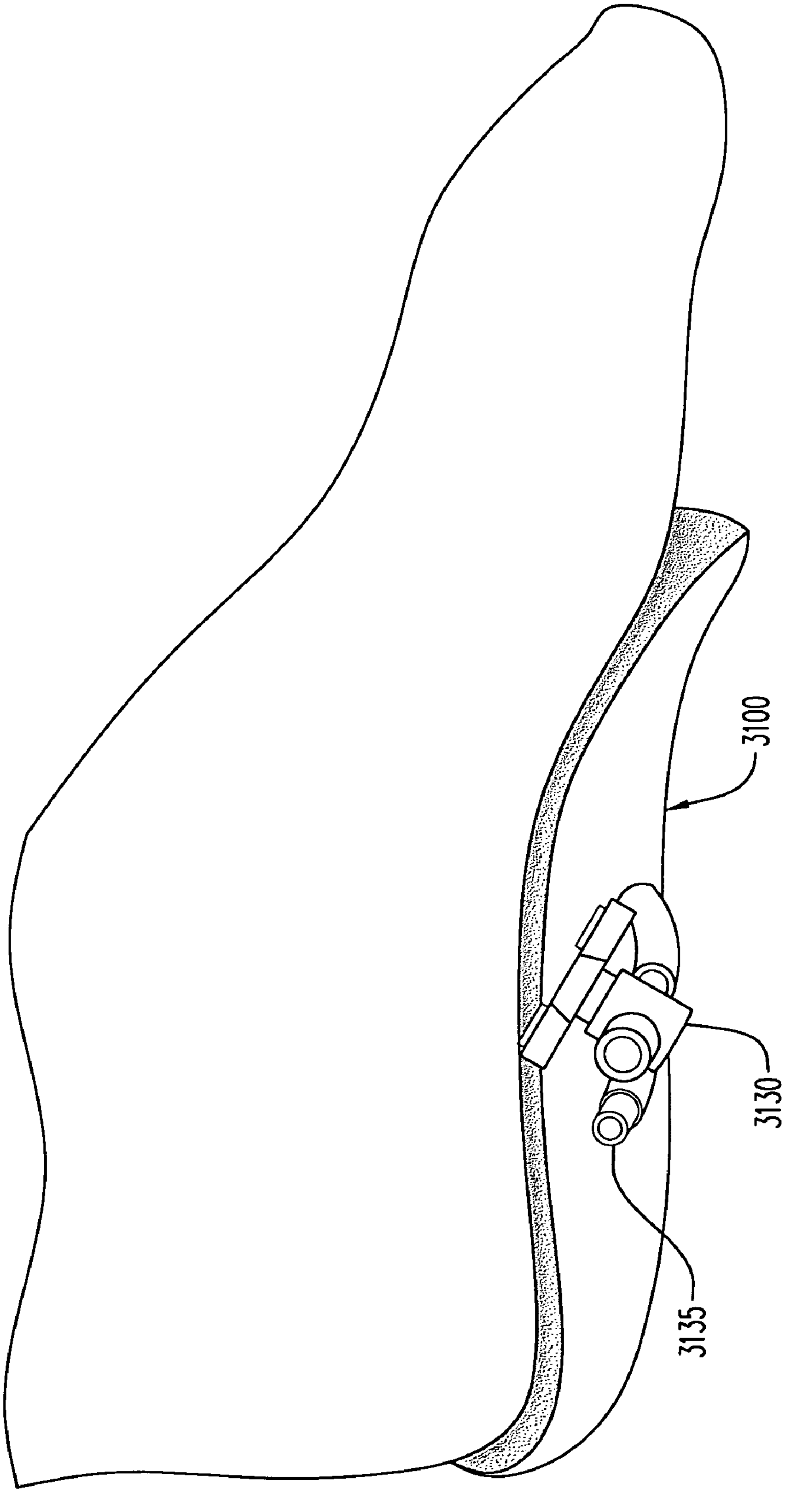

In another aspect, the 3-D capture device in the form of an orthotic support. An example is shown in FIGS. 31A and 31B, which depict a ⅔ long, i.e. ⅔ the length of a foot, orthotic 3100 including attached valves 3130 and 3135. Valve 3130 is an inlet valve including the associated inlet line, and valve 3135 is an outlet valve including an associated outlet line.

Figure 56:
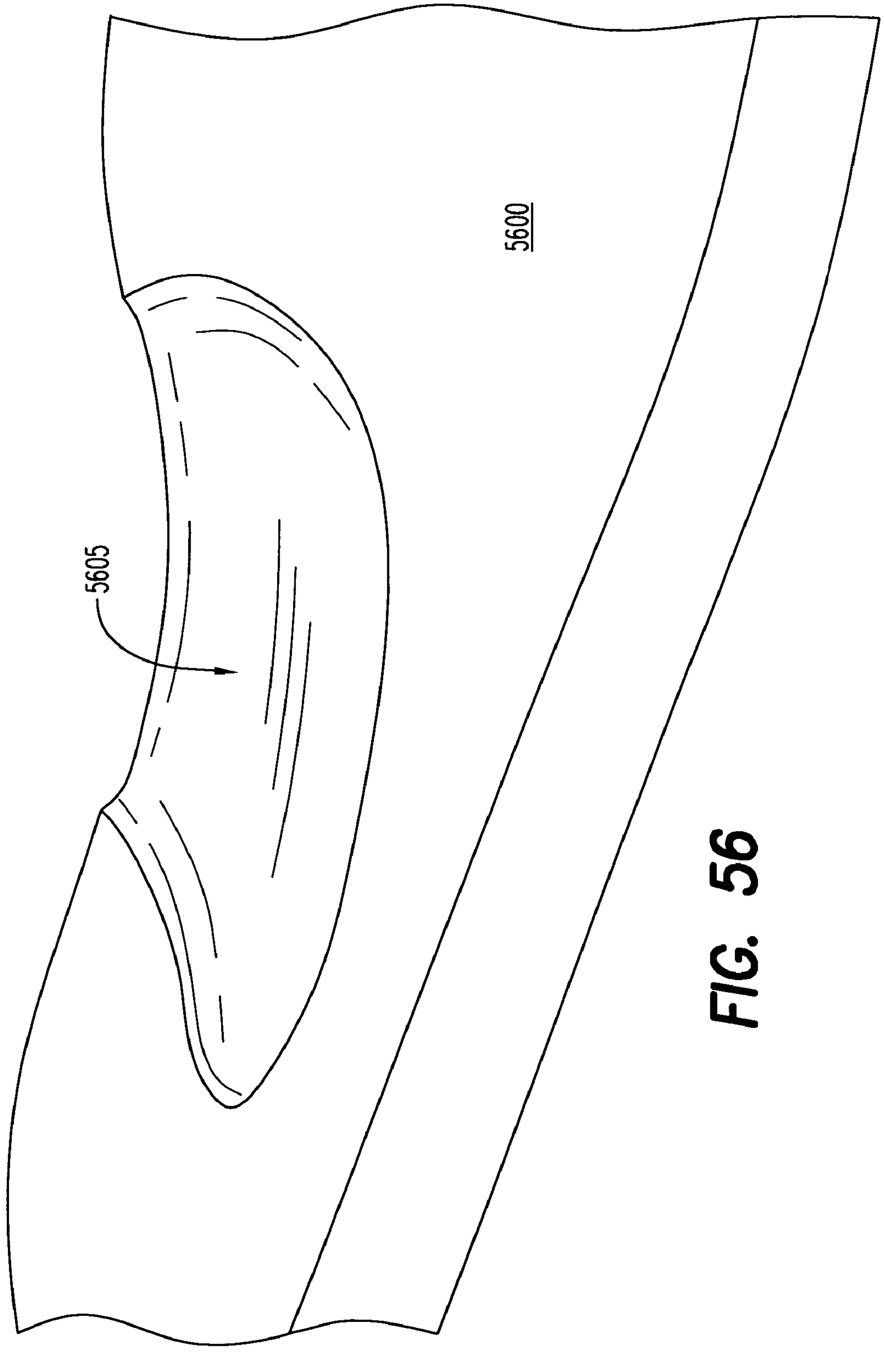
FIG. 56 depicts an insole container having a support portion.

A midsole container, insole container or orthotic container may include built in supports for the metatarsals, longitudinal arch, lateral arch and radius of the heel. The midsole container may be concave at the bottom to allow a suspension effect and spring effect to increase comfort. When used in an insole or orthotic, the bottom side of the container can also be concave. This shape will more easily mate with the built in shank curve rise inside the bottom of the shoe, especially in the case of rigid containers. This shape is illustrated in FIG. 56, which shows a container 5600 having a raised support portion 5605 to accommodate a shoe with a built-in shank.

Figure 32:
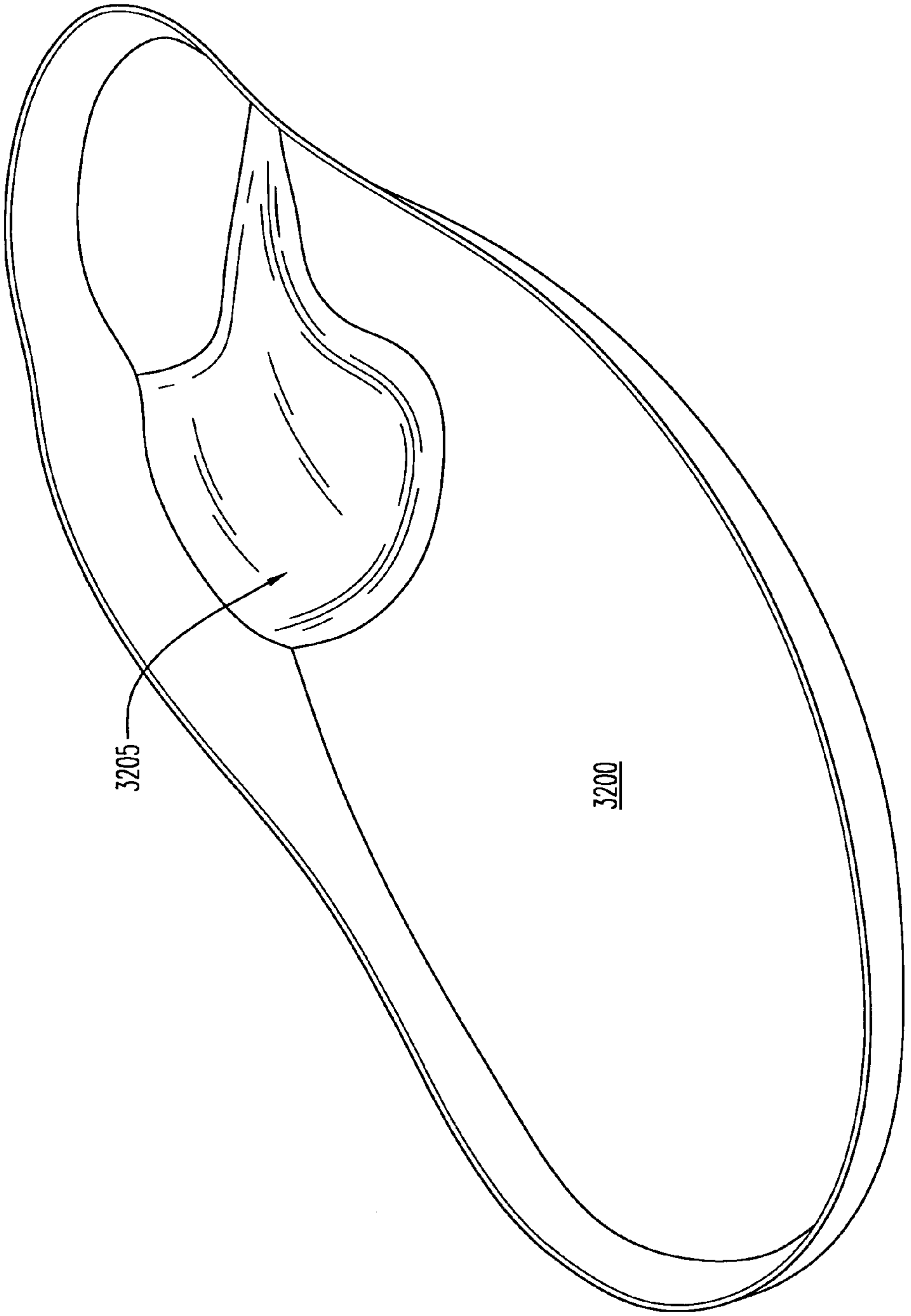
FIG. 32 depicts pre shaped contouring of a midsole/insole container.

FIG. 32 depicts pre shaped contouring of the midsole/insole container to add extra support to the metatarsal arches, lateral arch and heel radius with the bottom of the midsole/insole container having a concaved radius to provide give when extra force is applied to the arch. FIG. 32 shows contouring of the container 3200 showing support region 3205.

Figure 33:
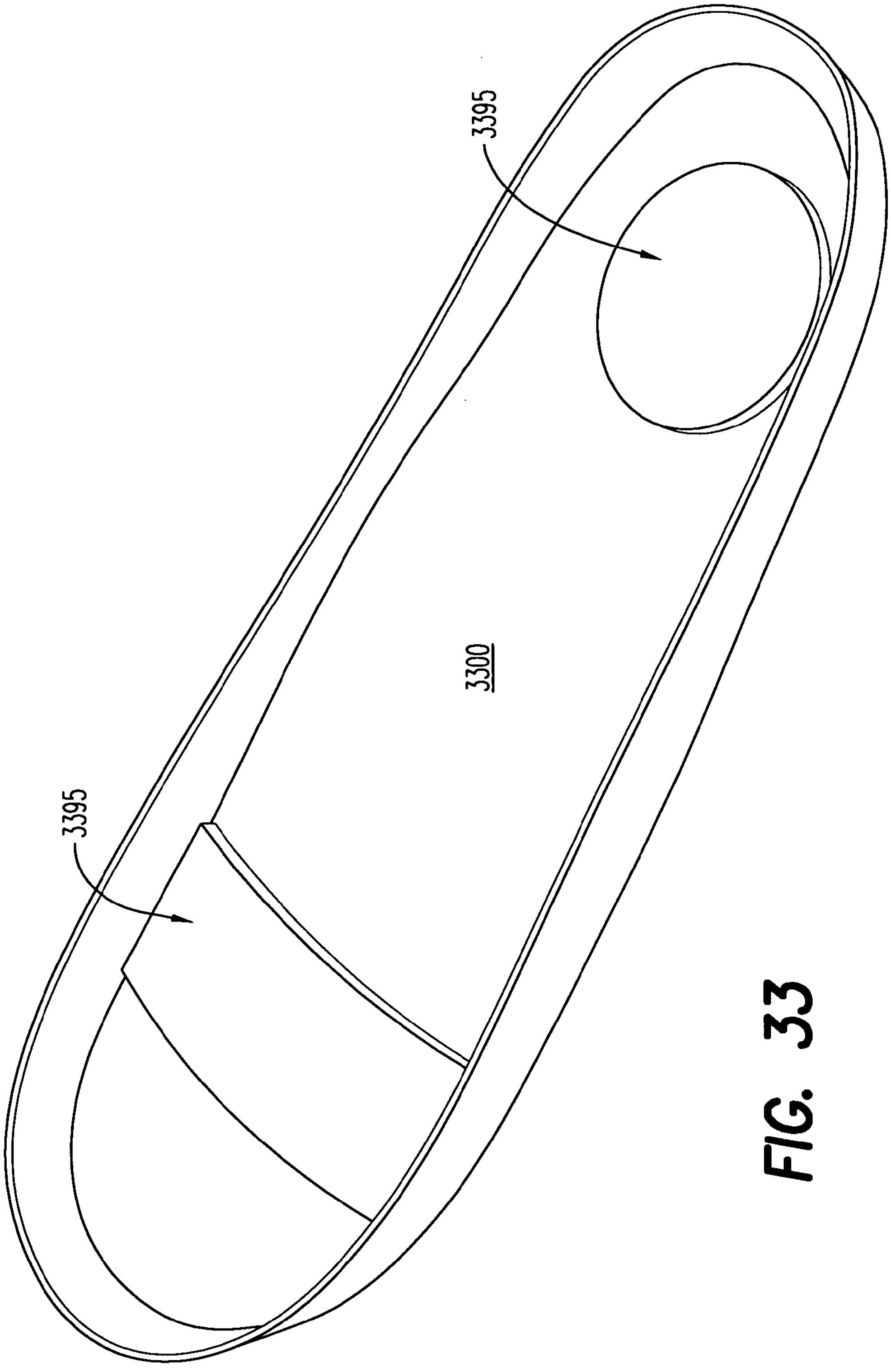
FIG. 33 depicts a midsole/insole with placement of resilient material under the heel and forefoot ball.

In another aspect, instead of molding supports directly into the midsole/insole container as in FIG. 32, resilient pads such as a resilient metatarsal pad can be positioned on the container. This embodiment provides resilient compression and provides a slight spring effect. FIG. 33 depicts midsole/insole container 3300 with placement of resilient material 3395 under the heel and forefoot ball for extra shock absorbing. The resilient material lays under the beads in a completed midsole/insole.

Figure 34:
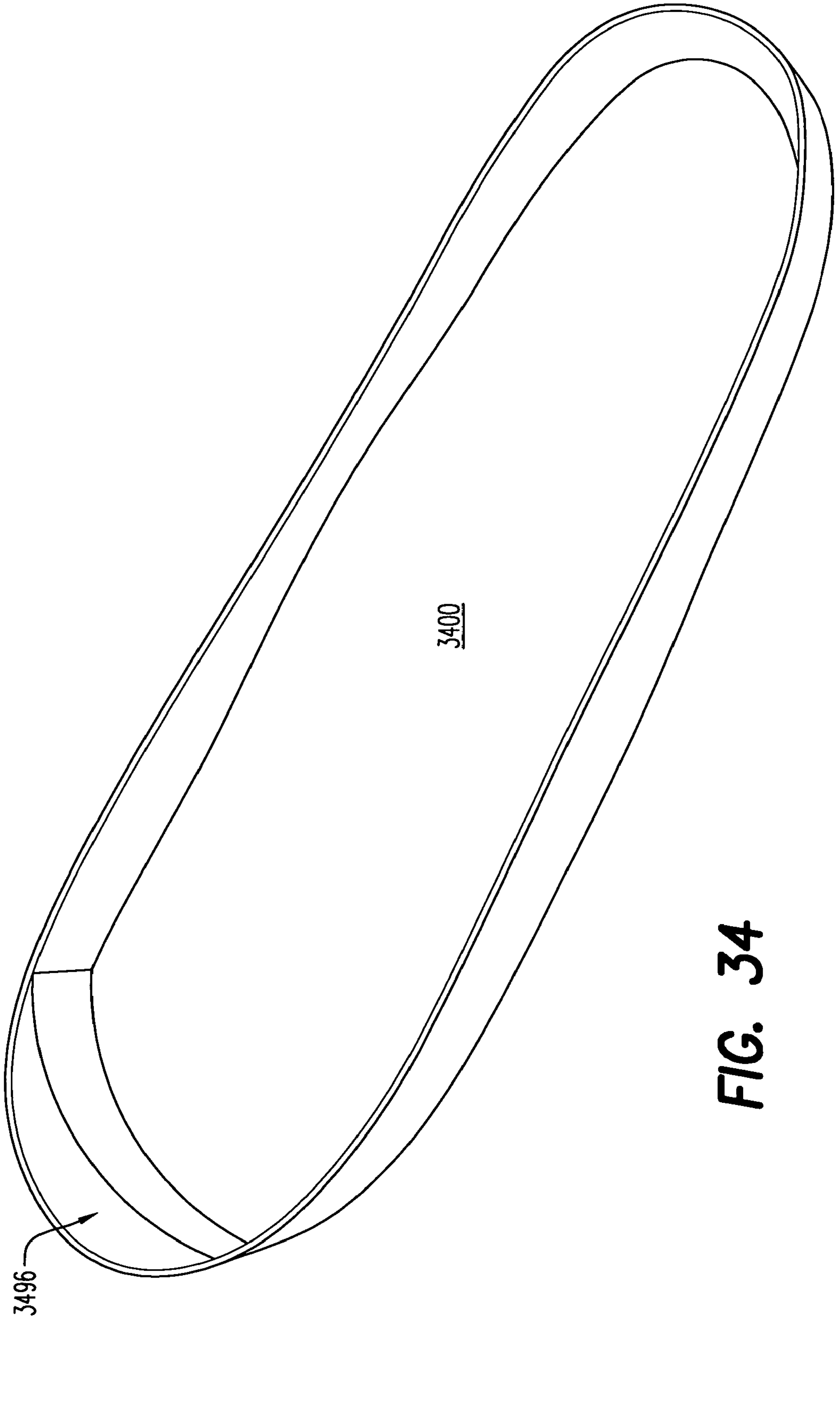
FIG. 34 depicts a midsole with the toe end filled in with solid filler.

FIG. 34 depicts midsole container 3400 with toe end filled in with solid filler 3496. The filler serves the purpose of minimizing extra space to prevent any air from being retained. This in an option, especially in those cases where the toes do not reach the inside end of the midsole. Alternatively, the vacant toe end space fills in with extra beads/particles, if any, when air/liquid is evacuated.

Another aspect includes a self customizing inflatable metatarsal arch support. The arch support includes an airtight shaped metatarsal arch shaped support pad and an attached air line. The support pad is inserted inside a shoe and/or midsole or innersole, so that the air line outlet is positioned outside of the shoe. Air can be forced or allowed into the support pad through the air line to increase support. The device may include open cell foam inside the support pad which is compressed when pressure is added and expands when pressure is released to draw air into the support pad through the air line.

In another aspect, the self customizing inflatable metatarsal arch support is manufactured with the support pad filled with air. A one-way valve is attached to the air line. When pressure over a certain amount, e.g. 1 LB, is applied, air is expelled. When the pressure reaches the comfort support level, the line may be plugged to prevent further air from escaping.

Figure 35:
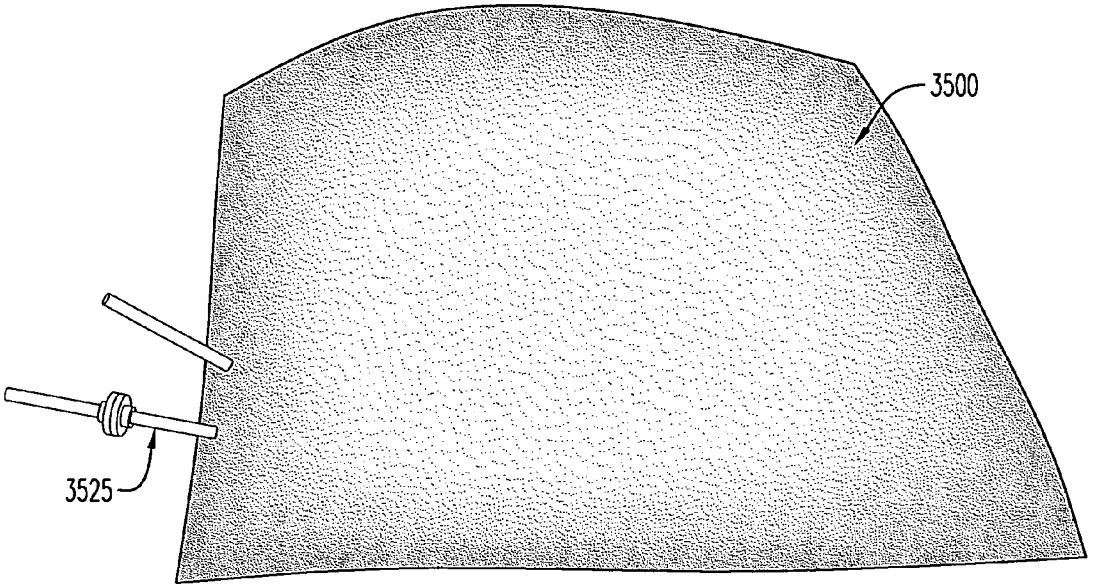
FIG. 35 is a perspective view of an exemplary seat cushion having a dual valve system.

FIG. 35 is a perspective view of an exemplary seat cushion 3500 having a dual valve system 3525. Note that a 3-D impression is not "locked" or captured by seat cushion 3500.

Figure 36:
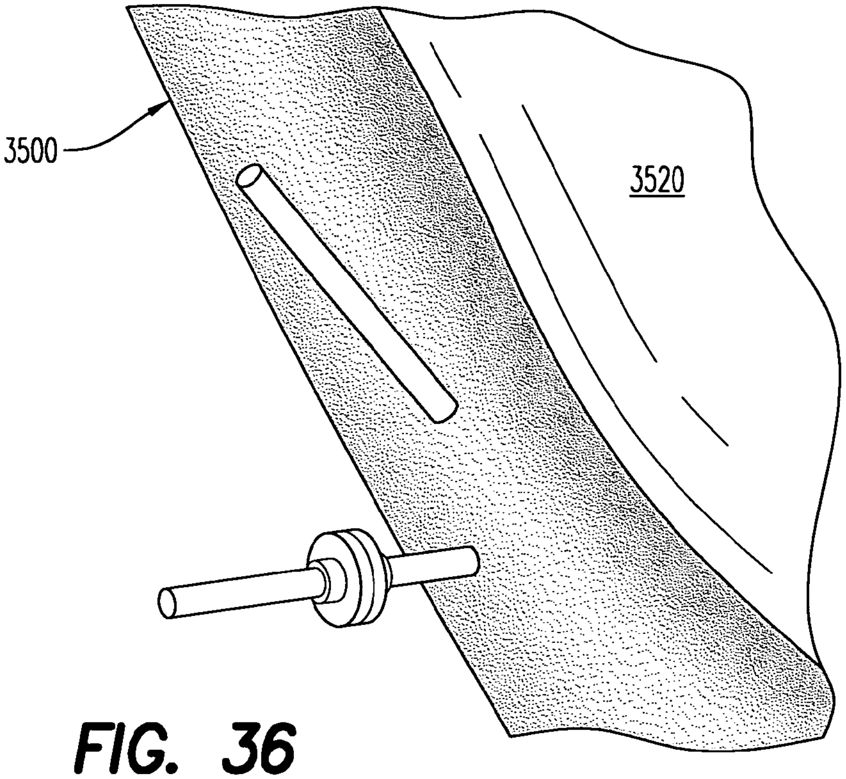
FIG. 36 depicts a perspective view of the exemplary seat cushion of FIG. 35 with a subject object located thereon.

FIG. 36 depicts a perspective view of the exemplary seat cushion 3500 of FIG. 35 with a subject object 3520 located thereon.

Figure 37:
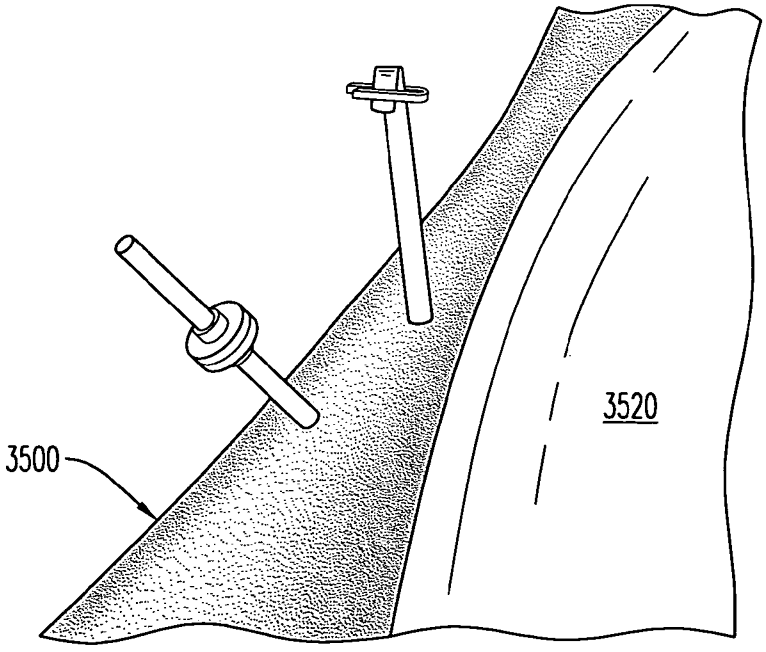
FIG. 37 is a detailed perspective view of the exemplary seat cushion of FIG. 35 with the subject object thereon.

FIG. 37 is a detailed perspective view of exemplary seat cushion 3500 of FIG. 35 with subject object 3520 thereon.

Figure 38:
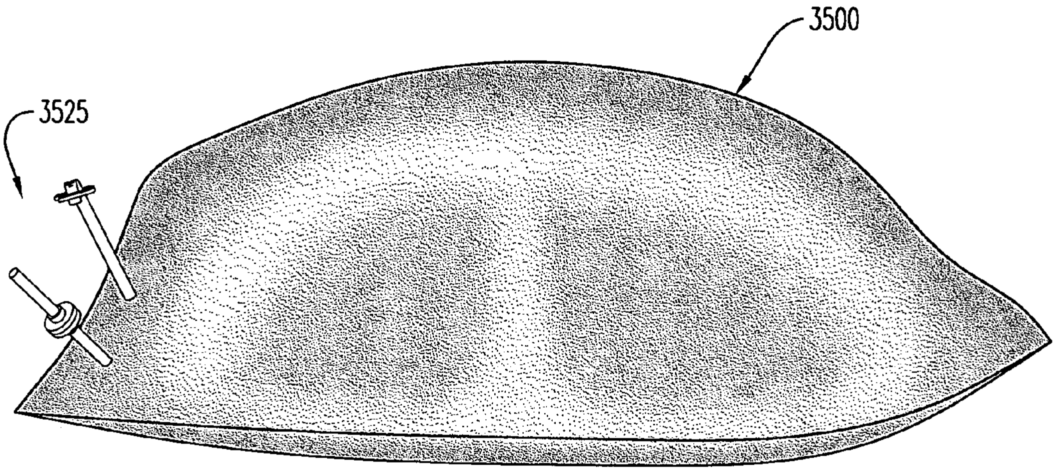
FIG. 38 is a perspective view of an exemplary seat cushion having a dual valve system.

FIG. 38 is a perspective view of exemplary seat cushion 3500 having a dual valve system 3525. Note that a 3-D impression is shown "locked" or captured by seat cushion 3500.

Figure 39:
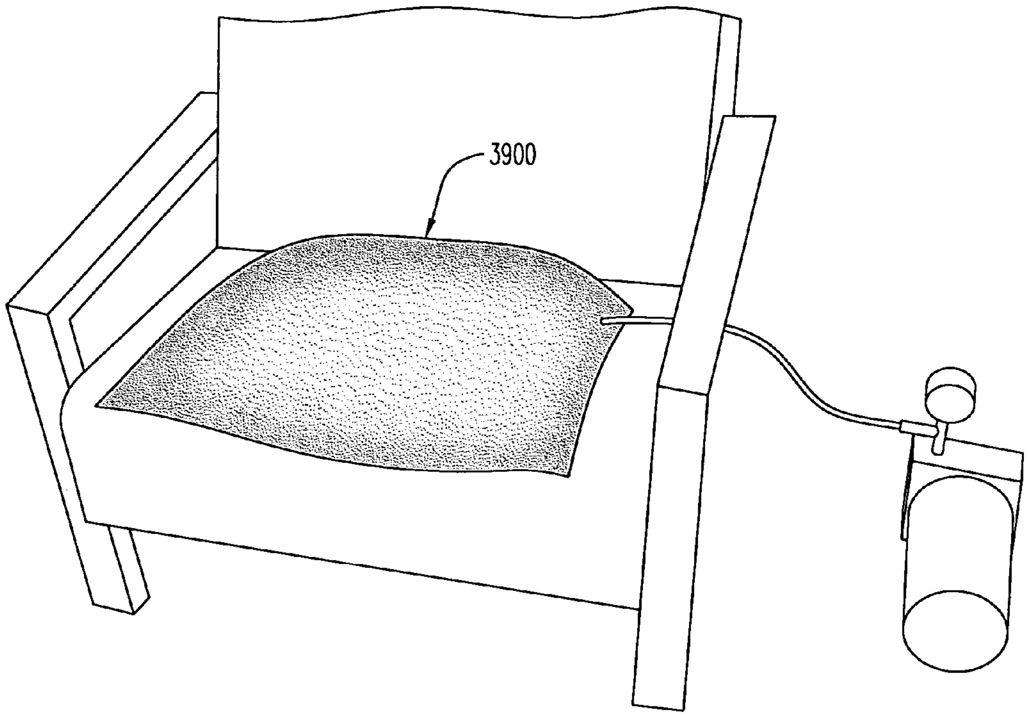
FIG. 39 depicts an exemplary seating cushion interfaced with a vacuum compressor via a supply hose.

FIG. 39 depicts an exemplary seating cushioned 3900 interfaced with a compressor via a supply hose. Seating cushion 3900, containing particles therein, is shown prior to being compressed by a subject object. Seating cushion 3900 may employ the dual valve system discussed hereinabove. Seating cushion 3900 may also include at least a lower back or lumbar support section (not shown).

Figure 40:
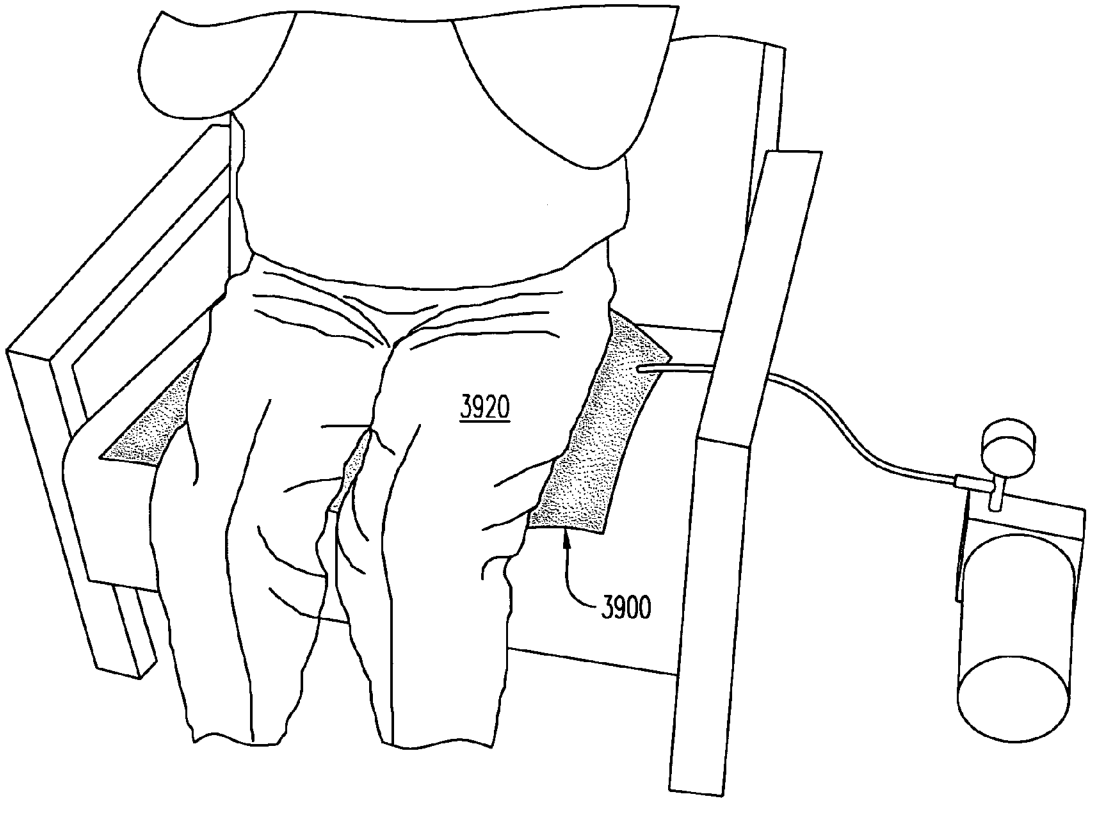
FIG. 40 depicts an exemplary seating cushion employing any one of the 3-D impression systems discussed herein, interfaced with a vacuum compressor via a supply hose.

FIG. 40 depicts an exemplary seating cushion 3900 employing any one of the 3-D impression systems discussed herein, interfaced with a compressor via a supply hose. As shown, the subject object 3920, a person's posterior end, is seated on seat cushion 3900 containing the particles and gas (e.g., air).

Figure 41:
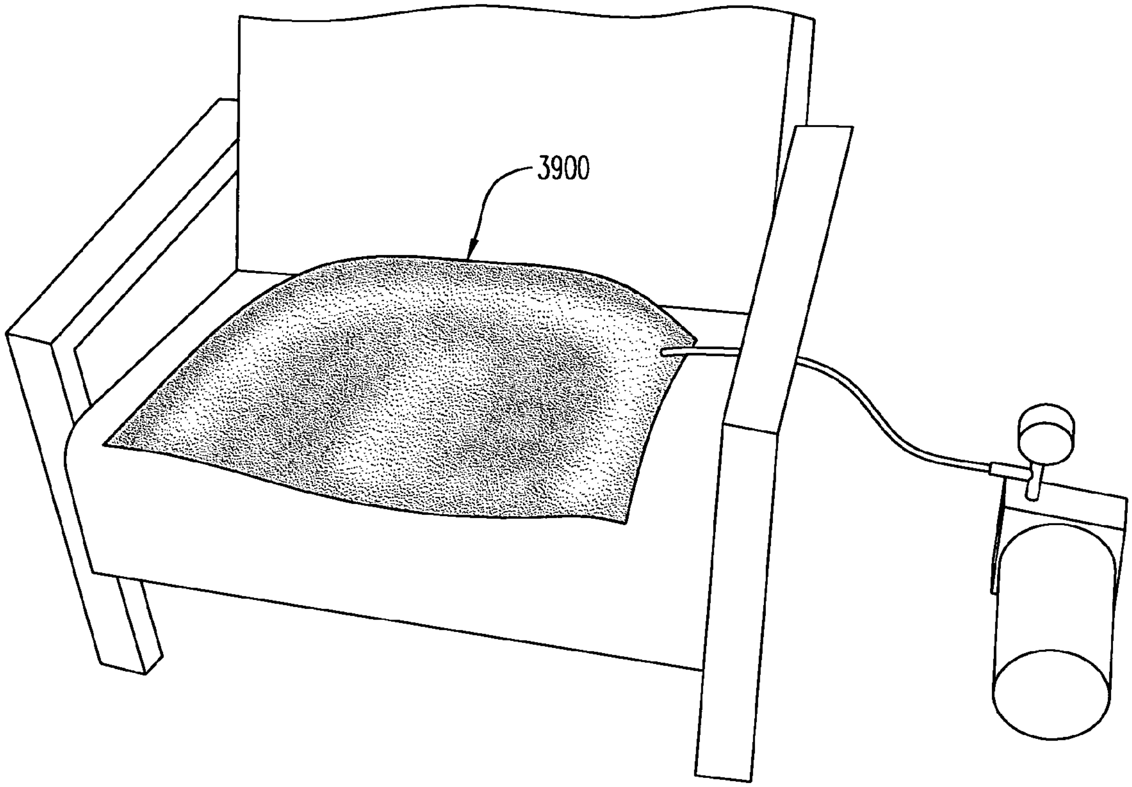
FIG. 41 depicts the exemplary seat cushion of FIG. 39, after the subject object has forced a certain volume of the gas from the seat cushion.

FIG. 41 depicts the exemplary seat cushion of FIG. 39, after the subject object has forced a certain volume of the gas from the seat cushion. Visible in FIG. 41 is the captured 3-D impression of the user's posterior end in the seat cushion.

In another aspect, the seat cushion includes an electronic control system where the air, vacuum lock system is at least partially controlled with a heat sensor. When the temperature of the seat cushion is above a desired level, the sensor may trigger air valves to open and permit fresh air to enter the seat cushion. Air can also be forced in by a suitable pumping device such a compressor. In an example of a seat cushion used in a vehicle, the compressor from the vehicle's engine may be utilized. In the example of a wheelchair cushion, a compressor may be positioned on the wheelchair. A remote control may also be used in a wheelchair system to set and release the seat contour.

In another aspect for use in a midsole/insole, seating configuration, or other configuration, an interior airtight covering or skin covers an inside container. For example, in a seating configuration, an outer covering such as a leather covering may not be airtight. An airtight skin or covering layer, such as a vinyl material, may be used. Use of a separate covering allows air to be circulated without "erasing" the contour of the seat.

In another aspect hereof, a golf club (and other exercise equipment and sporting goods having a gripping handle or portion) may include a handle coupled to and/or part of a 3-D capture system for providing a personalized grip. An intake and/or output valve (implemented as either a single valve, a combination valve, or two discrete valves) can be unobtrusively incorporated into the shaft of the, for example, golf club. The input and/or output valve(s) are preferably located in a distal end of the shaft or at any point along the length of the shaft. The valve may be connected to the club shaft by being screwed, friction fitted, snap-fitted or otherwise operatively coupled to the club shaft. The valve may also be plugged to prevent leaks.

Regarding the valve mechanism, the valve may have an external manually operated air flow control mechanism or an internal automated valve mechanism. The valve mechanism is provided to allow the passage of the gas and/or liquid into and/or out of the hand grip.

Figure 42:
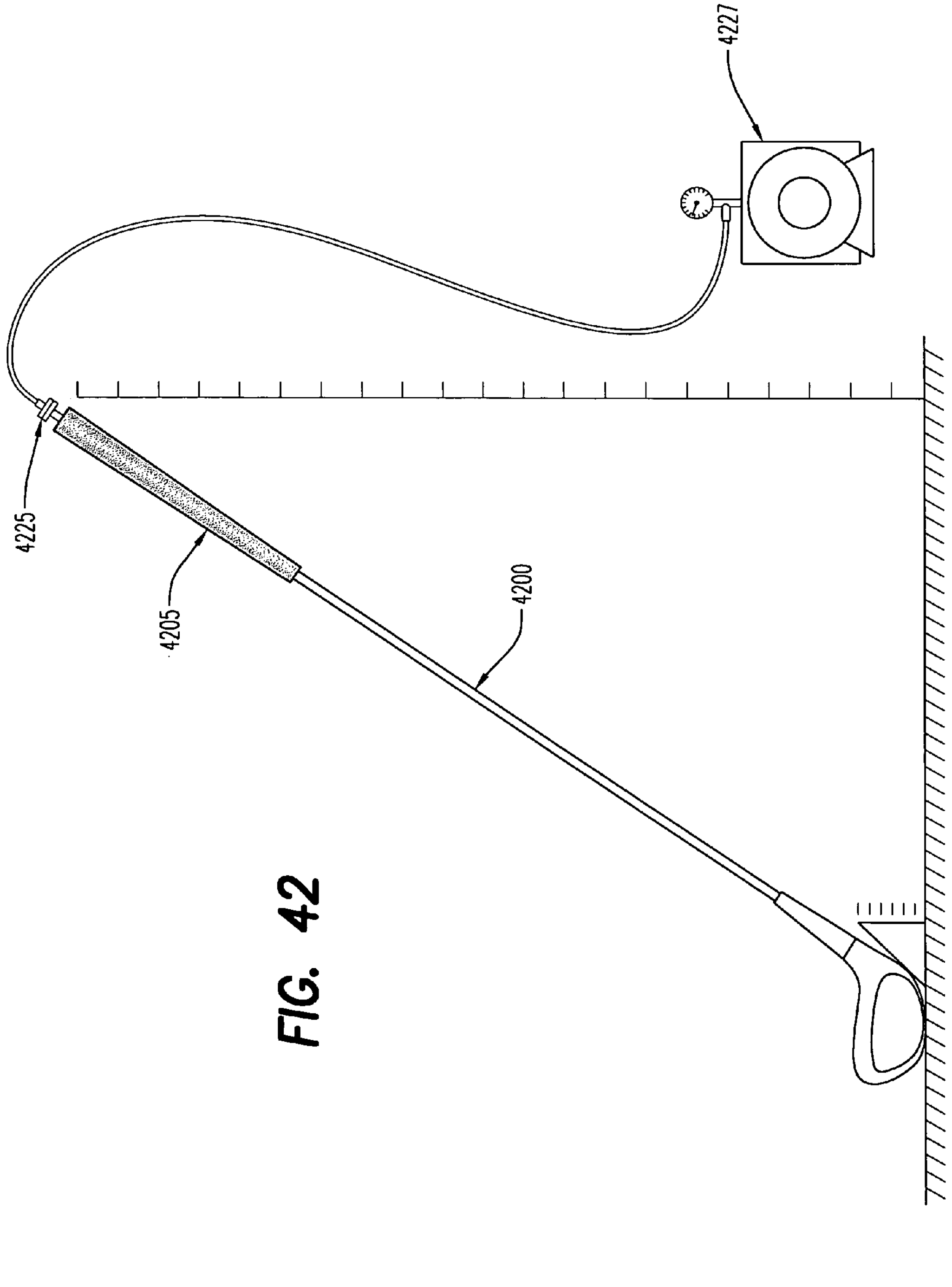
FIG. 42 shows a golf club having a hand grip loaded with particles and a volume of liquid and/or gas therein positioned on a golf club shaft.

FIG. 42 shows a golf club 4200 having a hand grip 4205 loaded with particles and a volume of liquid and/or gas therein positioned on a golf club shaft. A valve 4225 is located at the proximal end that is operatively gripped by a golfer. The particles are preferably about 1 mm to about 2 mm in diameter, though other sizes of particles may be used. As shown, exemplary golf club 4200 is interfaced with a vacuum compressor 4227 for removing at least a portion of the liquid and/or gas from the particle loaded hand grip 4205.

The shaft of the golf club being fitted with the particle-filled hand grip may be modified internally such that the vacuum line introduce to the interior of the golf club shaft is in clued communication with the particle-filled hand grip. This may be accomplished making at least one aperture, and preferably multiple, in the golf club's shaft in the area covered by the particle-filled hand grip. As shown, the hand grip is sealed at a distal end thereof by a clamp or other method/device at sealed at the proximal end by the hand grip. The hand grip may have a valve located at the proximal end for connecting to the vacuum compressor. The valve can be located at the proximal end of the club shaft by sealing a hollow club shaft with an end cap having a valve port or aperture located therein for receiving the valve that is connected to the vacuum supply line. The clamp and valve operate to provide a sealed environment that can be sufficiently vacuumed to capture a 3-D impression made in the particle-filled hand grip.

The hand grip device hereof also provides the benefit of reducing shock to the user of the club, bat, tool, racquet, firearm, etc. The shape of the particles, for example beads 2 mm in diameter and greater, tend to disperse the force of an impact shock laterally, thus limiting the force transferred to the user. The shape, size, and material of construction of the particles can be varied to enhance the shock absorbency and/or shock dispersing characteristics of the hand grip.

Although the internal surface of the hand grip preferably mimics the surface area of the club's shaft, the hand grip need not follow the size and shape of the club shaft exactly. For example, in the instance of a tapered club shaft, the hand grip may not taper, at least to the extent of the club's shaft. The tapering hand grip can be limited to preserve a sufficient volume in the hand grip for the particles disposed therein in the area of the tapered shaft.

In one aspect, a layer, preferably a thin layer, of memory intensive material such as, for example, urethane foam can be placed or laminated to an underside of the hand grip's outer cover (i.e., skin). The memory intensive material provides an added layer of impression capturing material on top of the particles. The memory intensive material preferably adds to the gripping comfort of the grip handle.

The hand grip, at least the outer contact surface (i.e., skin) thereof, may be constructed of a leather, vinyl, urethanes, etc.

In an aspect hereof, only a portion of the shaft is subject to the vacuuming power of the vacuum compressor connected to the golf club shaft. For example, only that portion of the golf club shaft covered by the handle grip is subject to the vacuuming pressure. This may be accomplished dividing the golf club shaft into at least two sections using air and liquid-tight seals.

In an aspect herein, the golf club handle including the 3-D capture system may be applied to new golf clubs during the manufacture thereof or applied to retro-fit previously used golf clubs.

The golf handle of the present invention can be implemented as a flexible handle grip having particles contained therein. The shaft of the golf club may be used a conduit for vacuuming the air from the flexible hosing of the particle-filled hand grip placed on the shaft of the golf club. To facilitate such a vacuuming operation, a number of air passage holes can be made in the golf club shaft, in fluid communication with an inner surface of the particle-filled hand grip. Thus, when the vacuum pressure is applied through a valve connected to the shaft of the golf club, air can then be drawn out of the particle-filled handle grip, thereby capturing a 3-D contour impression of the golfer's grip.

The 3-D impression taking process may be improved by using a vibrator to stimulate (e.g., vibrate) the particles. In this manner, a higher resolution impression may be obtained.

A bead port may be provided to further customize the hand grip be providing an input/extraction port for adding and removing, respectively, additional particles to the hand grip.

The golf club embodiment may include a dual valve system for providing the capability of selectively capturing and erasing the captured 3-D impression until an acceptable impression is obtained, as discussed hereinabove with regard to the dual valve system.

In another aspect of the golf grip embodiment, the flexible housing of the handle grip may be constructed as layers of a sheet-like material having particles disposed therebetween. The sheet-layered, particle filled flexible housing is then wrapped around the shaft of the golf club and secured thereto by any number of methods such as an adhesive, hook and loop fasteners, etc. The layered configuration of the hand grip may have the particles therein located in partitions of the flexible housing. The inner surface of the hand grip that opposes the golf club shaft may be perforated to allow the passage of liquid and/or gas therethrough under the influence of the vacuum compressor. In this embodiment, the vacuum line is placed between the top layer of the hand grip and the bottom layer of the hand grip, thus obviating the need to modify the shaft of a conventional golf club.

The golf club is shown juxtaposed with a scale that is referenced in the "fitting" of the golf club to the user. As shown in FIG. 42, there is a scale for determining the angle between the golf club's shaft relative to the floor or ground (i.e., a reference surface), and a scale for determining the angle between the golf club's head relative to the floor or ground (i.e., a reference surface). Additionally, a reference scale can be used to determine and fix the angle between the club shaft and the golfer's body and/or arms when the golfer is in position for addressing a golf ball.

To facilitate the fitting of the golf club to the individual golfer, a holder, block, and/or guide may be used to assist in determining and maintaining the golf club in a desired position to "fit" the individual golfer.

Optionally, a thumb positioning mark or reference may be placed on the hand grip the provide a tactile and/or visual cue to alert the golfer that their hands are properly aligned with, preferably, the center of the club's head. By virtue of properly aligning their hands with the club, a club that is preferably fitted to the golfer, there is an increased likelihood that the golfer is properly aligned with the golf club to execute a properly aligned golf shot. The thumb positioning mark may have reference indicators for one or both thumbs of the users hands. Optionally, grooved gripping channels may be used as an aid in providing tactile and visual cues for alignment of the user's hands on the hand grip.

The desired and proper alignment of the thumb positioning mark or reference relative to the club's head can be maintained by gluing, pinning, screwing, clamping, or otherwise affixing to the shaft of the club so as to prevent a change in the relative position between the club head and the thumb positioning mark. In one aspect hereof, a slip-resistant material such as a rubber layer of material having a coefficient of drag greater than the club's shaft is disposed between the club's shaft and the hand grip. The slip-resistant layer of material provides additional drag and thus tends to resist the turning of hand grip on the club's shaft.

The grip handle may be partitioned internally to maintain a certain volume of the particles within the various partitioned sections thereof. This provides, for example, a substantially uniform distribution of the particles over the are of the grip handle.

Once the golf club is properly gripped and aligned by the golfer, using the scales shown as reference markers, the excess liquid and/or gas is vacuumed out using the compressor. In this manner, the golf grip handle locks in a placeholder for the golfer's hands in the proper "aligned" position. Therefore, the locked 3-D contour of the golfer's grip obtained by the 3-D compression capture system herein can be used as an alignment mechanism for aligning the golfer in not only the proper grip, but the overall aligned and proper golf swing alignment position.

The grip handle may also be partitioned into two separate component grips, which may minimize excess space in the grip. This embodiment may make it easier to evacuate air/liquid that is not directly under the hand during fitting. In this embodiment, each of the two component grips may have its own valve system.

Figure 43:
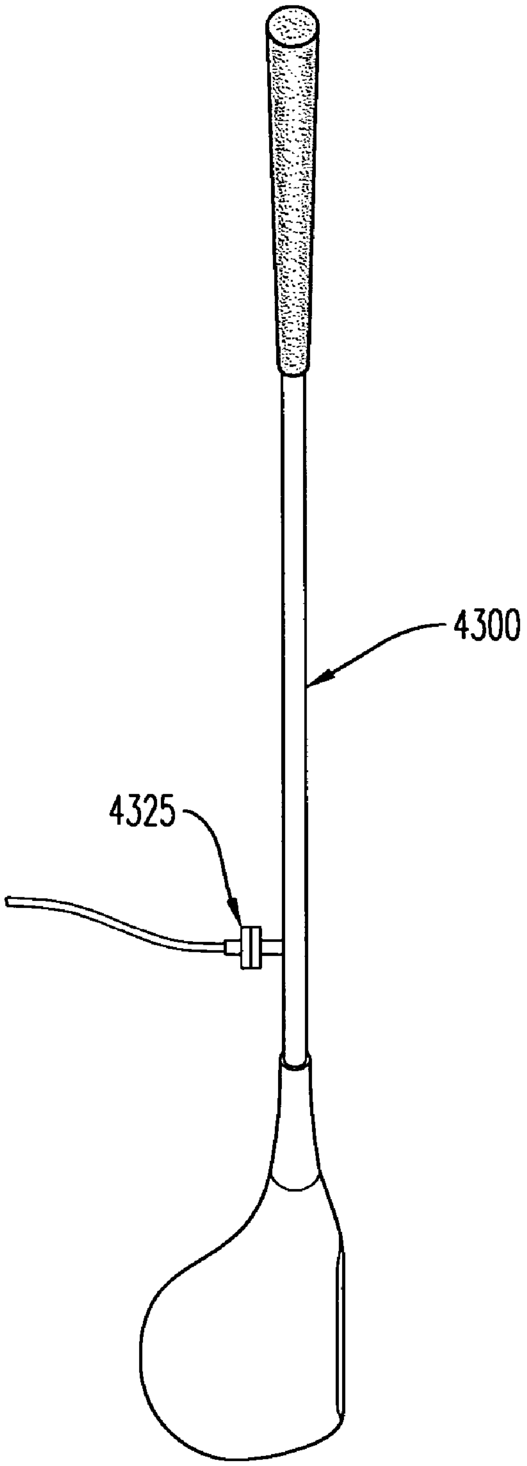
FIG. 43 shows a golf club wherein the valve is located at a position along the shaft of the golf club.

FIG. 43 shows a golf club 4300 wherein a valve 4325 is located at a position along the shaft of golf club 4300.

Although the hand grip is discussed primarily in the context of a golf club grip, the grip handle may be applied to a golf club, a baseball bat, an archery bow, all forms of sport racquets, ski pole handles, pole vault poles, race car steering wheels, bicycle handlebars, a firearm handle (e.g., a pistol grip), power tools, hand tools, etc.

A benefit of the customized grip handle is that the personalized grip handle having the 3-D impression contour of the user's hands in an optimum, aligned position can be used to guide the user's hands to the proper positioning location each time the user picks up the golf club. In the event the user's optimum alignment position changes and/or needs correcting, the current impression can be erased by re-introducing a volume of liquid and/or gas into the grip handle and then making a new 3-D impression of the user's grip.

Figure 44:
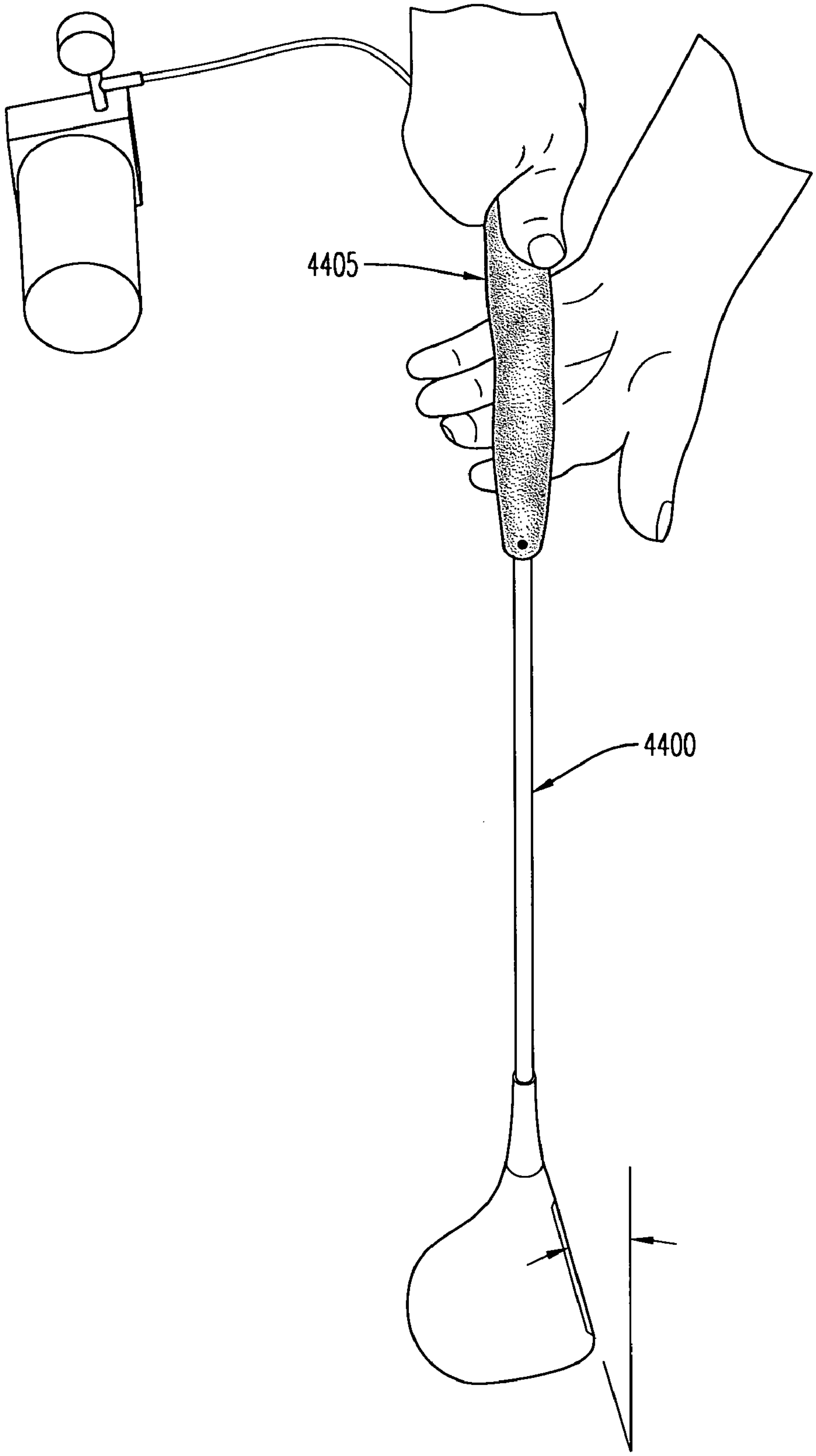
FIG. 44 shows an exemplary golf club with the club head centered to a ground reference mark, and the shaft angle to the ground and to the club holder.

FIG. 44 shows an exemplary golf club 4400 with the club head centered to a ground reference mark, and the shaft angle to the ground and to the club holder. The thumb positioning reference is made on a grip handle 4405 after the angle of the club shaft and head are fitted to the golfer and an impression is made. Of note, the thumb positioning reference is centered to the golf head. In the event the impression is erased, the thumb positioning reference marks can be used to obtain the proper hand alignment with club 4400 prior to taking a new impression. In this manner, the "fitting" of club 4400 will not have to be repeated.

Figure 45:
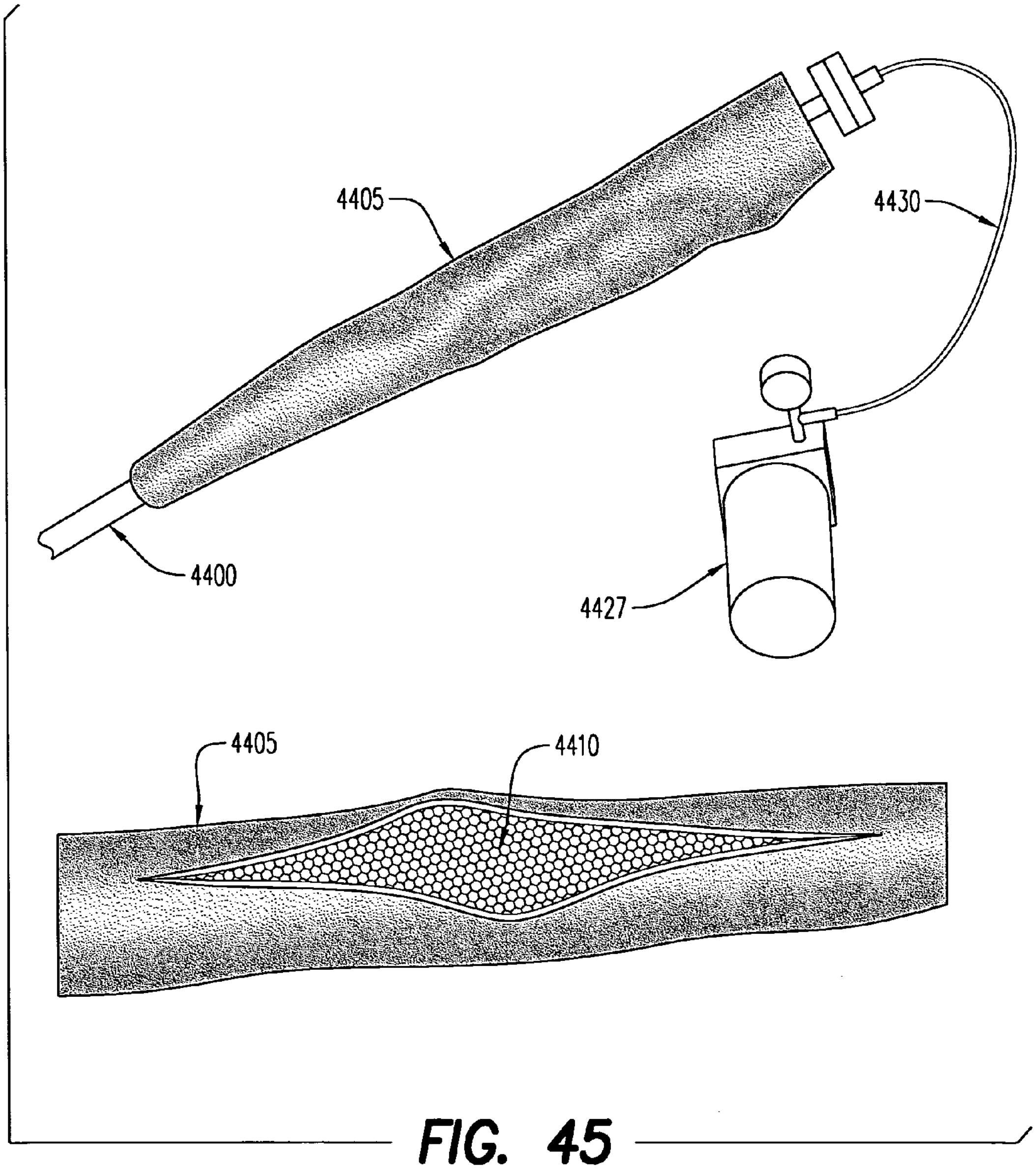
FIG. 45 depicts an exemplary view of the golf club connected to a vacuum compressor supply line at the proximal end of the golf club shaft.

FIG. 45 depicts an exemplary view of golf club 4400 connected to a vacuum compressor 4427 via a supply line 4430 at the proximal end of the golf club shaft. Also shown are impression markings on grip handle 4405. Also shown is a detailed view of grip handle 4405, with the internal particles 4410, here beads, visible.

Figure 46:
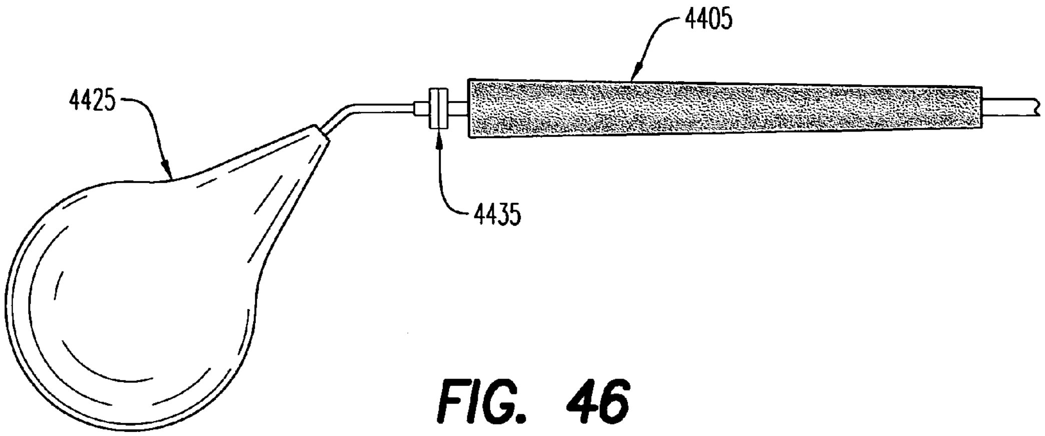
FIG. 46 depicts a schematic of a manual mechanical pump for removing air from the hand grip. The valve may be a one-way check valve.

FIG. 46 depicts a schematic of a manual mechanical pump 4425 for removing air from hand grip 4405. Valve 4435 may be a one-way check valve.

Figure 47:
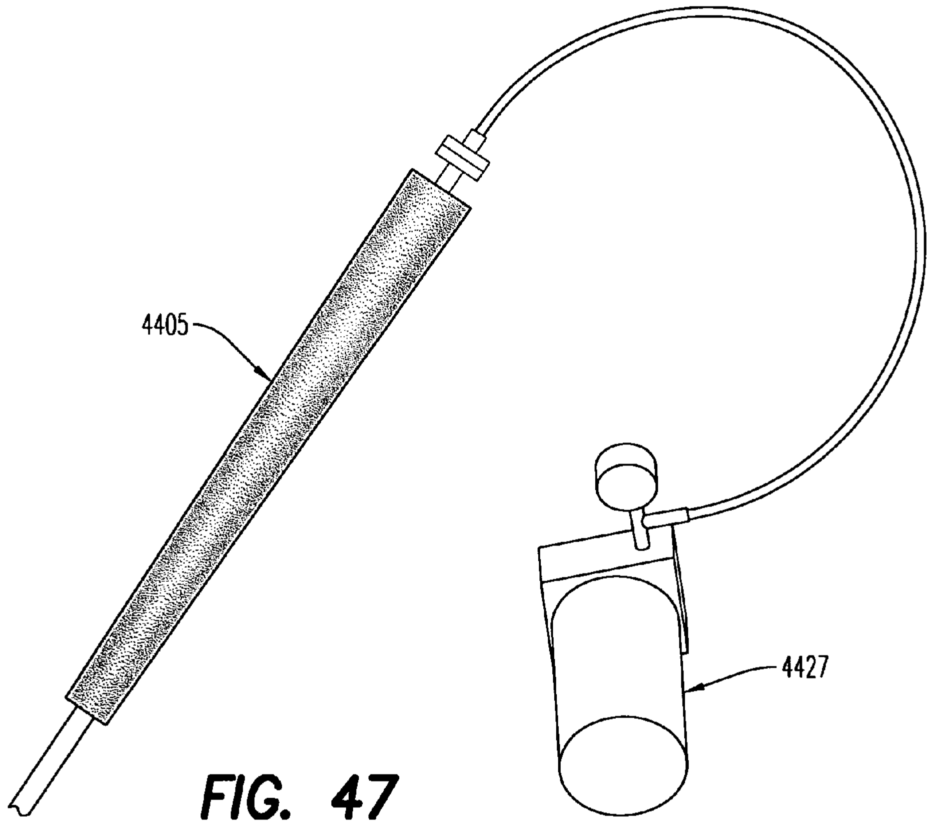
FIG. 47 depicts a schematic of the hand grip connected to a vacuum compressor connected to the hand grip for removing air from the hand grip.

FIG. 47 depicts a schematic of hand grip 4405 connected to vacuum compressor 4427, which is connected to hand grip 4405 for removing air from hand grip 4405.

Figure 48:
FIG. 48 depicts a conventional golf club grip handle.

FIG. 48 depicts a conventional golf club grip handle 4802.

Figure 49:
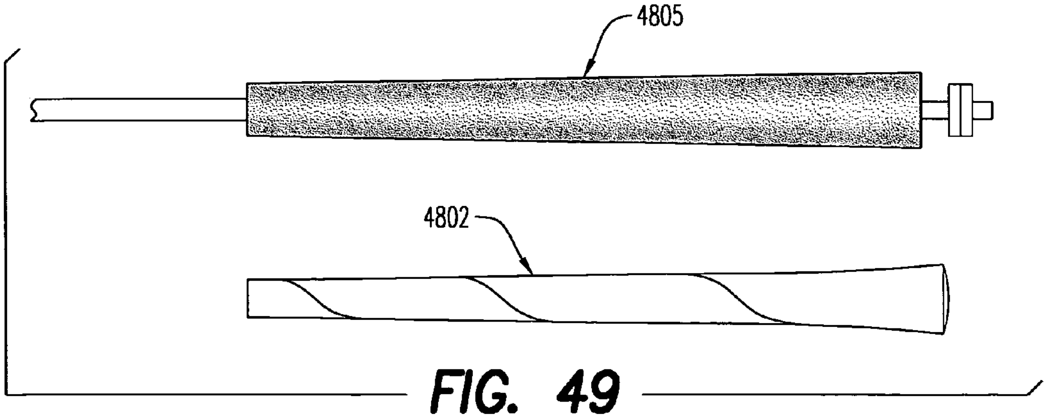
FIG. 49 depicts both a conventional golf club grip handle and the grip handle hereof that provides a 3-D impression of a user's proper, aligned hand position.

FIG. 49 depicts both conventional golf club grip handle 4802 and a grip handle 4805 hereof that provides a 3-D impression of a user's proper, aligned hand position.

Figure 50:
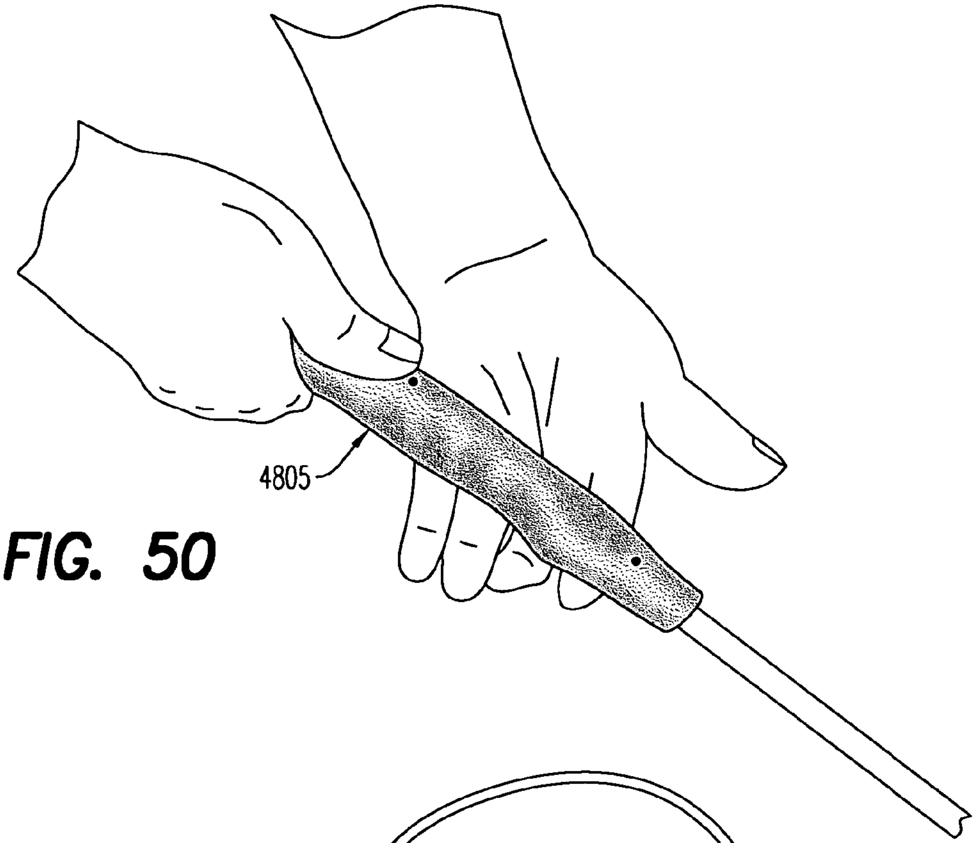
FIG. 50 depicts an exemplary grip handle hereof, including a detailed view of the two thumb reference marks thereon.

FIG. 50 depicts exemplary grip handle 4805 hereof, including a detailed view of the two thumb reference marks thereon.

Figure 51:
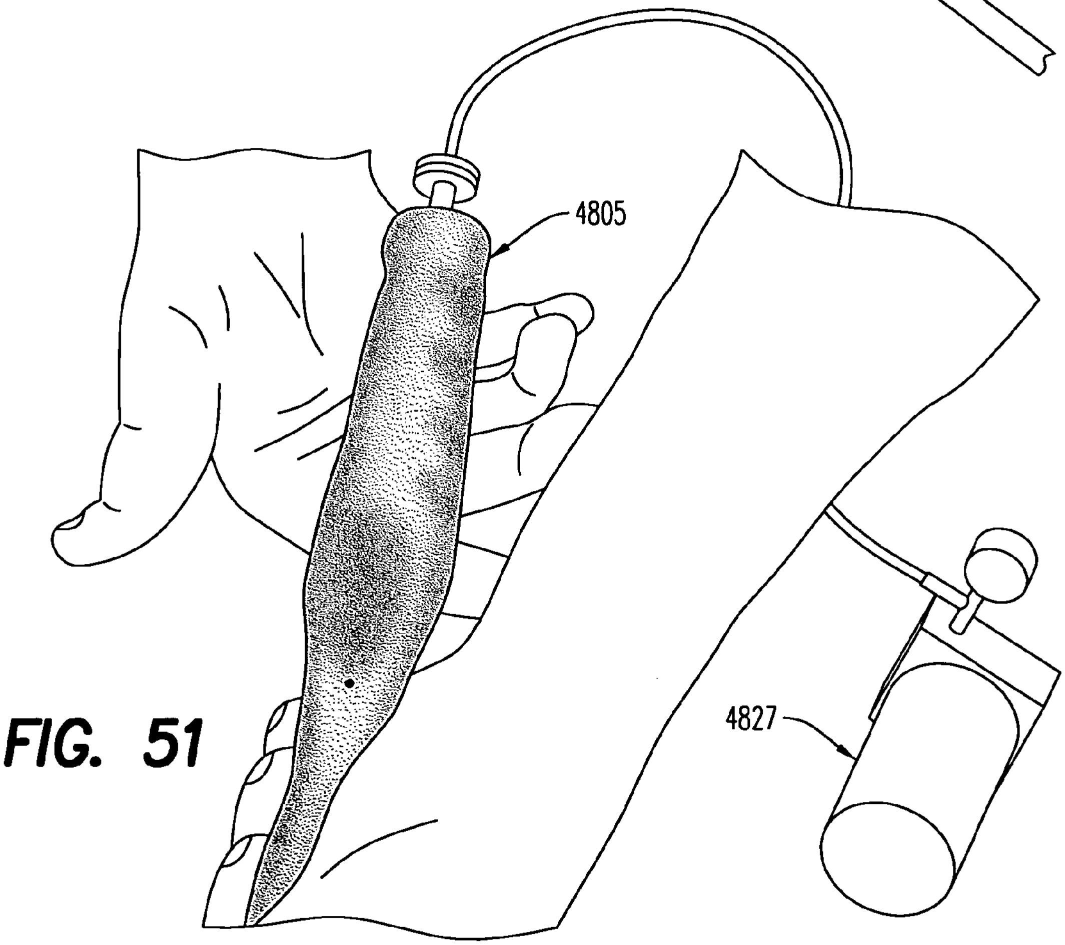
FIG. 51 depicts an exemplary grip handle hereof, including a detailed view of the upper thumb reference mark and the vacuum compressor supply line connection.

FIG. 51 depicts exemplary grip handle 4805 hereof, including a detailed view of the upper thumb reference mark and the vacuum compressor 4827 supply line connection.

Figure 52:
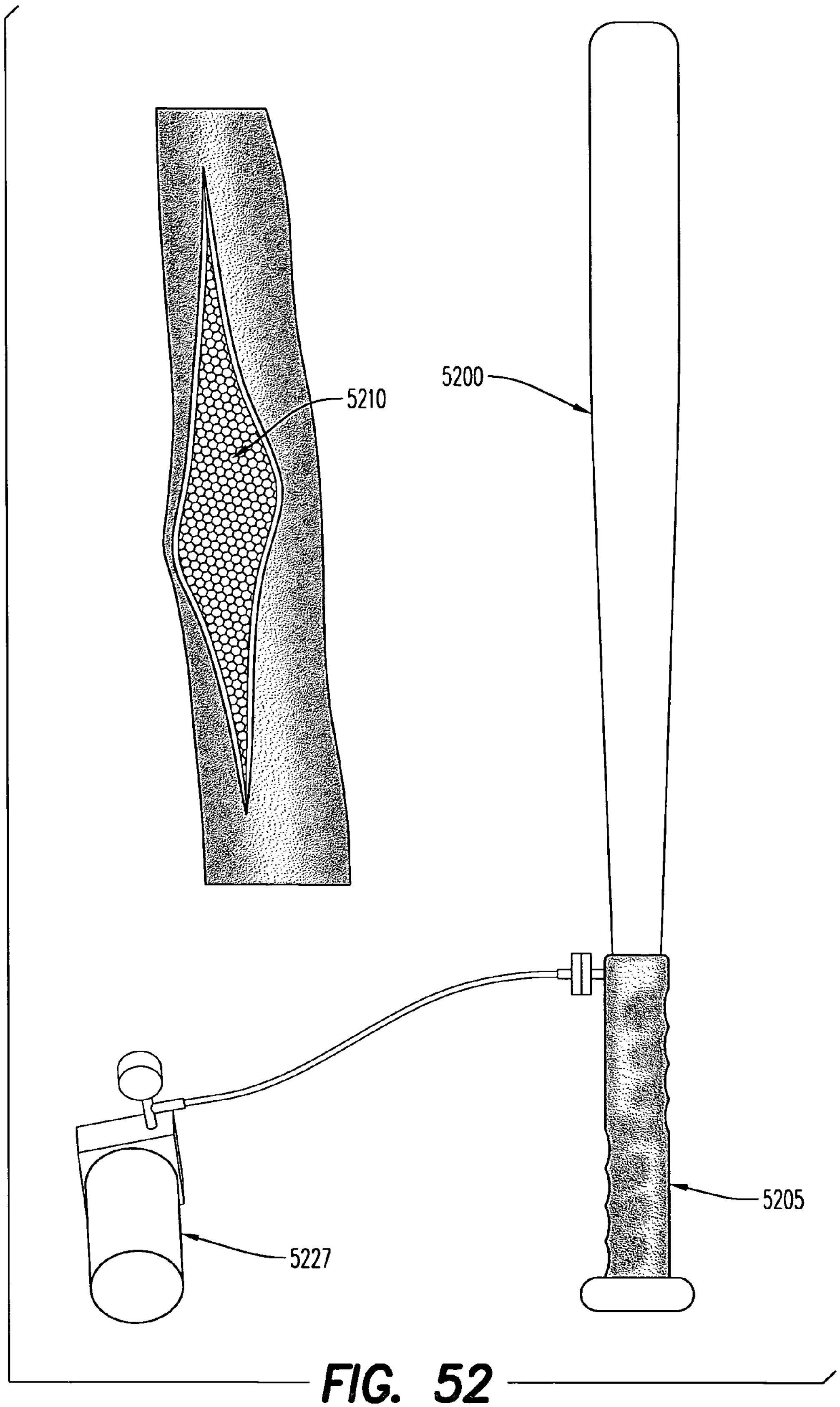
FIG. 52 depicts a baseball bat having a handle end thereof fitted with a grip handle of the present teachings.

FIG. 52 depicts a baseball bat 5200 having a handle end thereof fitted with a grip handle 5205 of the present teachings. Grip handle 5205 is shown connected to a vacuum compressor 5227. Also shown, there is a detailed view of beads (particles) 5210 disposed on the interior of grip handle 5205.

In the instance of a wood baseball bat, it is preferable that a reference mark for aligning the user's hands with the handle of the bat considers the grain of the bat. The hands should be positioned on the bat during the 3-D impression making process so that when the bat is gripped per the 3-D impression, the grains of the wood bat are aligned to minimize the risk of breaking the bat when hitting a baseball.

Figure 53:
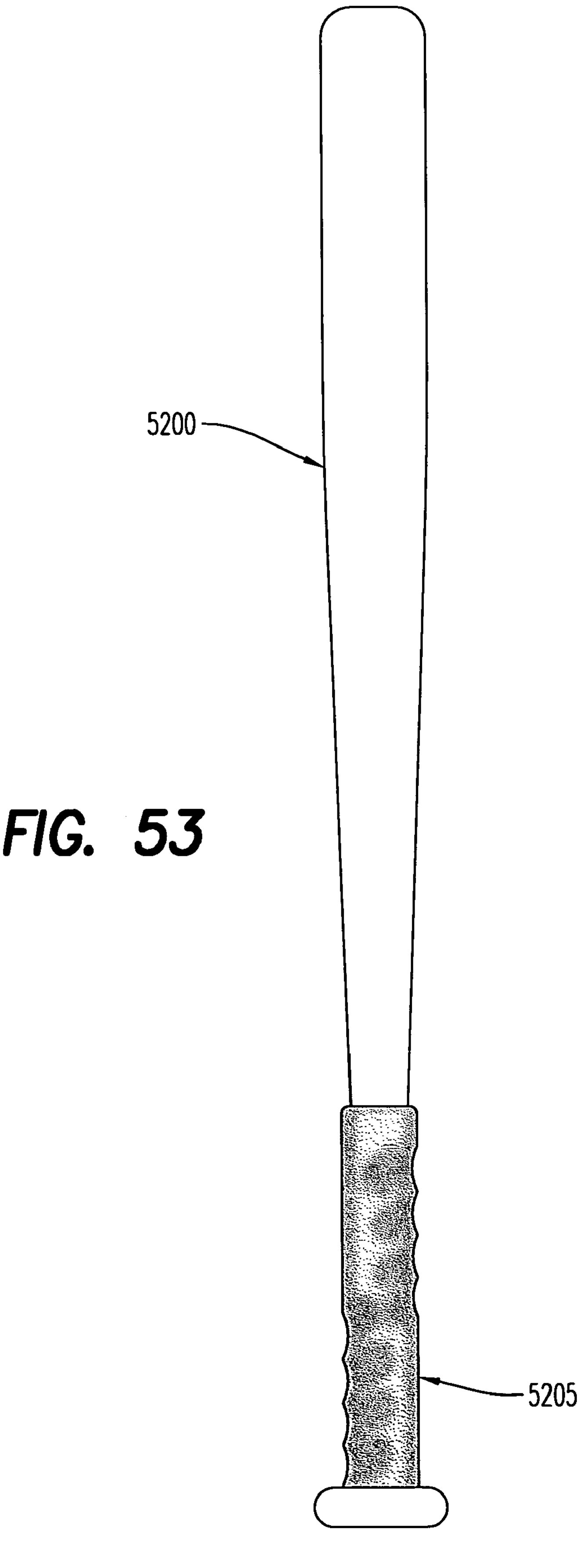
FIG. 53 depicts the baseball bat of FIG. 52, with a locked 3-D impression in the grip handle.

FIG. 53 depicts baseball bat 5200 of FIG. 52, with a locked 3-D impression in grip handle 5205.

Figure 54:
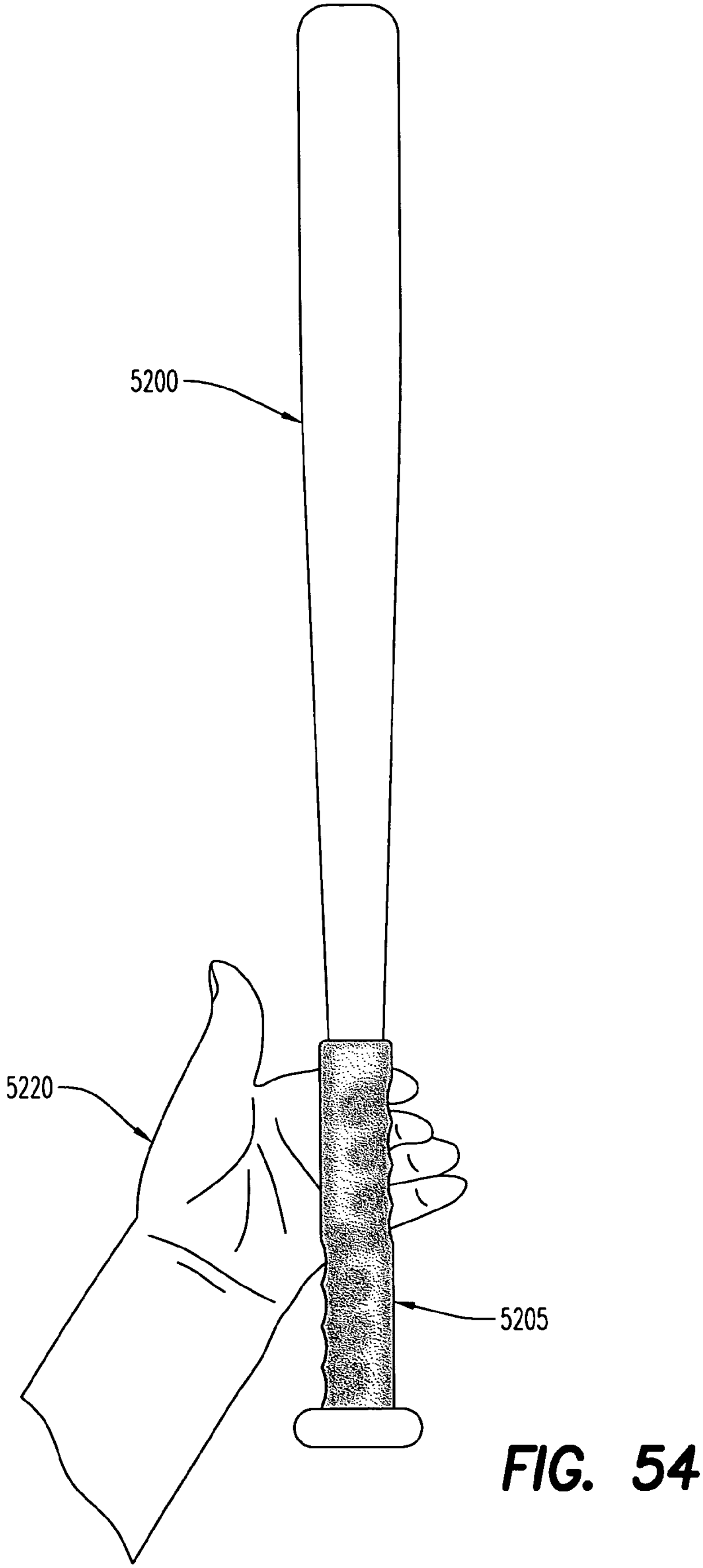
FIG. 54 depicts the baseball bat of FIG. 52, juxtaposed with the hand of a user to illustrate the custom fit obtained by the personalized grip handle hereof.

FIG. 54 depicts baseball bat 5200 of FIG. 52, juxtaposed with a hand 5220 of a user to illustrate the custom fit obtained by personalized grip handle 5205 hereof.

The claims appended hereto complement and further disclose the teachings of the present invention. The entirety of the application is to be considered regarding the scope, intent and disclosure of the present application. For instance, the method of the present invention for measuring a plantar contour of a foot and the method of obtaining a 3-D contour of a subject object in general include all of the various aspects of the disclosed devices. That is, the methods of the present invention are completely and fully compatible with the devices of the present invention. The term particles includes, but is not limited to, beads fibers, particles, and strands.

What is claimed is:

1. A three-dimensional (3-D) capture system comprising:

a flexible housing defining a reservoir therein;

a plurality of particles disposed in said reservoir; and a gas and/or liquid disposed in said reservoir;

wherein one or more areas of said housing are restricted from particle migration.

2. The system according to claim 1, further comprising a valve assembly in communication with said reservoir for regulating a quantity of said gas and/or liquid disposed in said reservoir, wherein said regulating includes removal of at least a portion of said gas and/or liquid in response to pressure on said reservoir, and wherein said housing substantially retains a contour formed by said pressure after said pressure is removed.

3. The system according to claim 2, wherein said valve assembly comprises a unidirectional valve to control a flow of said gas and/or liquid.

4. The system according to claim 3, wherein said unidirectional valve includes a bypass capability to allow said gas and/or liquid to be selectively reintroduced into said housing.

5. The system according to claim 2, further comprising a plug to prevent leaks of said gas and/or liquid through said valve assembly.

6. The system according to claim 2, wherein said valve assembly comprises two or more valves.

7. The system according to claim 2, wherein said valve assembly comprises an output valve and an input valve.

8. The system according to claim 2, further comprising an electronic control system to control an opening of said valve assembly.

9. The system according to claim 8, wherein said electronic control system includes a processor and a battery.

10. The system according to claim 8, further comprising a remote control device to activate said control system.

11. The system according to claim 8, wherein said control system is voice activated.

12. The system according to claim 8, further comprising a heat sensor, wherein said heat sensor activates said control system when said system exceeds a selected temperature to allow said gas and/or liquid to enter said housing and cool said housing.

13. The system according to claim 8, further comprising a shielding layer to prevent damage to said control system due to static charges.

14. The system according to claim 2, wherein said gas and/or liquid is selected from the group consisting of an adhesive, water, and air.

15. The system according to claim 2, wherein said valve assembly has an end opening smaller than said particles.

16. The system according to claim 1, wherein said particles are elastomeric.

17. The system according to claim 1, wherein said particles are solid.

18. The system according to claim 17, wherein said valve assembly has an end opening that includes a screen to prevent particles from entering said valve assembly.

19. The system according to claim 1, wherein said particles are of a shape selected from the group consisting of spherical, cylindrical, randomly shaped, and any combination thereof.

20. The system according to claim 1, wherein the particles are of a size from about 0.1 mm to about 10 mm.

21. The system according to claim 1, wherein said particles comprise more than one density.

22. The system according to claim 1, wherein said particles comprise more than one hardness.

23. The system according to claim 1, wherein said particles are doped with an adhesive.

24. The system according to claim 1, wherein said particles are lubricated with a high viscosity material.

25. The system according to claim 1, wherein said particles are anti-static.

26. The system according to claim 1, wherein at least a portion of said particles can be fused together by an appropriately calibrated energy source.

27. The system according to claim 26, wherein said energy source is selected from a heater and a microwave device.

28. The system according to claim 1, wherein said reservoir has opposing surfaces selectively bonded together by a barrier to form at least two partitions to limit a migration of said particles between said at least two partitions.

29. The system according to claim 28, wherein each of said at least two partitions are filled with particles having different characteristics.

30. The system according to claim 1, wherein said housing further comprises, optionally, at least one mid layer, and an at least one top outer layer, wherein said at least one mid layer is disposed between said particles and said outer layer.

31. The system according to claim 30, wherein said mid layer is a mesh-type screen.

32. The system according to claim 1, wherein said housing forms a seating surface.

33. The system according to claim 1, wherein said housing has a seating surface, which seating surface is used in an application selected from the group consisting of a chair, a wheelchair, a plane, a bicycle, a motorcycle, a train, an automobile, a bus, and a mattress topper.

34. The system according to claim 1, further comprising a pump for pumping said gas and/or liquid.

35. The system according to claim 1, further comprising a vacuum system for said gas and/or liquid.

36. The system according to claim 1, wherein said housing is configured to support a human foot.

37. The system according to claim 1, wherein said system is integral to footwear.

38. The system according to claim 1, wherein said system is integral to a helmet.

39. The system according to claim 1, wherein said system is integral to a gripping device.

40. The system according to claim 1, wherein at least a portion of said housing is elastic.

41. The system according to claim 1, wherein at least some of said particles are fibers.

42. The system according to claim 1, further comprising pre-shaped sections in said reservoir for retaining subsets of said particles having differing binding characteristics, wherein each of said sections is connected to an individual valve assembly for selectively controlling a flow of the gas and/or liquid thereto.

43. The system according to claim 1, further comprising pre-shaped sections in said reservoir, wherein a barrier between adjoining partitions permits the flow of said gas and/or liquid therethrough.

44. The system according to claim 1, wherein said housing comprises a footwear insole.

45. The system according to claim 1, wherein said housing comprises a footwear midsole.

46. The system according to claim 1, wherein said housing comprises a deformable mold.

47. The system according to claim 1, wherein said housing comprises an erasable mold.

48. The system according to claim 1, wherein said housing comprises a device selected from the group consisting of a midsole and an insole, and wherein said housing has built-in supports and is filled with said particles for capturing a plantar foot impression, said built-in supports are pads located on a surface of said housing.

49. The system according to claim 1, wherein said particles are lubricated with a lubricant having a range of viscosities.

50. The system according to claim 1, wherein said particles have a Shore A hardness from about 10 to about 70.

51. The system according to claim 1, further comprising a midsole or insole cavity having a predetermined shape and support structure therein.

52. The system according to claim 1, further comprising a midsole having a forward portion, wherein said forward portion consists of about ⅓ of said midsole and has a lower cavity to limit an amount of particles distributed under a forefoot.

53. The system according to claim 1, wherein said housing comprises an outlet for release of said gas and/or liquid.

54. The system according to claim 1, wherein said housing includes one or more holes to allow said gas and/or liquid to escape.

55. The system according to claim 1, further comprising an adhesive surface applied to said housing to reduce migration of said particles.

56. A method of producing a custom support device comprising:

disposing a subject item on a housing that is partially filled with a plurality of particles and a gas and/or liquid;

preventing particle migration in said housing from one or more areas of said housing; and removing at least a portion of said gas and/or liquid in said housing.

57. The method according to claim 54, further comprising vibrating said housing.

58. A three-dimensional (3-D) capture system comprising:

a flexible housing defining a reservoir therein;

a plurality of particles disposed in the reservoir;

a volume of a gas and/or liquid disposed in said reservoir;

a valve assembly, outlet or hole in communication with said reservoir for regulating a quantity of gas and/or liquid in said reservoir; and a vibrator for stimulating and distributing said particles to conform to a contour of a subject item.

59. A method of producing a custom support device comprising:

disposing a subject item on a housing that is partially filled with a plurality of particles, and a gas and/or liquid;

moving, forcibly, the subject item on a surface of the housing;

preventing particle migration in said housing from one or more areas of said housing; and removing at least a portion of gas and/or liquid in response to the moving.

60. A three-dimensional (3-D) capture system comprising:

a flexible housing defining a reservoir therein;

a plurality of particles disposed in said reservoir;

a vibrator mechanism for stimulating said particles into a desired location; and a gas and/or liquid disposed in said reservoir, wherein said plurality of particles and said gas and/or liquid within said housing maintain a contour of a subject item forcibly placed on said housing.

61. The system according to claim 60, further comprising a high viscosity substance to retain said plurality of particles in a substantially fixed position relative to one another.

62. A three-dimensional (3-D) capture system comprising:

a rigid or semi-rigid orthotic housing defining a reservoir therein;

a plurality of particles disposed in said reservoir;

a gas and/or liquid disposed in said reservoir;

a valve assembly, opening or hole in communication with said reservoir for regulating a quantity of said gas and/or liquid disposed in said reservoir; and a vibrator for stimulating and distributing said particles to conform to a contour of a subject item.

63. A footwear device, wherein said device is selected from a midsole and an insole, comprising:

a flexible housing defining a reservoir therein;

a plurality of particles disposed in the reservoir;

a gas and/or liquid disposed in said reservoir;

a valve assembly, opening or hole in communication with said reservoir for regulating a quantity of said gas and/or liquid disposed in said reservoir; and a vibrator for stimulating and distributing said particles to conform to a contour of said footwear device to that of a subject item.

64. A three-dimensional (3-D) capture system comprising:

a flexible housing defining a reservoir therein;

a plurality of particles disposed in said reservoir;

a liquid and/or gas disposed in said reservoir, wherein at least a portion of said gas and/or liquid is selectively removed from said reservoir for capturing a 3-D impression of a subject item;

a vibrator for stimulating and distributing said particles to conform to a contour of the housing; and an elevated air vacuum line, opening or hole in communication with said reservoir for permitting an escape of at least a portion of said gas and/or liquid from said reservoir in response to said subject item being disposed on said 3-D capture system.

65. The 3-D capture system according to claim 64, wherein said gas and/or liquid is permitted to flow through said elevated air vacuum line in only one direction.

66. The 3-D capture system according to claim 64, wherein said gas and/or liquid is permitted to flow through said elevated air vacuum line in both a forward and a reverse direction.

67. The system according to claim 66, wherein the vacuum line is connected to a manual check valve for output of said gas and/or liquid, and an additional line for input of said gas and/or liquid.

68. The 3-D capture system according to claim 64, further comprising a flap integrated into said elevated air vacuum line to selectively permit gas and/or liquid to flow through said elevated air vacuum line.

69. The 3-D capture system according to claim 64, wherein said 3-D capture system comprises a seating device.

70. A gripping device comprising:

a flexible housing defining a reservoir therein;

a plurality of particles disposed in said reservoir;

a gas and/or liquid disposed in said reservoir;

a valve assembly in communication with said reservoir for regulating a quantity of said gas and/or liquid disposed in said reservoir; and a layer of memory intensive material disposed about said housing.

71. The gripping device according to claim 70, wherein said valve assembly includes a valve for permitting the removal of at least a portion of said gas and/or liquid disposed in said reservoir.

72. The gripping device according to claim 70, wherein said valve assembly is connected to a vacuum.

73. The gripping device according to claim 70, wherein said housing is disposed about a handle of an athletic device.

74. The gripping device according to claim 70, wherein said gripping device is adapted for use with devices selected from the group consisting of a golf club, a baseball bat, a racquet, a pole, a steering wheel, a handlebar, a firearm handle, a power tool, and a hand tool.

75. The gripping device according to claim 70, wherein said valve assembly has an end opening that includes a screen to prevent particles from entering said valve assembly.

76. A method of producing a customized handle grip comprising:

disposing a user's hand on a housing that is partially filled with a plurality of particles, and a gas and/or liquid;

applying pressure to said housing with said hand;

removing at least a portion of said gas and/or liquid in said housing; and vibrating said housing.

77. The method according to claim 76, further comprising removing said hand, wherein a contour of said hand is retained on said housing.

78. The method of claim 76, wherein said removing at least a portion of said gas and/or liquid is accomplished by said pressure of said hand.

79. The method of claim 76, wherein said removing at least a portion of said gas and/or liquid is accomplished at least by a vacuum pump.

80. The process according to claim 1, wherein at least a portion of said particles are doped with a substance that can be fused together by applying an appropriately calibrated energy source.

* * * * *